US008535939B2

(12) United States Patent
Shimatani-Shibata et al.

(10) Patent No.: US 8,535,939 B2
(45) Date of Patent: Sep. 17, 2013

(54) TRANSFECTION VECTOR

(75) Inventors: Yuko Shimatani-Shibata, Nagano (JP); Hitomi Shimizu-Matsuhashi, Nagano (JP); Takayuki Sasaki, Nagano (JP)

(73) Assignee: Anaeropharma Science, Inc., Tokyo (JP)

( * ) Notice: Subject to any disclaimer, the term of this patent is extended or adjusted under 35 U.S.C. 154(b) by 28 days.

(21) Appl. No.: 13/015,806

(22) Filed: Jan. 28, 2011

(65) Prior Publication Data

US 2011/0189757 A1 Aug. 4, 2011

Related U.S. Application Data

(60) Provisional application No. 61/299,922, filed on Jan. 29, 2010.

(51) Int. Cl.
*C12N 15/00* (2006.01)
*C12N 1/21* (2006.01)

(52) U.S. Cl.
USPC .................................... 435/320.1; 435/252.3

(58) Field of Classification Search
USPC ...................................................... 435/320.1
See application file for complete search history.

(56) References Cited

U.S. PATENT DOCUMENTS

| | | | |
|---|---|---|---|
| 6,416,754 | B1 | 7/2002 | Brown et al. |
| 6,652,849 | B2 | 11/2003 | Brown et al. |
| 2003/0103952 | A1 | 6/2003 | Brown et al. |
| 2005/0025745 | A1 | 2/2005 | Fujimori et al. |
| 2008/0112928 | A1 | 5/2008 | Loessner et al. |
| 2009/0123426 | A1 | 5/2009 | Li et al. |
| 2011/0189758 | A1 | 8/2011 | Shimatani-Shibata et al. |
| 2011/0190472 | A1 | 8/2011 | Shimatani-Shibata et al. |

FOREIGN PATENT DOCUMENTS

| | | |
|---|---|---|
| EP | 1 227 152 A1 | 7/2002 |
| WO | WO 2007/136107 | 11/2007 |
| WO | WO 2008/091375 | 7/2008 |
| WO | WO 2009/128272 | 10/2009 |
| WO | WO 2010/126073 | 11/2010 |

OTHER PUBLICATIONS

Park et al.; Heterologous gene expression and secretion in Bifidobacterium longum; Lait; vol. 85 (2005) pp. 1-8.*
Kohno et al., Expression of EHEC verotoxin 1B subunit fused to secreted signal peptides of *S. bovis* alpha-amylase in *Bifidobacterium longum*. Journal of Japanese Biochemical Society. Shoroku CD, 4P-1212 (2007). Japanese.

Lee et al., Comparative genomic analysis of the gut bacterium *Bifidobacterium longum* reveals loci susceptible to deletion during pure culture growth. BMC Genomics. May 27, 2008;9:247.

MacConaill et al., Investigation of protein export in *Bifidobacterium breve* UCC2003. Appl Environ Microbiol. Dec. 2003;69(12):6994-7001.

Schell et al., The genome sequence of *Bifidobacterium longum* reflects its adaptation to the human gastrointestinal tract. Proc Natl Acad Sci U S A. Oct. 29, 2002;99(22):14422-7. Epub Oct. 15, 2002.

Rhim, S. L. et al., "Expression and secretion of *Bifidobacterium adolescentis* amylase by *Bifidobacterium longum*," *Biotechnology Letters* 2006; 28:163-168.

Shkoporov, A. N. et al., "Production of human basic fibroblast growth factor (FGF-2) in *Bifidobacterium breve* using a series of novel expression/secretion vectors," *Biotechnology Letters* 2008; 30:1983-1988.

Yazawa, K. et al., *"Bifidobacterium longum* as a delivery system for cancer gene therapy: Selective localization and growth in hypoxic tumors," *Cancer Gene Therapy* 2000; 7(2):269-274.

Yazawa, K. et al., *"Bifidobacterium longum* as a delivery system for gene therapy of chemically induced rat mammary tumors," *Breast Cancer Research and Treatment* 2001; 66:165-170.

Moon et al., Secretion of recombinant pediocin PA-1 by Bifidobacterium longum, using the signal sequence for bifidobacterial alpha-amylase. Appl Environ Microbiol. Sep. 2005;71(9):5630-2.

* cited by examiner

*Primary Examiner* — Michele K Joike
*Assistant Examiner* — Antonio Galisteo Gonzalez
(74) *Attorney, Agent, or Firm* — Wolf, Greenfield & Sacks, P.C.

(57) ABSTRACT

The present invention relates to a secretory signal, a plasmid containing the secretory signal, a transformed anaerobic bacterium transformed with said plasmid, a gene transfer carrier consisting of said anaerobic bacterium, and a pharmaceutical composition containing said carrier.

23 Claims, 17 Drawing Sheets

[Fig.2]

Fig. 8
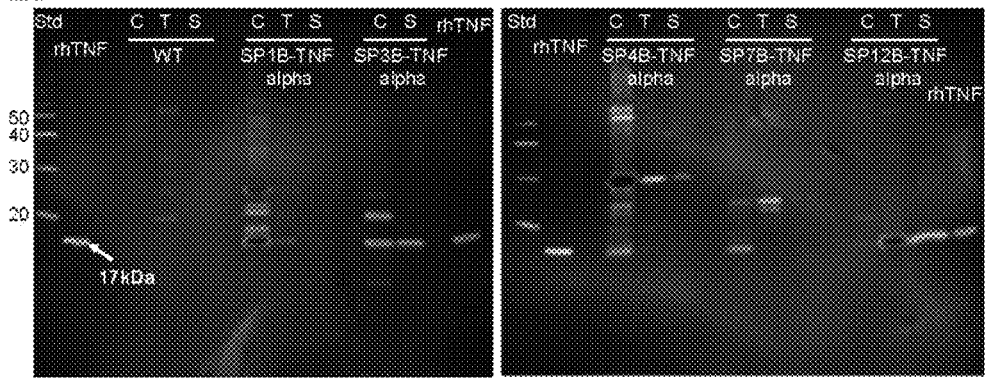
C: Intracellular protein
T: Concentrated sup by TCA precipitation
S: Supernatant
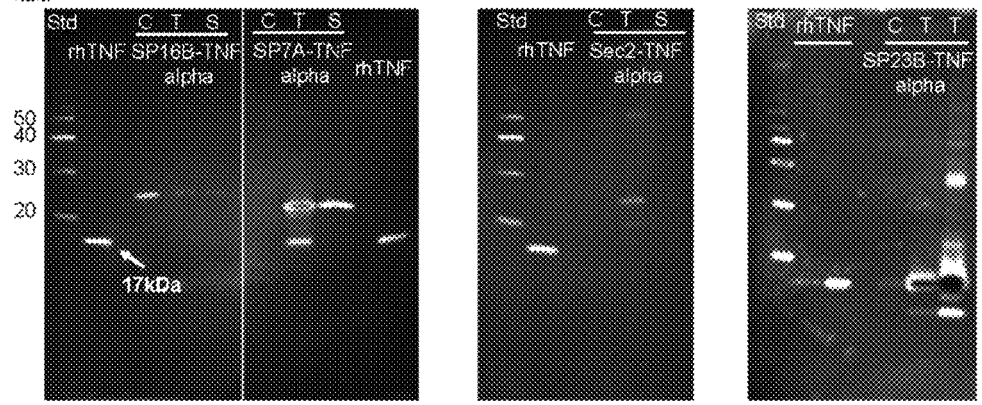
C: Intracellular protein
T: Concentrated sup by TCA precipitation
S: Supernatant Lane 1: *B. longum* 105A/pTNF3 intracellular extract
Lane 2: *B. longum* 105A intracellular extract
Lane 3: *B. longum* 105A/pTNF3 culture supernatant
Lane 4: *B. longum* 105A culture supernatant Fig.10
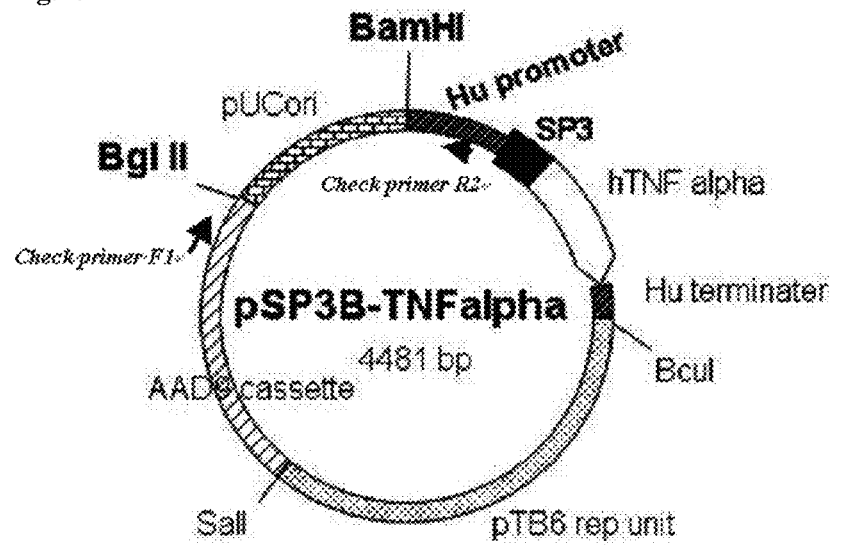
- Digestion with Bam HI and Bgl II
- Large fragment (3.8 kbp) recovery
- Self-ligation
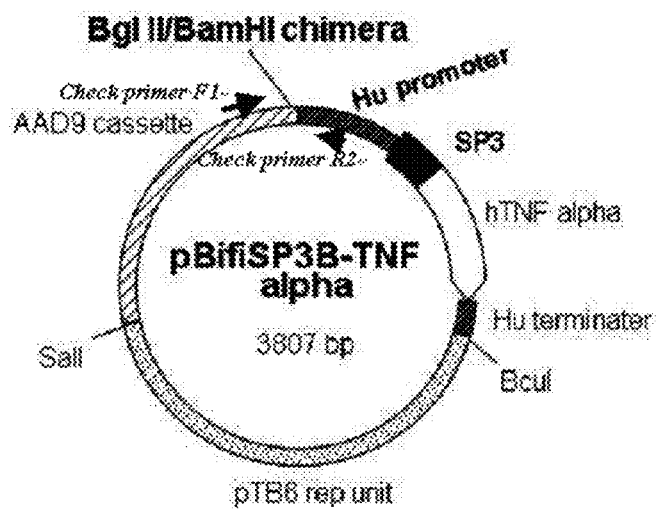

Fig.11

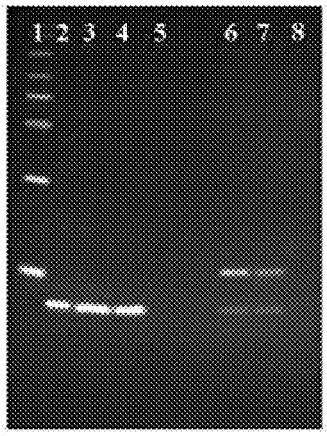

Lane 1: Molecular weight marker
Lane 2: Human recombinant TNF-alpha (positive control)
Lane 3: *B. longum* 105A/pBifiSP3B-TNF alpha culture supernatant
Lane 4: *B. longum* 105A/pSP3B-TNF alpha culture supernatant
Lane 5: *B. longum* 105A culture supernatant
Lane 6: *B. longum* 105A/pBifiSP3B-TNF alpha intracellular extract
Lane 7: *B. longum* 105A/pSP3B-TNF alpha intracellular extract
Lane 8: *B. longum* 105A intracellular extract

Fig.12

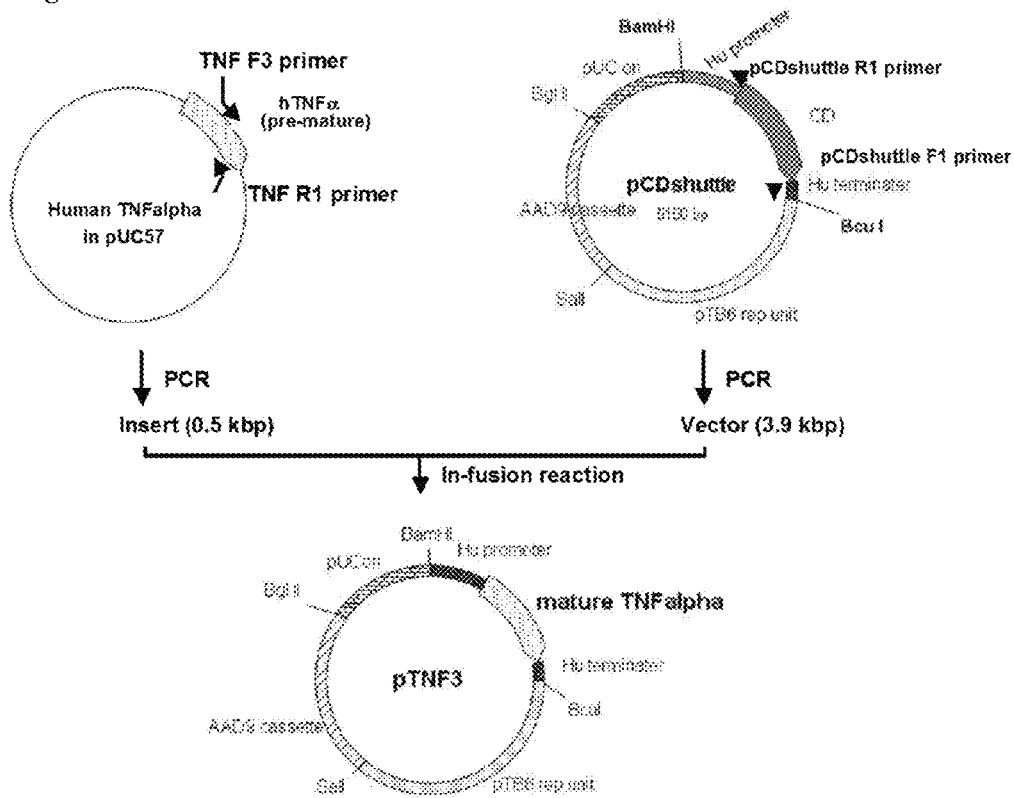

```
                          SEQUENCE LISTING

<160> NUMBER OF SEQ ID NOS: 144

<210> SEQ ID NO 1
<211> LENGTH: 4586
<212> TYPE: DNA
<213> ORGANISM: Artificial
<220> FEATURE:
<223> OTHER INFORMATION: sequence of plasmid pAmyB-GFPuv

<400> SEQUENCE: 1
ggatccgggc atcgccgaat atactcccac cacacaacaa gttagggtgg tacaaaacac        60
catcaattaa gtaccacctt tgcaaacatt ttcacaaatg aaagagttgt ttcagcaacg       120
attttcattg ttttttccaa ggcttttcgc actttagcac cctagaaaag gtataaaata       180
aacagcatac gttcgcaata gtgcaaacgc tatcaaagaa gatgaacccc cgttaaaggg       240
attgaagaaa aggaataaag gagccatgaa acatcggaaa cccgcaccgg cctggcatag       300
gctggggctg aagattagca agaaagtggt ggtcggcatc accgccgcgg cgaccgcctt       360
cggcggactg gcaatcgcca gcaccgcagc acaggcctcc aagggcgagg agctgttcac       420
cggcgtggtg ccgatcctgg tggagctgga cggcgacgtg aacggccaca gttctccgt       480 gtccggcgag ggcgagggcg acgccaccta cggcaagctg accctgaagt tcatctgcac       540
caccggcaag ctgccggtgc cgtggccgac cctggtgacc accttctcct acggcgtgca       600
gtgcttctcc cgctacccgg accacatgaa gcgccacgac ttcttcaagt ccgccatgcc       660
ggagggctac gtgcaggagc gcaccatctc cttcaaggac gacggcaact acaagacccg       720
cgccgaggtg aagttcgagg gcgacaccct ggtgaaccgc atcgagctga agggcatcga       780
cttcaaggaa gacggcaaca tcctgggcca caagctggag tacaactaca actcccacaa       840
cgtgtacatc accgccgaca gcagaagaa cggcatcaag gccaacttca agatccgcca       900
caacatcgag gacggctccg tgcagctggc cgaccactac cagcagaaca ccccgatcgg       960
cgacggcccg gtgctgctgc cggacaacca ctacctgtcc acccagtccg ccctgtccaa      1020
ggacccgaac gagaagcgcg accacatggt gctgctggag ttcgtgaccg ccgccggcat      1080
cacccacggc atggacgagc tgtacaagta accttctgct cgtagcgatt acttcgagca      1140
ttactgacga caaagacccc gaccgagatg gtcgggtct ttttgttgtg gtgctgtgac      1200
gtgttgtcca accgtattat tccggactag tcctccagga cctcgtctac gaggcgctga      1260
gcgaggaatg gcgcaaaagg gacggcgaga tcagcgaccc atgggccaac gacgaggcgg      1320
acggatacca gccgccctca tacgagccgg tcaaccccga acgcaggact ccccagacgc      1380
cctccgatgg cctgatctga cgtccgaaaa aaggcgctgt gcgccctttt taaatctttt      1440
ataaatcttt ttcattcttt ttagccctc cgcagcctta ctctcccaac gggtttcagc      1500
cgaaacctac accaaaaggg gagcgaacct acaccaaaag gggagcgaac ctacaccaaa      1560
aggggagcga acctacacca aaagggga gc tatatacacc ttttgttatt taaggtgcaa      1620
```

-continued

```
gttgtgctat gctgaggcca tgtccaatga gatcgtgaag ttcagcaacc agttcaacaa    1680
cgtcgcgctg aagaagttcg acgccgtgca cctggacgtg ctcatggcga tcgcctcaag    1740
ggtgagggag aagggcacgg ccacggtgga gttctcgttc gaggagctgc gcggcctcat    1800
gcgattgagg aagaacctga ccaacaagca gctggccgac aagatcgtgc agacgaacgc    1860
gcgcctgctg gcgctgaact acatgttcga ggattcgggc aagatcatcc agttcgcgct    1920
gttcacgaag ttcgtcaccg acccgcagga ggcgactctc gcggttgggg tcaacgagga    1980
gttcgcgttc ctgctcaacg acctgaccag ccagttcacg cgcttcgagc tggccgagtt    2040
cgccgacctc aagagcaagt acgccaagga gttctaccgc agggccaagc agtaccgcag    2100
ctccggaatc tggaagatcg gccgcgacga gttctgccga ctgcttggcg ttccaccgtc    2160
ggcaataacc cagacacgat atctgaatca gaaggttctt cagccaattc aggaggagtg    2220
tgggcctctc cttggcctga agatcgagcg ccagtacgtg aaacgcaggc tgtcgggctt    2280
cgtgttcaca ttcgcccgcg agacccctcc ggtgatcgac gccaggcccg tggaggcgag    2340
gaagacggac ggcgacggca agggccattg gacgagcgtt gccgggtacg gcgaggtgtt    2400
cacgaccacg gcgttgttcg acgtgacggc cgcccgggct cacttcgacg gcaccgttga    2460
agccggggag tgccgtttct gcgcgtttga cgcgcgcaac cgcgaacatc atgcgcggaa    2520
cgccggaagg ctgttctagc ggccgtgtcc gcgcctctgg ggcggttgcg cctgccatgg    2580
gtcgatctgc cgctgttcgg cctcacgctg gtctgtgcgc tgcctgatct ccctgagcag    2640
gtcggccttg gtcctggggg cgcttcgctc ctcgaacggg ccgctctccc ccaggtcctc    2700
gggctcgctc aggtccaacg gctcgtcacc ggacggctcg ggccggttct ctccctgtgc    2760
cgggttctcc gcctgtgcgc gttgttcggc catgcgcagt gcgagggcct tcacctgttc    2820
ggggcttgtc gactcgattt tcgttcgtga atacatgtta taataactat aactaataac    2880
gtaacgtgac tggcaagaga tattttaaa acaatgaata ggtttacact tactttagtt     2940
ttatggaaat gaaagatcat atcatatata atctagaata aaattaacta aaataattat    3000
tatctagata aaaatttag aagccaatga aatctataaa taaactaaat taagtttatt     3060
taattaacaa ctatggatat aaaataggta ctaatcaaaa tagtgaggag gatatatttg    3120
aatacatacg aacaaattaa taaagtgaaa aaaatacttc ggaaacattt aaaaaataac    3180
cttattggta cttacatgtt tggatcagga gttgagagtg gactaaaacc aaatagtgat    3240
cttgactttt tagtcgtcgt atctgaacca ttgacagatc aaagtaaaga aatacttata    3300
caaaaaatta gacctatttc aaaaaaaata ggagataaaa gcaacttacg atatattgaa    3360
ttaacaatta ttattcagca agaaatggta ccgtggaatc atcctcccaa acaagaattt    3420
atttatggag aatggttaca agagctttat gaacaaggat acattcctca gaaggaatta    3480
aattcagatt taaccataat gctttaccaa gcaaaacgaa aaaataaaag aatatacgga    3540
aattatgact tagaggaatt actacctgat attccatttt ctgatgtgag aagagccatt    3600
atggattcgt cagaggaatt aatagataat tatcaggatg atgaaaccaa ctctatatta    3660
actttatgcc gtatgatttt aactatggac acgggtaaaa tcataccaaa agatattgcg    3720
ggaaatgcag tggctgaatc ttctccatta gaacataggg agagaatttt gttagcagtt    3780
cgtagttatc ttggagagaa tattgaatgg actaatgaaa atgtaaattt aactataaac    3840
tatttaaata acagattaaa aaaattaaa aaaaattgaa aaaatggtgg aaacacttttt    3900 ttcaattttt ttagatcttg agcaaaaggc cagcaaaagg ccaggaaccg taaaaaggcc    3960
gcgttgctgg cgttttttcca taggctccgc cccccctgacg agcatcacaa aaatcgacgc    4020
```

```
tcaagtcaga ggtggcgaaa cccgacagga ctataaagat accaggcgtt tccccctgga    4080
agctccctcg tgcgctctcc tgttccgacc ctgccgctta ccggatacct gtccgccttt    4140
ctcccttcgg gaagcgtggc gctttctcat agctcacgct gtaggtatct cagttcggtg    4200
taggtcgttc gctccaagct gggctgtgtg cacgaacccc ccgttcagcc cgaccgctgc    4260
gccttatccg gtaactatcg tcttgagtcc aacccggtaa gacacgactt atcgccactg    4320
gcagcagcca ctggtaacag gattagcaga gcgaggtatg taggcggtgc tacagagttc    4380
ttgaagtggt ggcctaacta cggctacact agaagaacag tatttggtat ctgcgctctg    4440
ctgaagccag ttaccttcgg aaaaagagtt ggtagctctt gatccggcaa acaaaccacc    4500
gctggtagcg gtggtttttt tgtttgcaag cagcagatta cgcgcagaaa aaaggatct    4560 caagaagatc ctttgatctt ttctac                                         4586

<210> SEQ ID NO 2
<211> LENGTH: 4565
<212> TYPE: DNA
<213> ORGANISM: Artificial
<220> FEATURE:
<223> OTHER INFORMATION: sequence of plasmid pScHuGFPuv

<400> SEQUENCE: 2
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg gttttcgca gaaacatgcg     300 ctagtatcat tgatgacaac atggactaag caaaagtgct tgtcccctga cccaagaagg     360
atgctttatg aagcttttcca agggcgagga gctgttcacc ggcgtggtgc cgatcctggt     420
ggagctggac ggcgacgtga acggccacaa gttctccgtg tccggcgagg gcgagggcga     480
cgccacctac ggcaagctga ccctgaagtt catctgcacc accggcaagc tgccggtgcc     540
gtggccgacc ctggtgacca ccttctccta cggcgtgcag tgcttctccc gctacccgga     600
ccacatgaag cgccacgact tcttcaagtc cgccatgccg gagggctacg tgcaggagcg     660
caccatctcc ttcaaggacg acggcaacta caagacccgc gccgaggtga agttcgaggg     720
cgacaccctg gtgaaccgca tcgagctgaa gggcatcgac ttcaaggaag acggcaacat     780
cctgggccac aagctggagt acaactacaa ctcccacaac gtgtacatca ccgccgacaa     840
gcagaagaac ggcatcaagg ccaacttcaa gatccgccac aacatcgagg acggctccgt     900
gcagctggcc gaccactacc agcagaacac ccccatcggc gacggccccg tgctgctgcc     960
ggacaaccac tacctgtcca cccagtccgc cctgtccaag gacccgaacg agaagcgcga    1020
ccacatggtg ctgctggagt tcgtgaccgc cgccgggcatc acccacggca tggacgagct    1080
gtacaagtaa ccttctgctc gtagcgatta cttcgagcat tactgacgac aaagaccccg    1140
accgagatgg tcgggtgtctt tttgttgtgg tgctgtgacg tgttgtccaa ccgtattatt    1200
ccggactagt cctccaggac ctcgtctacg aggcgctgag cgaggaatgg cgcaaagggg    1260
acggcgagat cagcgaccca tgggccaacg acgaggcgga cggataccag ccgccctcat    1320
acgagccggt caaccccgaa cgcaggactc cccagacgcc ctccgatggc ctgatctgac    1380
gtccgaaaaa aggcgctgtg cgccctttt aaatctttta taatctttt tacattcttt    1440 tagccccctcc gcagccttac tctcccaacg ggtttcagcc gaaacctaca ccaaaagggg    1500
```

```
agcgaaccta caccaaaagg ggagcgaacc tacaccaaaa ggggagcgaa cctacaccaa   1560
aaggggagct atatacacct tttgttattt aaggtgcaag ttgtgctatg ctgaggccat   1620
gtccaatgag atcgtgaagt tcagcaacca gttcaacaac gtcgcgctga agaagttcga   1680
cgccgtgcac ctggacgtgc tcatggcgat cgcctcaagg gtgagggaga agggcacggc   1740
cacggtggag ttctcgttcg aggagctgcg cggcctcatg cgattgagga agaacctgac   1800
caacaagcag ctggccgaca agatcgtgca gacgaacgcg cgcctgctgg cgctgaacta   1860
catgttcgag gattcgggca agatcatcca gttcgcgctg ttcacgaagt cgtcaccga   1920 cccgcaggag gcgactctcg cggttggggt caacgaggag ttcgcgttcc tgctcaacga   1980
cctgaccagc cagttcacgc gcttcgagct ggccgagttc gccgacctca gagcaagta   2040 cgccaaggag ttctaccgca gggccaagca gtaccgcagc tccggaatct ggaagatcgg   2100
ccgcgacgag ttctgccgac tgcttggcgt tccaccgtcg gcaataaccc agacacgata   2160
tctgaatcag aaggttcttc agccaattca ggaggagtgt gggcctctcc ttggcctgaa   2220
gatcgagcgc cagtacgtga aacgcaggct gtcgggcttc gtgttcacat cgcccgcga   2280 gaccctccg gtgatcgacg ccaggcccgt ggaggcgagg aagacggacg gcgacggcaa   2340
gggccattgg acgagcgttg ccgggtacgg cgaggtgttc acgaccacgg cgttgttcga   2400
cgtgacggcc gccgggctc acttcgacgg caccgttgaa gccggggagt gccgtttctg   2460
cgcgtttgac gcgcgcaacc gcgaacatca tgcgcggaac gccggaaggc tgttctagcg   2520
gccgtgtccg cgcctctggg gcggttgcgc ctgccatggg tcgatctgcc gctgttcggc   2580
ctcacgctgg tctgtgcgct gcctgatctc cctgagcagg tcggccttgg tcctgggggc   2640
gcttcgctcc tcgaacgggc cgctctcccc caggtcctcg gctcgctca ggtccaacgg   2700 ctcgtcaccg gacggctcgg gccggttctc tccctgtgcc gggttctccg cctgtgcgcg   2760
ttgttcggcc atgcgcagtg cgagggcctt cacctgttcg gggcttgtcg actcgatttt   2820
cgttcgtgaa tacatgttat aataactata actaataacg taacgtgact ggcaagagat   2880
atttttaaaa caatgaatag gtttacactt actttagttt tatggaaatg aaagatcata   2940
tcatatataa tctagaataa aattaactaa aataattatt atctagataa aaatttaga   3000 agccaatgaa atctataaat aaactaaatt aagtttattt aattaacaac tatggatata   3060
aaataggtac taatcaaaat agtgaggagg atatatttga atacatacga acaaattaat   3120
aaagtgaaaa aaatacttcg gaaacattta aaaaataacc ttattggtac ttacatgttt   3180
ggatcaggag ttgagagtgg actaaaacca aatagtgatc ttgactttt agtcgtcgta   3240 tctgaaccat tgacagatca aagtaaagaa atacttatac aaaaaattag acctatttca   3300
aaaaaaatag gagataaaag caacttacga tatattgaat taacaattat tattcagcaa   3360
gaaatggtac cgtggaatca tcctcccaaa caagaattta tttatggaga atggttacaa   3420
gagctttatg aacaaggata cattcctcag aaggaattaa attcagattt aaccataatg   3480
ctttaccaag caaaacgaaa aaataaaaga atatacggaa attatgactt agaggaatta   3540
ctacctgata ttccattttc tgatgtgaga agagccatta tggattcgtc agaggaatta   3600
atagataatt atcaggatga tgaaaccaac tctatattaa ctttatgccg tatgatttta   3660
actatggaca cgggtaaaat cataccaaaa gatattgcgg gaaatgcagt ggctgaatct   3720
tctccattag aacataggga gagaattttg ttagcagttc gtagttatct tggagagaat   3780
attgaatgga ctaatgaaaa tgtaaattta actataaact atttaaataa cagattaaaa   3840
aaattataaa aaaattgaaa aaatggtgga aacactttt tcaattttt tagatcttga   3900
```

-continued

| | | | | |
|---|---|---|---|---|
| gcaaaaggcc | agcaaaaggc | caggaaccgt | aaaaaggccg | cgttgctggc gttttccat | 3960 |
| aggctccgcc | cccctgacga | gcatcacaaa | atcgacgct | caagtcagag gtggcgaaac | 4020 |
| ccgacaggac | tataaagata | ccaggcgttt | ccccctggaa | gctccctcgt gcgctctcct | 4080 |
| gttccgaccc | tgccgcttac | cggatacctg | tccgcctttc | tcccttcggg aagcgtggcg | 4140 |
| ctttctcata | gctcacgctg | taggtatctc | agttcggtgt | aggtcgttcg ctccaagctg | 4200 |
| ggctgtgtgc | acgaaccccc | cgttcagccc | gaccgctgcg | ccttatccgg taactatcgt | 4260 |
| cttgagtcca | acccggtaag | acacgactta | tcgccactgg | cagcagccac tggtaacagg | 4320 |
| attagcagag | cgaggtatgt | aggcggtgct | acagagttct | tgaagtggtg gcctaactac | 4380 |
| ggctacacta | gaagaacagt | atttggtatc | tgcgctctgc | tgaagccagt taccttcgga | 4440 |
| aaaagagttg | gtagctcttg | atccggcaaa | caaaccaccg | ctggtagcgg tggttttttt | 4500 |
| gtttgcaagc | agcagattac | gcgcagaaaa | aaaggatctc | aagaagatcc tttgatcttt | 4560 |
| tctac | | | | | 4565 |

<210> SEQ ID NO 3
<211> LENGTH: 4790
<212> TYPE: DNA
<213> ORGANISM: Artificial
<220> FEATURE:
<223> OTHER INFORMATION: sequence of plasmid pSec2-GFP

<400> SEQUENCE: 3

| | | | | |
|---|---|---|---|---|
| ggatccgtct | tcctgctggc | ctatgcattg | ggttccgcag | tgcccactcc aggcggtctg | 60 |
| ggcggtgtgg | aagcggcgct | gacattcgcg | ttcgtggcgg | tcggagtgcc gcagggcgtg | 120 |
| gcgctttccg | ccactttgct | gcaccgcgtg | gtgttctact | ggctgcgcat tccgctgggc | 180 |
| gcggcggcca | tgaagtggct | tgacaagcat | aatcttgtct | gattcgtcta ttttcatacc | 240 |
| cccttcgggg | aaatagatgt | gaaaacccctt | ataaaacgcg | gttttcgca gaaacatgcg | 300 |
| ctagtatcat | tgatgacaac | atggactaag | caaaagtgct | tgtcccctga cccaagaagg | 360 |
| atgcttttg | gaacatatga | agatgttccg | gcacctatcc | tccgtttttg ctattgcgac | 420 |
| cattgcgccg | ctggcgttgg | cggccacgct | agccgtgacg | cctgcaatcg cacaggccga | 480 |
| ccagctgccc | aacccggatt | gggtggcatt | gctctccgac | tacgaaaaga actattggca | 540 |
| ggcccccgcc | gatgccgaac | acggtggcaa | ggtgctcgac | gccgatacaa tgaaactcga | 600 |
| ctccaagggc | gaggagctgt | tcaccggcgt | ggtgccgatc | ctggtggagc tggacggcga | 660 |
| cgtgaacggc | cacaagttct | ccgtgtccgg | cgagggcgag | ggcgacgcca cctacggcaa | 720 |
| gctgaccctg | aagttcatct | gcaccaccgg | caagctgccg | gtgccgtggc cgaccctggt | 780 |
| gaccaccttc | tcctacggcg | tgcagtgctt | ctcccgctac | ccggaccaca tgaagcgcca | 840 |
| cgacttcttc | aagtccgcca | tgccggaggg | ctacgtgcag | gagcgcacca tctccttcaa | 900 |
| ggacgacggc | aactacaaga | cccgcgccga | ggtgaagttc | gagggcgaca ccctggtgaa | 960 |
| ccgcatcgag | ctgaagggca | tcgacttcaa | ggaagacggc | aacatcctgg ccacaagct | 1020 |
| ggagtacaac | tacaactccc | acaacgtgta | catcaccgcc | gacaagcaga gaacggcat | 1080 |
| caaggccaac | ttcaagatcc | gccacaacat | cgaggacggc | tccgtgcagc tggccgacca | 1140 |
| ctaccagcag | aacacccga | tcggcgacgg | cccggtgctg | ctgccggaca ccactacct | 1200 |
| gtccacccag | tccgccctgt | ccaaggaccc | gaacgagaag | cgcgaccaca tggtgctgct | 1260 |
| ggagttcgtg | accgccgccg | gcatcaccca | cggcatggac | gagctgtaca gtaaccttc | 1320 |
| tgctcgtagc | gattacttcg | agcattactg | acgacaaaga | ccccgaccga gatggtcggg | 1380 |

```
gtcttttttgt tgtggtgctg tgacgtgttg tccaaccgta ttattccgga ctagtcctcc    1440
aggacctcgt ctacgaggcg ctgagcgagg aatggcgcaa aagggacggc gagatcagcg    1500
acccatgggc caacgacgag gcggacggat accagccgcc ctcatacgag ccggtcaacc    1560
ccgaacgcag gactccccag acgccctccg atggcctgat ctgacgtccg aaaaaaggcg    1620
ctgtgcgccc ttttaaaatc ttttataaat cttttacat tcttttagcc cctccgcagc    1680
cttactctcc caacgggttt cagccgaaac ctacaccaaa aggggagcga acctacacca    1740 aagggagc gaacctacac caaaagggga gcgaacctac accaaaggg gagctatata    1800 cacctttgt tatttaaggt gcaagttgtg ctatgctgag gccatgtcca atgagatcgt    1860
gaagttcagc aaccagttca caacgtcgc gctgaagaag ttcgacgccg tgcacctgga    1920
cgtgctcatg gcgatcgcct caaggtgag ggagaagggc acggccacgg tggagttctc    1980
gttcgaggag ctgcgcggcc tcatgcgatt gaggaagaac ctgaccaaca agcagctggc    2040
cgacaagatc gtgcagacga acgcgcgcct gctggcgctg aactacatgt tcgaggattc    2100
gggcaagatc atccagttcg cgctgttcac gaagttcgtc accgacccgc aggaggcgac    2160
tctcgcggtt ggggtcaacg aggagttcgc gttcctgctc aacgacctga ccagccagtt    2220
cacgcgcttc gagctggccg agttcgccga cctcaagagc aagtacgcca aggagttcta    2280
ccgcagggcc aagcagtacc gcagctccgg aatctggaag atcggccgcg acgagttctg    2340
ccgactgctt ggcgttccac cgtcggcaat aacccagaca cgatatctga atcagaaggt    2400
tcttcagcca attcaggagg agtgtgggcc tctccttggc ctgaagatcg agcgccagta    2460
cgtgaaacgc aggctgtcgg gcttcgtgtt cacattcgcc cgcgagaccc ctccggtgat    2520
cgacgccagg cccgtggagg cgaggaagac ggacggcgac ggcaagggcc attggacgag    2580
cgttccgggg tacggcgagg tgttcacgac cacgcgttg ttcgacgtga cggccgcccg    2640
ggctcacttc gacggcaccg ttgaagccgg ggagtgccgt ttctgcgcgt ttgacgcgcg    2700
caaccgcgaa catcatgcgc ggaacgccgg aaggctgttc tagcggccgt gtccgcgcct    2760
ctggggcggt tgcgcctgcc atgggtcgat ctgccgctgt tcggcctcac gctggtctgt    2820
gcgctgcctg atctccctga gcaggtcggc cttggtcctg ggggcgcttc gctcctcgaa    2880
cgggccgctc tcccccaggt cctcgggctc gctcaggtcc aacggctcgt caccggacgg    2940
ctcgggccgg ttctctccct gtgccgggtt ctccgcctgt gcgcgttgtt cggccatgcg    3000
cagtgcgagg gccttcacct gttcggggct tgtcgactcg attttcgttc gtgaatacat    3060
gttataataa ctataactaa taacgtaacg tgactggcaa gagatatttt taaaacaatg    3120
aataggttta cacttacttt agttttatgg aaatgaaaga tcatatcata tataatctag    3180
aataaaatta actaaaataa ttattatcta gataaaaaat ttagaagcca atgaaatcta    3240
taaataaact aaattaagtt tatttaatta acaactatgg atataaaata ggtactaatc    3300
aaaatagtga ggaggatata tttgaataca tacgaacaaa ttaataaagt gaaaaaaata    3360
cttcggaaac atttaaaaaa taaccttatt ggtacttaca tgtttggatc aggagttgag    3420
agtggactaa aaccaaatag tgatcttgac ttttagtcg tcgtatctga accattgaca    3480
gatcaaagta aagaaatact tatacaaaaa attagaccta tttcaaaaaa aataggagat    3540
aaaagcaact tacgatatat tgaattaaca attattattc agcaagaaat ggtaccgtgg    3600
aatcatcctc ccaaacaaga atttatttat ggagaatggt tacaagagct ttatgaacaa    3660
ggatacattc tcagaagga attaaattca gatttaacca taatgcttta ccaagcaaaa    3720
cgaaaaaata aagaatata cggaaattat gacttagagg aattactacc tgatattcca    3780
```

-continued

```
ttttctgatg tgagaagagc cattatggat tcgtcagagg aattaataga taattatcag    3840
gatgatgaaa ccaactctat attaacttta tgccgtatga ttttaactat ggacacgggt    3900
aaaatcatac caaaagatat tgcgggaaat gcagtggctg aatcttctcc attagaacat    3960
agggagagaa ttttgttagc agttcgtagt tatcttggag agaatattga atggactaat    4020
gaaaatgtaa atttaactat aaactattta aataacagat taaaaaaatt ataaaaaaat    4080
tgaaaaaatg gtggaaacac ttttttcaat tttttttagat cttgagcaaa aggccagcaa    4140
aaggccagga accgtaaaaa ggccgcgttg ctggcgtttt tccataggct ccgcccccct    4200
gacgagcatc acaaaaatcg acgctcaagt cagaggtggc gaaacccgac aggactataa    4260
agataccagg cgtttccccc tggaagctcc ctcgtgcgct ctcctgttcc gaccctgccg    4320
cttaccggat acctgtccgc ctttctccct tcgggaagcg tggcgctttc tcatagctca    4380
cgctgtaggt atctcagttc ggtgtaggtc gttcgctcca agctgggctg tgtgcacgaa    4440
ccccccgttc agcccgaccg ctgcgcctta tccggtaact atcgtcttga gtccaacccg    4500
gtaagacacg acttatcgcc actggcagca gccactggta acaggattag cagagcgagg    4560
tatgtaggcg tgctacaga gttcttgaag tggtggccta actacggcta cactagaaga    4620
acagtatttg gtatctgcgc tctgctgaag ccagttacct tcggaaaaag agttggtagc    4680
tcttgatccg gcaaacaaac caccgctggt agcggtggtt tttttgtttg caagcagcag    4740
attacgcgca gaaaaaaagg atctcaagaa gatcctttga tcttttctac              4790
```

<210> SEQ ID NO 4
<211> LENGTH: 4544
<212> TYPE: DNA
<213> ORGANISM: Artificial
<220> FEATURE:
<223> OTHER INFORMATION: sequence of plasmid pTNF1

<400> SEQUENCE: 4

```
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
ccccttcgggg aaatagatgt gaaaacccctt ataaaacgcg ggttttcgca gaaacatgcg     300
ctagtatcat tgatgacaac atggactaag caaaagtgct tgtcccctga cccaagaagg     360
atgctttatg tccaccgaat ccatgatccg tgacgtggga ctggccgagg aagccctgcc     420
gaagaagacc ggcggcccgc agggctcccg ccgctgcctg ttcctgtccc tgttctcctt     480
cctgatcgtg gccggcgcca ccaccctgtt ctgcctgctg cacttcggcg tcatcggccc     540
gcagcgtgag gaattcccgc gcgacctgtc cctgatctcc ccgctggccc aggccgtgcg     600
ctcctcctcc cgtaccccgt ccgataagcc ggtcgcccat gtggtcgcca acccgcaggc     660
cgagggccag ctgcagtggc tgaaccgtcg cgccaacgcc ctgctggcca acggcgtgga     720
actgcgcgac aaccagctgg tcgtgccgtc cgagggcctg tacctgatct actcccaggt     780
gctgttcaag ggcagggct gcccgtccac ccagtcctg ctgacccata ccatctcccg     840
catcgccgtg tcctaccaga ccaaggtcaa cctgctgtcc gccatcaagt ccccgtgcca     900
gcgtgagacc ccggaaggcg ccgaggcaa gccgtggtac gaaccgatct acctgggcgg     960
cgtgttccag ctggaaaagg gcgatcgtct gtccgccgag atcaaccgtc cggactacct    1020
ggatttcgcc gagtccggcc aggtctactt cggcatcatc gccctgtgac cttctgctcg    1080
```

```
tagcgattac ttcgagcatt actgacgaca aagaccccga ccgagatggt cggggtcttt       1140
ttgttgtggt gctgtgacgt gttgtccaac cgtattattc cggactagtc ctccaggacc       1200
tcgtctacga ggcgctgagc gaggaatggc gcaaaaggga cggcgagatc agcgacccat       1260
gggccaacga cgaggcggac ggataccagc cgccctcata cgagccggtc aaccccgaac       1320
gcaggactcc ccagacgccc tccgatggcc tgatctgacg tccgaaaaaa ggcgctgtgc       1380
gcccttttta aatctttat aaatctttt acattctttt agcccctccg cagccttact        1440
ctcccaacgg gtttcagccg aaacctacac caaaagggga gcgaacctac accaaaaggg      1500
gagcgaacct acaccaaaag gggagcgaac ctacaccaaa aggggagcta tatacacctt      1560
ttgttattta aggtgcaagt tgtgctatgc tgaggccatg tccaatgaga tcgtgaagtt      1620
cagcaaccag ttcaacaacg tcgcgctgaa gaagttcgac gccgtgcacc tggacgtgct      1680
catggcgatc gcctcaaggg tgagggagaa gggcacggcc acggtggagt tctcgttcga     1740
ggagctgcgc ggcctcatgc gattgaggaa gaacctgacc aacaagcagc tggccgacaa     1800
gatcgtgcag acgaacgcgc gcctgctggc gctgaactac atgttcgagg attcgggcaa     1860
gatcatccga ttcgcgctgt tcacgaagtt cgtcaccgac ccgcaggagg cgactctcgc     1920
ggttggggtc aacgaggagt tcgcgttcct gctcaacgac ctgaccagcc agttcacgcg     1980
cttcgagctg gccgagttcg ccgacctcaa gagcaagtac gccaaggagt tctaccgcag     2040
ggccaagcag taccgcagct ccggaatctg gaagatcggc cgcgacgagt tctgccgact     2100
gcttggcgtt ccaccgtcgg caataaccca gacacgatat ctgaatcaga aggttcttca     2160
gccaattcag gaggagtgtg ggcctctcct tggcctgaag atcgagcgcc agtacgtgaa     2220
acgcaggctg tcgggcttcg tgttcacatt cgcccgcgag accctccgg tgatcgacgc      2280 caggcccgtg gaggcgagga agacggacgg cgacggcaag ggccattgga cgagcgttgc     2340
cgggtacggc gaggtgttca cgaccacggc gttgttcgac gtgacggccg cccgggctca     2400
cttcgacggc accgttgaag ccggggagtg ccgtttctgc gcgtttgacg cgcgcaaccg     2460
cgaacatcat gcgcggaacg ccggaaggct gttctagcgg ccgtgtccgc gcctctgggg     2520
cggttgcgcc tgccatgggt cgatctgccg ctgttcggcc tcacgctggt ctgtgcgctg     2580
cctgatctcc ctgagcaggt cggccttggt cctgggggcg cttcgctcct cgaacgggcc    2640
gctctccccc aggtcctcgg gctcgctcag gtccaacggc tcgtcaccgg acggctcggg    2700
ccggttctct ccctgtgccg ggttctccgc ctgtgcgcgt tgttcggcca tgcgcagtgc    2760
gagggccttc acctgttcgg ggcttgtcga ctcgattttc gttcgtgaat acatgttata    2820
ataactataa ctaataacgt aacgtgactg gcaagagata ttttaaaac aatgaatagg     2880 tttacactta ctttagtttt atggaaatga aagatcatat catatataat ctagaataaa    2940
attaactaaa ataattatta tctagataaa aaatttagaa gccaatgaaa tctataaata    3000
aactaaatta gtttattta attaacaact atggatataa aataggtact aatcaaaata     3060
gtgaggagga tatattgaa tacatacgaa caaattaata aagtgaaaaa aatacttcgg     3120
aaacatttaa aaaataacct tattggtact tacatgtttg gatcaggagt tgagagtgga    3180 ctaaaccaa atagtgatct tgactttta gtcgtcgtat ctgaaccatt gacagatcaa      3240
agtaaagaaa tacttataca aaaaattaga cctatttcaa aaaaaatagg agataaaagc    3300
aacttacgat atattgaatt aacaattatt attcagcaag aaatggtacc gtggaatcat    3360
cctcccaaac aagaatttat ttatggagaa tggttacaag agctttatga acaaggatac    3420
attcctcaga aggaattaaa ttcagattta accataatgc tttaccaagc aaaacgaaaa    3480
```

-continued

| | |
|---|---|
| aataaaagaa tatacggaaa ttatgactta gaggaattac tacctgatat tccatttctct | 3540 |
| gatgtgagaa gagccattat ggattcgtca gaggaattaa tagataatta tcaggatgat | 3600 |
| gaaaccaact ctatattaac tttatgccgt atgattttaa ctatggacac gggtaaaatc | 3660 |
| ataccaaaag atattgcggg aaatgcagtg gctgaatctt ctccattaga acatagggag | 3720 |
| agaattttgt tagcagttcg tagttatctt ggagagaata ttgaatggac taatgaaaat | 3780 |
| gtaaatttaa ctataaacta tttaaataac agattaaaaa aattataaaa aaattgaaaa | 3840 |
| aatggtggaa acactttttt caattttttt agatcttgag caaaaggcca gcaaaaggcc | 3900 |
| aggaaccgta aaaaggccgc gttgctggcg ttttttccata ggctccgccc ccctgacgag | 3960 |
| catcacaaaa atcgacgctc aagtcagagg tggcgaaacc cgacaggact ataaagatac | 4020 |
| caggcgtttc ccctggaag ctccctcgtg cgctctcctg ttccgaccct gccgcttacc | 4080 |
| ggatacctgt ccgcctttct cccttcggga agcgtggcgc tttctcatag ctcacgctgt | 4140 |
| aggtatctca gttcggtgta ggtcgttcgc tccaagctgg gctgtgtgca cgaaccccc | 4200 |
| gttcagcccg accgctgcgc cttatccggt aactatcgtc ttgagtccaa cccggtaaga | 4260 |
| cacgacttat cgccactggc agcagccact ggtaacagga ttagcagagc gaggtatgta | 4320 |
| ggcggtgcta cagagttctt gaagtggtgg cctaactacg gctacactag aagaacagta | 4380 |
| tttggtatct gcgctctgct gaagccagtt accttcggaa aaagagttgg tagctcttga | 4440 |
| tccggcaaac aaaccaccgc tggtagcggt ggtttttttg tttgcaagca gcagattacg | 4500 |
| cgcagaaaaa aaggatctca agaagatcct ttgatctttt ctac | 4544 |

<210> SEQ ID NO 5
<211> LENGTH: 3807
<212> TYPE: DNA
<213> ORGANISM: Artificial
<220> FEATURE:
<223> OTHER INFORMATION: sequence of plasmid pBifi-SP3BTNF alpha

<400> SEQUENCE: 5

| | |
|---|---|
| agatccgtct tcctgctggc ctatgcattg ggttccgcag tgcccactcc aggcggtctg | 60 |
| ggcggtgtgg aagcggcgct gacattcgcg ttcgtggcgg tcggagtgcc gcagggcgtg | 120 |
| gcgctttccg ccactttgct gcaccgcgtg gtgttctact ggctgcgcat tccgctgggc | 180 |
| gcggcggcca tgaagtggct tgacaagcat aatcttgtct gattcgtcta ttttcatacc | 240 |
| cccttcgggg aaatagatgt gaaaacccct ataaaacgcg gttttcgca gaaacatgcg | 300 |
| ctagtatcat tgatgacaac atggactaag caaaagtgct tgtcccctga cccaagaagg | 360 |
| atgctttatg ttcaataagc gacacatcgt ccgtaccatt gcggccaccg ccagcatcct | 420 |
| ggctctgtcg ttcaccgcag cctgcggttc cggccagtcc accgcatcca attccaccga | 480 |
| ttcggacgac atcacccagc agacgtacaa gccgggcaag ctgaccatcg ccgtgcgctc | 540 |
| ctcctcccgt accccgtccg ataagccggt cgcccatgtg tcgccaacc cgcaggccga | 600 |
| gggccagctg cagtggctga accgtcgcgc caacgccctg ctggccaacg gcgtggaact | 660 |
| gcgcgacaac cagctggtcg tgccgtccga gggcctgtac ctgatctact cccaggtgct | 720 |
| gttcaagggc cagggctgcc cgtccaccca cgtcctgctg acccatacca tctcccgcat | 780 |
| cgccgtgtcc taccagacca aggtcaacct gctgtccgcc atcaagtccc cgtgccagcg | 840 |
| tgagaccccg gaaggcgccg aggccaagcc gtggtacgaa ccgatctacc tgggcggcgt | 900 |
| gttccagctg gaaaagggcg atcgtctgtc cgccgagatc aaccgtccgg actacctgga | 960 |
| tttcgccgag tccggccagg tctacttcgg catcatcgcc ctgtgacctt ctgctcgtag | 1020 |

```
cgattacttc gagcattact gacgacaaag accccgaccg agatggtcgg ggtcttttg      1080
ttgtggtgct gtgacgtgtt gtccaaccgt attattccgg actagtcctc caggacctcg      1140
tctacgaggc gctgagcgag gaatggcgca aaagggacgg cgagatcagc gacccatggg      1200
ccaacgacga ggcggacgga taccagccgc cctcatacga gccggtcaac cccgaacgca      1260
ggactcccca gacgccctcc gatggcctga tctgacgtcc gaaaaaaggc gctgtgcgcc      1320
cttttaaat cttttataaa tcttttaca ttcttttagc ccctccgcag ccttactctc       1380
ccaacgggtt tcagccgaaa cctacaccaa aaggggagcg aacctacacc aaaagggag      1440
cgaacctaca ccaaaagggg agcgaaccta caccaaaagg ggagctatat caccttttg      1500
ttatttaagg tgcaagttgt gctatgctga ggccatgtcc aatgagatcg tgaagttcag      1560
caaccagttc aacaacgtcg cgctgaagaa gttcgacgcc gtgcacctgg acgtgctcat      1620
ggcgatcgcc tcaagggtga gggagaaggg cacggccacg gtggagttct cgttcgagga      1680
gctgcgcggc tcatgcgat tgaggaagaa cctgaccaac aagcagctgg ccgacaagat       1740
cgtgcagacg aacgcgcgcc tgctggcgct gaactacatg ttcgaggatt cgggcaagat      1800
catccagttc gcgctgttca cgaagttcgt caccgacccg caggaggcga ctctcgcggt      1860
tggggtcaac gaggagttcg cgttcctgct caacgacctg accagccagt tcacgcgctt      1920
cgagctggcc gagttcgccg acctcaagag caagtacgcc aaggagttct accgcagggc      1980
caagcagtac cgcagctccg gaatctggaa gatcggccgc gacgagttct gccgactgct      2040
tggcgttcca ccgtcggcaa taccccagac acgatatctg aatcagaagg ttcttcagcc      2100
aattcaggag gagtgtgggc ctctccttgg cctgaagatc gagcgccagt acgtgaaacg      2160
caggctgtcg ggcttcgtgt tcacattcgc ccgcgagacc cctccggtga tcgacgccag      2220
gcccgtggag gcgaggaaga cggacggcga cggcaagggc cattggacga cgttgccgg      2280
gtacggcgag gtgttcacga ccacggcgtt gttcgacgtg acggccgccc gggctcactt      2340
cgacggcacc gttgaagccg gggagtgccg tttctgcgcg tttgacgcgc gcaaccgcga      2400
acatcatgcg cggaacgccg gaaggctgtt ctagcggccg tgtccgcgcc tctgggggcgg     2460
ttgcgcctgc catgggtcga tctgccgctg ttcggcctca cgctggtctg tgcgctgcct      2520
gatctcccctg agcaggtcgg ccttggtcct ggggcgctt cgctcctcga acgggccgct      2580
ctcccccagg tcctcgggct cgctcaggtc caacggctcg tcaccggacg gctcgggccg      2640
gttctctccc tgtgccgggt tctccgcctg tgcgcgttgt tcggccatgc gcagtgcgag      2700
ggccttcacc tgttcgggc ttgtcgactc gattttcgtt cgtgaataca tgttataata      2760
actataacta ataacgtaac gtgactggca agagatattt ttaaaacaat gaataggttt      2820
acacttactt tagttttatg gaaatgaaag atcatatcat atataatcta gaataaaatt     2880
aactaaaata attattatct agataaaaaa tttagaagcc aatgaaatct ataaataaac      2940
taaattaagt ttatttaatt aacaactatg gatataaaat aggtactaat caaaatagtg      3000
aggaggatat atttgaatac atacgaacaa attaataaag tgaaaaaaat acttcggaaa      3060
catttaaaaa ataaccttat tggtacttac atgtttggat caggagttga gagtggacta      3120
aaaccaaata gtgatcttga ctttttagtc gtcgtatctg aaccattgac agatcaaagt      3180
aaagaaatac ttatacaaaa aattagacct atttcaaaaa aataggaga taaaagcaac      3240
ttacgatata ttgaattaac aattattatt cagcaagaaa tggtaccgtg gaatcatcct      3300
cccaaacaag aatttattta tggagaatgg ttacaagagc tttatgaaca aggatacatt      3360
cctcagaagg aattaaattc agatttaacc ataatgcttt accaagcaaa acgaaaaaat      3420
```

```
aaaagaatat acggaaatta tgacttagag gaattactac ctgatattcc attttctgat    3480
gtgagaagag ccattatgga ttcgtcagag gaattaatag ataattatca ggatgatgaa    3540
accaactcta tattaacttt atgccgtatg attttaacta tggacacggg taaaatcata    3600
ccaaaagata ttgcgggaaa tgcagtggct gaatcttctc cattagaaca tagggagaga    3660
attttgttag cagttcgtag ttatcttgga gagaatattg aatggactaa tgaaaatgta    3720
aatttaacta taaactattt aaataacaga ttaaaaaaat tataaaaaaa ttgaaaaaat    3780
ggtggaaaca cttttttcaa ttttttt                                       3807

<210> SEQ ID NO 6
<211> LENGTH: 141
<212> TYPE: DNA
<213> ORGANISM: Artificial
<220> FEATURE:
<223> OTHER INFORMATION: DNA sequence of signal peptide SP1

<400> SEQUENCE: 6
atggcggaaa ctaccgttaa gcccacgaag cttgctgtta ttggtgccgg tgccgttggc     60
tccaccctcg ccttcgccgc tgcccagcgt ggcatcgctc gcgagatcgt gcttgaagac    120
atcgccaagg agcgcgtgga a                                              141

<210> SEQ ID NO 7
<211> LENGTH: 156
<212> TYPE: DNA
<213> ORGANISM: Artificial
<220> FEATURE:
<223> OTHER INFORMATION: DNA sequence of signal peptide SP2

<400> SEQUENCE: 7
gtgggtatga ctgagaacgc cgtaaatact gccgtgactt ccacctcctc tcccgcaatt     60
cccgccgaga cttccgccgt ctcccccgca actcgcgcag ccaaccgccc gctgggcaca    120
ccgctgggca agcaccccac ccgcgtgctg tttttg                              156

<210> SEQ ID NO 8
<211> LENGTH: 165
<212> TYPE: DNA
<213> ORGANISM: Artificial
<220> FEATURE:
<223> OTHER INFORMATION: DNA sequence of signal peptide SP3

<400> SEQUENCE: 8
atgttcaata agcgacacat cgtccgtacc attgcggcca ccgccagcat cctggctctg     60
tcgttcaccg cagcctgcgg ttccggccag tccaccgcat ccaattccac cgattcggac    120
gacatcaccc agcagacgta caagccgggc aagctgacca tcgcc                    165

<210> SEQ ID NO 9
<211> LENGTH: 195
<212> TYPE: DNA
<213> ORGANISM: Artificial
<220> FEATURE:
<223> OTHER INFORMATION: DNA sequence of signal peptide SP4

<400> SEQUENCE: 9
atgaccactc acaacagcca gtattccgcc gaaaccgccc atcccgacaa gcaggaaagc     60
agcccggcgc cgaccgccgc cggcaccacg gccagtaacg tctccacaac tggcaacgca    120
accacgccgg acgccagcat cgcccctcaac gccgacgcca ctccggtagc cgacgttccc    180
ccgcgtctgt tcggc                                                     195
```

<210> SEQ ID NO 10
<211> LENGTH: 177
<212> TYPE: DNA
<213> ORGANISM: Artificial
<220> FEATURE:
<223> OTHER INFORMATION: DNA sequence of signal peptide SP5

<400> SEQUENCE: 10

```
atgaccgcga ttgacgagac cgaccagcgc atcctcacca tgctggaggc cgacggccgc    60
gccacgctcg cgcaactggc ccaggcgacc ggactgtccg tctccgccgc ccagtcgcgc   120
gtgcagaagc tggagaagcg cggcatcatc aagggataca aggccatcat cgaccaa     177
```

<210> SEQ ID NO 11
<211> LENGTH: 141
<212> TYPE: DNA
<213> ORGANISM: Artificial
<220> FEATURE:
<223> OTHER INFORMATION: DNA sequence of signal peptide SP6

<400> SEQUENCE: 11

```
atgaagattg cggttgcagg gactggctac gttggattgt ctgtcgcttt gctgctcgct    60
cagcacaatg aagttcatgc actcgacatc attcccgaga agtcgagca gttaaacaat   120 gggaaaagtc ctattgtcga t                                             141
```

<210> SEQ ID NO 12
<211> LENGTH: 126
<212> TYPE: DNA
<213> ORGANISM: Artificial
<220> FEATURE:
<223> OTHER INFORMATION: DNA sequence of signal peptide SP7

<400> SEQUENCE: 12

```
atgtttgcgt gcgtagcccc gtttgcctct gccgattccg cgcagacgag tgctgtggtg    60
tcctcacgtt ctttcccgaa ggcgagttcg gtgaagaaga atttgttcgc cgaatccacc   120
tccacc                                                              126
```

<210> SEQ ID NO 13
<211> LENGTH: 204
<212> TYPE: DNA
<213> ORGANISM: Artificial
<220> FEATURE:
<223> OTHER INFORMATION: DNA sequence of signal peptide SP8

<400> SEQUENCE: 13

```
atggttggtg acgacaccgt gacgatatgg tcgattgacg aatcccgaca gccgattcgc    60
cgcgttcgtc tgagtcgatt ccccgctggg gcgcgaatat gccttatcat gggttgcatg   120
acacccgcag agcgtgcgag cgcagtcgca tttgcactca agaactgcgc actggaagcg   180
atgacgccgg gcgaggcaac gatg                                          204
```

<210> SEQ ID NO 14
<211> LENGTH: 126
<212> TYPE: DNA
<213> ORGANISM: Artificial
<220> FEATURE:
<223> OTHER INFORMATION: DNA sequence of signal peptide SP9

<400> SEQUENCE: 14

```
atgggcacca tgatgcgaat aggactgacc ggcggcatcg ccgcgggcaa aagtacggtg    60
gcggcgcaac tcaagcaact cggcgcgttg catatcgact acgatgcgct ggcgcatcag   120
```

```
atcgtc                                                               126

<210> SEQ ID NO 15
<211> LENGTH: 153
<212> TYPE: DNA
<213> ORGANISM: Artificial
<220> FEATURE:
<223> OTHER INFORMATION: DNA sequence of signal peptide SP10

<400> SEQUENCE: 15
atgatgactg gtgcacaggc cgctcactgt ggttctgtat ccgcaatttc gctgggactg    60
cccgtttcca cggcgattcc cgaagccaaa ggctcactgc cgaaagcctt gttcgtaggc   120
aaagcgccga tttccggcaa actcaagcag cga                                153

<210> SEQ ID NO 16
<211> LENGTH: 156
<212> TYPE: DNA
<213> ORGANISM: Artificial
<220> FEATURE:
<223> OTHER INFORMATION: DNA sequence of signal peptide SP11

<400> SEQUENCE: 16
atgaagttca ccgttgctaa gaaggccatt gcacttaccg gtgcggttgc catgctgggt    60
tccgttgccg cctgcggttc cgacaccgcc agtggcaagc cggctcaaga taaggacgtt   120
accgaaatca ccgtgtgggc ttgggagccc acgctg                             156

<210> SEQ ID NO 17
<211> LENGTH: 171
<212> TYPE: DNA
<213> ORGANISM: Artificial
<220> FEATURE:
<223> OTHER INFORMATION: DNA sequence of signal peptide SP12

<400> SEQUENCE: 17
atggtgtctt tcaataaact gacccgtact cttgctggca tcgctgccgc cgcgttgatc    60
gttccgctgg ccgcctgtgg tggctccggc aatggtggca ctgccaccgc cgaaggtatc   120
ccggccaagg gcaccgacga tggtaccgag atcaccctgt ggacccgttc c            171

<210> SEQ ID NO 18
<211> LENGTH: 138
<212> TYPE: DNA
<213> ORGANISM: Artificial
<220> FEATURE:
<223> OTHER INFORMATION: DNA sequence of signal peptide SP13

<400> SEQUENCE: 18
atggtcgccg tcctcaggtt cggctgtctg ccatcatgct cggtcttgac tcattattta    60
tccgtgcatg ctgtaggcaa tcggcctgtg gtcggtctcc tcccgcaact tatattgctg   120
tgctgtgcta gcgagtct                                                 138

<210> SEQ ID NO 19
<211> LENGTH: 186
<212> TYPE: DNA
<213> ORGANISM: Artificial
<220> FEATURE:
<223> OTHER INFORMATION: DNA sequence of signal peptide SP14

<400> SEQUENCE: 19
ttgccgggac ctatatgtcc ccggcaacaa cagccgtata tacgctaccg atcagtgctg    60
ccctcatcat ccttggcacc tgccgtggcg gcctcagtct ccttggcgtt ccaccggcg   120
```

```
acggcattcc aaccactcca tccgatgacc actagcaagc acagcgagaa gacaatagtg    180
gcccaa                                                              186

<210> SEQ ID NO 20
<211> LENGTH: 150
<212> TYPE: DNA
<213> ORGANISM: Artificial
<220> FEATURE:
<223> OTHER INFORMATION: DNA sequence of signal peptide SP15

<400> SEQUENCE: 20
atgaaacgta gcgattatat gttggcggca ctcgcctcag ccgtcctgcc gaatctgggg    60
gtggccggcg tacgcgagaa cgtgcaggcc agcgcaaccg acgaggccaa aggcatcgat    120
cagaccgtga ttcaagatgc ctcaggcaag                                    150

<210> SEQ ID NO 21
<211> LENGTH: 135
<212> TYPE: DNA
<213> ORGANISM: Artificial
<220> FEATURE:
<223> OTHER INFORMATION: DNA sequence of signal peptide SP16

<400> SEQUENCE: 21
atgagcaata gtgcatcatc gtttaccggc gtgtccagcg gttataccgc cgggactccg    60
gttccagccg attcacccat ccgtgacaat atcgccgatg ccgttcgccg cgtacgcgag    120
acgactccgt tggcc                                                    135

<210> SEQ ID NO 22
<211> LENGTH: 195
<212> TYPE: DNA
<213> ORGANISM: Artificial
<220> FEATURE:
<223> OTHER INFORMATION: DNA sequence of signal peptide SP19

<400> SEQUENCE: 22
ttggcaagat gggtcactcg gagcgttccg gcaacggcct gtacgtcaac gtgcccggca    60
acaagtacca gccgatcttc gaggccggcg tggaatactt caccgcctga taatcggcgc    120
gtatcgcgtc tgatacggca cacagggaag gaactctcgg gttccttccc ttttttgttc    180
atgccggtca tgggc                                                    195

<210> SEQ ID NO 23
<211> LENGTH: 240
<212> TYPE: DNA
<213> ORGANISM: Artificial
<220> FEATURE:
<223> OTHER INFORMATION: DNA sequence of signal peptide SP21

<400> SEQUENCE: 23
atggcattga ctgatgaaca ggtggagcgg tacgcgcgcc atctgatttt gaagggtgtg    60
ggggtcaaag ggcaaaagcg gttgctggcc tccagcgtgc tcatcatcgg agcgggcggt    120
cttggttctc cggccgccct gtatctggcg gcggccggcg tcggccatat cggactggtg    180
gacggcgatg tggtggatat gagcaatctg caacgccaaa tcatccatac cactgcacgt    240

<210> SEQ ID NO 24
<211> LENGTH: 240
<212> TYPE: DNA
<213> ORGANISM: Artificial
<220> FEATURE:
<223> OTHER INFORMATION: DNA sequence of signal peptide SP22
```

-continued

<400> SEQUENCE: 24
ttggtgtcta tgagaagccc acgcgaggat tttgaggcgg caggcaagcg actgccttgg    60
gatgctgctg ctcgcagtgc agcgctgtcc gccaccgcgc cagtctctga cgtcaaggca   120
tccgccaatg gtgccgacaa tgccagcaac gctgaacatt ccgatgacat gcccaccgtg   180
ccgattcccg cacgcaaggc tgccacgacg ttcgacaccc cctccaagcg tgagcgcatc   240

<210> SEQ ID NO 25
<211> LENGTH: 180
<212> TYPE: DNA
<213> ORGANISM: Artificial
<220> FEATURE:
<223> OTHER INFORMATION: DNA sequence of signal peptide SP23

<400> SEQUENCE: 25
atgaacaagc gatggaacaa actgtgtgtg tccgccctcg cctgcatggc gttggtcgtg    60
ccgttgaccg cctgtgaagg ccaactgccg acgccggctg ctgataccte caccaaggtt   120 gcgccggatt tgaccgaggc gcaggagaag aagattcgtc tgaagattct caagacgatc   180

<210> SEQ ID NO 26
<211> LENGTH: 180
<212> TYPE: DNA
<213> ORGANISM: Artificial
<220> FEATURE:
<223> OTHER INFORMATION: DNA sequence of signal peptide SP24

<400> SEQUENCE: 26
atggtcggca tgcgcgacgt agccaaagcg gcaggggtgt ccttaagcac cgtttcgttg    60
gtggtcaaca acaccggcta cgtctcggcc gatatgcgtg ccaaagtcga gtccgcgatg   120
cgccagctca actacattcc caacgagctg ccccgcaacc tctaccggaa ccgcaccaac   180

<210> SEQ ID NO 27
<211> LENGTH: 180
<212> TYPE: DNA
<213> ORGANISM: Artificial
<220> FEATURE:
<223> OTHER INFORMATION: DNA sequence of signal peptide SP25

<400> SEQUENCE: 27
gtgatgttat ccacaccctc cactacgttg ttttgcctcg cgctgggcag ccccacttca    60
gcaagagatt gcacagcttg cgttagggtg gagaacatga ctatcacagt atccacagac   120
ggttccgcat tagggaatcc aaacgggcca atgggctggg cctgggccga tcatgagcag   180

<210> SEQ ID NO 28
<211> LENGTH: 234
<212> TYPE: DNA
<213> ORGANISM: Artificial
<220> FEATURE:
<223> OTHER INFORMATION: DNA sequence of signal peptide Sec2

<400> SEQUENCE: 28
ttggaacata tgaagatgtt ccggcaccta tcctccgttt ttgctattgc gaccattgcg    60
ccgctggcgt tggcggccac gctagccgtg acgcctgcaa tcgcacaggc cgaccagctg   120
cccaacccgg attgggtggc attgctctcc gactacgaaa agaactattg gcaggccccc   180
gccgatgccg aacacggtgg caaggtgctc gacgccgata caatgaaact cgac          234

<210> SEQ ID NO 29
<211> LENGTH: 441
<212> TYPE: DNA

```
<213> ORGANISM: Artificial
<220> FEATURE:
<223> OTHER INFORMATION: sequence of SP1 with promoter

<400> SEQUENCE: 29
tctcgtgtac gcgaatacgg caaggtagac aaggtggagt accgcgatga tggcatacag    60
cttgaagcgg acgttgatgc ccatcttgcc gctcaggtgg tcgaacagtc cattgactaa   120
cgtgataaac atcacagtat attcgtgagc gctaacaacc gttgaaaaca ttaccatacg   180
gttgtcaaac agggtggtgt gccggtagca aaacgtctta gcgggtttat agagtgaaga   240
cgttagttac aaggcctgcc attcatcagc agaccgcctt tgaagagagg ttcatccatc   300
atggcggaaa ctaccgttaa gcccacgaag cttgctgtta ttggtgccgg tgccgttggc   360
tccaccctcg ccttcgccgc tgcccagcgt ggcatcgctc gcgagatcgt gcttgaagac   420
atcgccaagg agcgcgtgga a                                             441

<210> SEQ ID NO 30
<211> LENGTH: 456
<212> TYPE: DNA
<213> ORGANISM: Artificial
<220> FEATURE:
<223> OTHER INFORMATION: sequence of SP2 with promoter

<400> SEQUENCE: 30
cgcgctgcaa tggcgtcggc cgcgctgcat gaacgcgtgt gaaatggtat gggctgccgc    60
attttgccca atattgaatc acgcgctccg cagcacacga tcgacgtggg ccacgacctg   120
gaacaactcg gcggcgtgct tgagcagact gatgcgcacc cagccttcgc ccgcctgacc   180
gaagcagacc cccggcatca gcgccacgtc cagcgcgccc ggagtctcca gcaggctcag   240
cgagcgcacg ccgccgaatt cgagcccgcc ataggcgaaa tcatcgcggc atggcagaat   300
gtgggtatga ctgagaacgc cgtaaatact gccgtgactt ccacctcctc tcccgcaatt   360
cccgccgaga cttccgccgt ctcccccgca actcgcgcag ccaaccgccc gctgggcaca   420
ccgctgggca agcaccccac ccgcgtgctg tttttg                              456

<210> SEQ ID NO 31
<211> LENGTH: 465
<212> TYPE: DNA
<213> ORGANISM: Artificial
<220> FEATURE:
<223> OTHER INFORMATION: sequence of SP3 with promoter

<400> SEQUENCE: 31
ggcgtctggc agcgcacagt gccaggccag ggcgatgcgc tggtctcctg tgtggtcagt    60
ccgggattcg tattcgacgg cttcacactc gaacagtgaa cgccatttcg ctctgcgcca   120
atatgagata tccgtccgct tacgcgccag attgcgcggc tctagtcggc cataagcaat   180
ggcgatagcc agcatccgaa aatatcgatg ttttgtaacc caatagccat acaattggcg   240
cgaatgcatc aagcacggtt tgaaccgtgt gcatgacgag cacttgagga gaggaaaccc   300
atgttcaata agcgacacat cgtccgtacc attgcggcca ccgccagcat cctggctctg   360
tcgttcaccg cagcctgcgg ttccggccag tccaccgcat ccaattccac cgattcggac   420
gacatcaccc agcagacgta caagccgggc aagctgacca tcgcc                   465

<210> SEQ ID NO 32
<211> LENGTH: 495
<212> TYPE: DNA
<213> ORGANISM: Artificial
<220> FEATURE:
```

<223> OTHER INFORMATION: sequence of SP4 with promoter

<400> SEQUENCE: 32

| | | | | | |
|---|---|---|---|---|---|
| atcagaggag | ccggtgcttc | cgccatcccc | ggcagaagtg | gaaccgcagg cagctacaga | 60 |
| ggagagcacg | gccacagcac | caatcagggc | aattgtcttc | ttgccgaact tcatcgttct | 120 |
| ttccttcctt | gttatgggaa | acgacgggac | ttggcgtttt | gttccaagcc ttgtatcgtt | 180 |
| tcaaagaaac | ggtaccacat | gttttatgtt | tacgcaaaca | cgacacgtcg caccatagtg | 240 |
| actaaccaca | aaccgaaacc | atagtgacta | accgcaaacc | gaaggagatg catcccgctc | 300 |
| atgaccactc | acaacagcca | gtattccgcc | gaaaccgccc | atcccgacaa gcaggaaagc | 360 |
| agcccggcgc | cgaccgccgc | cggcaccacg | gccagtaacg | tctccacaac tggcaacgca | 420 |
| accacgccgg | acgccagcat | cgccctcaac | gccgacgcca | ctccggtagc cgacgttccc | 480 |
| ccgcgtctgt | tcggc | | | | 495 |

<210> SEQ ID NO 33
<211> LENGTH: 477
<212> TYPE: DNA
<213> ORGANISM: Artificial
<220> FEATURE:
<223> OTHER INFORMATION: sequence of SP5 with promoter

<400> SEQUENCE: 33

| | | | | | |
|---|---|---|---|---|---|
| ctcgcgggct | tggcggtcgg | cacagcaacc | cgtctggcag | caggcacagc agcagatgca | 60 |
| acttcggaca | gaggcatgtt | ggaaaacttc | tgcatatcat | ccctcctcaa tggaattatt | 120 |
| tcgtcgttct | cttatttcag | aaggaattat | tacattcaat | taggacttta ggcataaaca | 180 |
| ttccaccaca | caacagaaaa | cacaggaaga | actactgaaa | ttaccaggca aaatcggaaa | 240 |
| gccatcgcat | tccggcaaca | ggtacagtga | acacagagca | caacgaacgg agaagacacc | 300 |
| atgaccgcga | ttgacgagac | cgaccagcgc | atcctcacca | tgctggaggc cgacggccgc | 360 |
| gccacgctcg | cgcaactggc | ccaggcgacc | ggactgtccg | tctccgccgc ccagtcgcgc | 420 |
| gtgcagaagc | tggagaagcg | cggcatcatc | aagggataca | aggccatcat cgaccaa | 477 |

<210> SEQ ID NO 34
<211> LENGTH: 441
<212> TYPE: DNA
<213> ORGANISM: Artificial
<220> FEATURE:
<223> OTHER INFORMATION: sequence of SP6 with promoter

<400> SEQUENCE: 34

| | | | | | |
|---|---|---|---|---|---|
| gttcgggtcc | gggtgcggac | gccatcttgc | gtccgtgcga | gcttttcgtg cctcttctgt | 60 |
| ccttggaagc | tgacgtgttt | tgattttcac | gaatgacgcg | ataattacgt tttcgggatg | 120 |
| ctccttagcc | gtattcgctc | gtcgttctgc | aagacccatc | aagaaatgtg cattggttac | 180 |
| cggttcgccc | gtacaggatg | aacgtcggca | tgtgcgattt | ggaagatgct ggctacgttg | 240 |
| attcgttgca | gtgacctgcg | tctacaatat | cttaggattg | cgtaaggaaa ggctgacact | 300 |
| atgaagattg | cggttgcagg | gactggctac | gttggattgt | ctgtcgcttt gctgctcgct | 360 |
| cagcacaatg | aagttcatgc | actcgacatc | attcccgaga | agtcgagca gttaaacaat | 420 |
| gggaaaagtc | ctattgtcga | t | | | 441 |

<210> SEQ ID NO 35
<211> LENGTH: 426
<212> TYPE: DNA
<213> ORGANISM: Artificial
<220> FEATURE:

<223> OTHER INFORMATION: sequence of SP7 with promoter

<400> SEQUENCE: 35

```
aggcggtcca tggtggatgg aatggctata gcgtggctct cgctagtgcc atgaccgaaa      60
agctcaccat cgtggtgcgt atcccgtgat gcagtcttat tgattgattt attgcaggcc     120
tcggatgccg atcggtatcc gaggcctgtt gcgttctcct gccgaatgat gcacccgcga     180
catcatcttc gaaatgctat tcctgttatg aaatcgaccc atgtgtgcta gtgtatggcg     240
ttgatgatga gcgttaagac tattatttcc acatcagtgg cgattatcgc cacgggtgcc     300
atgtttgcgt gcgtagcccc gtttgcctct gccgattccg cgcagacgag tgctgtggtg     360
tcctcacgtt ctttcccgaa ggcgagttcg gtgaagaaga atttgttcgc cgaatccacc     420
tccacc                                                                426
```

<210> SEQ ID NO 36
<211> LENGTH: 504
<212> TYPE: DNA
<213> ORGANISM: Artificial
<220> FEATURE:
<223> OTHER INFORMATION: sequence of SP8 with promoter

<400> SEQUENCE: 36

```
aaccattcgg acgcgcagaa cagtacggcg agcacgagca gcaggaagca caaaccgtca      60
cgacggtagg ctggatcgta ttcgccgacg ccggtgacgg cgcgtacgcc ggagccgaac     120
gcgcgcggaa tcgcgagcag gatcttcttc cacaacggct caggttcgag gtcaagctcg     180
ggctggacct tggtttcgcc atcatgggta gacccgttgt ctttggattt acggggtttg     240
gtgctgttgg aggatgctgt tcgtgccata tcgggtctga ttctactagt acggggggtgc     300
atggttggtg acgacaccgt gacgatatgg tcgattgacg aatcccgaca gccgattcgc     360
cgcgttcgtc tgagtcgatt ccccgctggg gcgcgaatat gccttatcat gggttgcatg     420
acacccgcag agcgtgcgag cgcagtcgca tttgcactca agaactgcgc actggaagcg     480
atgacgccgg gcgaggcaac gatg                                            504
```

<210> SEQ ID NO 37
<211> LENGTH: 426
<212> TYPE: DNA
<213> ORGANISM: Artificial
<220> FEATURE:
<223> OTHER INFORMATION: sequence of SP9 with promoter

<400> SEQUENCE: 37

```
ccagggcccg aaggaagaga agccggtcga ggagacctcc aactactctt ccgctgctcc      60
ggctaccggt accctcgccg actccgatca gctcgccgcc ctgcgcgacc agctgctcgg     120
caagtgagtt tgccgcgaag ctagcgctta gcgtgtaaag aaacccggtc cgattgggcc     180
gggtttcttg tgttttttgga gttatccgcc aatgactccc ctcagtctcg ctacgcgagc     240
cggctcccct ccctgagggg agctgtcggc gatagccggc cgagggagc gccagctatc      300
atgggcacca tgatgcgaat aggactgacc ggcggcatcg ccgcgggcaa agtacggtg      360
gcggcgcaac tcaagcaact cggcgcgttg catatcgact acgatgcgct ggcgcatcag     420
atcgtc                                                                426
```

<210> SEQ ID NO 38
<211> LENGTH: 453
<212> TYPE: DNA
<213> ORGANISM: Artificial
<220> FEATURE:

<223> OTHER INFORMATION: sequence of SP10 with promoter

<400> SEQUENCE: 38

| cagcccatcg ctatggagga aggcctgacc ttcgctgtgc gtgaaggtgg ccacaccgtc | 60 |
| ggctccggtc gtgtgaccaa gatcctcgcc tgatttcat cagacaagaa tcttcgcttg | 120 |
| aactagcgtt atagaaaatc cccttcgagg aaactcggag gggattttct ataaccgcaa | 180 |
| caggatatgg atatgtacca cgacttccgg cctggatgcg ctagtgttgc tttccaatag | 240 |
| ataaacggac tgctgcactg cgaggatatg acactgatgg caggccggga agaaggtcg | 300 |
| atgatgactg gtgcacaggc cgctcactgt ggttctgtat ccgcaatttc gctgggactg | 360 |
| cccgtttcca cggcgattcc cgaagccaaa ggctcactgc cgaaagcctt gttcgtaggc | 420 |
| aaagcgccga tttccggcaa actcaagcag cga | 453 |

<210> SEQ ID NO 39
<211> LENGTH: 456
<212> TYPE: DNA
<213> ORGANISM: Artificial
<220> FEATURE:
<223> OTHER INFORMATION: sequence of SP11 with promoter

<400> SEQUENCE: 39

| tctgtagcgg gaggttgcga taacaggatc gggcactctt cggagcgccc gattttctta | 60 |
| tgccatggga gcagtggcgc gcggattgcg ataccaagat ggcgtgttgc cgaagaatgt | 120 |
| gtataataaa agatgttatc gcaaccatag ctacaaagtg gcgaaacaaa gccgttttgt | 180 |
| gactactgaa ccatagagtg atggttcacg atagcatgac gacgaggaga gttgccatgc | 240 |
| tgttgtggtg acaatcactg cagaccgccg aaaggcgatc caaggaagga gaacagaacg | 300 |
| atgaagttca ccgttgctaa gaaggccatt gcacttaccg gtgcggttgc catgctgggt | 360 |
| tccgttgccg cctgcggttc cgacaccgcc agtggcaagc cggctcaaga taaggacgtt | 420 |
| accgaaatca ccgtgtgggc ttgggagccc acgctg | 456 |

<210> SEQ ID NO 40
<211> LENGTH: 471
<212> TYPE: DNA
<213> ORGANISM: Artificial
<220> FEATURE:
<223> OTHER INFORMATION: sequence of SP12 with promoter

<400> SEQUENCE: 40

| gcgttacttc catgttcgct tttgtttgat ttgctcgaca cgccggaata atcattgata | 60 |
| ttaagccaat tcaagcacgt tattcatagt cgaatcacag tctcgaaccc gtttgatgtg | 120 |
| agaaaaaacg cgaaaatgcg aaagcgcttt tgcaaaaact tccatgttcg tttatattga | 180 |
| gaaaaggctt tcgcagtgtt acctgctccg ggcaaaggag cgagcagggc gaaaccaagg | 240 |
| aggcggaccg tccgccaccg cctctcatag ttgagcggat atatagagaa agaagcgaac | 300 |
| atggtgtctt tcaataaact gacccgtact cttgctggca tcgctgccgc gcgttgatc | 360 |
| gttccgctgg ccgcctgtgg tggctccggc aatggtggca ctgccaccgc cgaaggtatc | 420 |
| ccggccaagg gcaccgacga tggtaccgag atcaccctgt ggacccgttc c | 471 |

<210> SEQ ID NO 41
<211> LENGTH: 438
<212> TYPE: DNA
<213> ORGANISM: Artificial
<220> FEATURE:
<223> OTHER INFORMATION: sequence of SP13 with promoter

<400> SEQUENCE: 41

```
ccttctcaac gccagcggcc ttcttcagca gagctgcagc cggcggggtc ttgagcacga      60
aggtgaagga acgatcttcg taaacggtga tctcgacagg gatgacctga cccatcttgt     120
cctgcgtctg ggcattgtat gccttgcaga agtccatgat gttcacgcca tgcgaaccca     180
gagccgggcc cagcggcggg gccgggttgg ccttgccagc ctggatctgg agcttaatca     240
gcgccgagac tttcttcttg ggagccatat tatggttctt cttctataa cgcggttcga     300
atggtcgccg tcctcaggtt cggctgtctg ccatcatgct cggtcttgac tcattattta     360
tccgtgcatg ctgtaggcaa tcggcctgtg gtcggtctcc tcccgcaact tatattgctg     420
tgctgtgcta gcgagtct                                                   438
```

<210> SEQ ID NO 42
<211> LENGTH: 486
<212> TYPE: DNA
<213> ORGANISM: Artificial
<220> FEATURE:
<223> OTHER INFORMATION: sequence of SP14 with promoter

<400> SEQUENCE: 42

```
gacatagcgc ggtttcatac ctttcggcaa tgccggcatc agttcggtga tggtcttggc      60
cttccagcag acatccagga ggctccgcac ctcattcacc ggaagcaagc cggtcttggt     120
atcggttcgg gaatcgcaca tcgctggccc aacctccaat tagttaccaa tagtcattac     180
cataagtaac tatatgcagg ctctagacaa acccaacggc ctgcgcgccc gtgtcgagtt     240
ccgtttcgac ataaaaaagc cagggaatcc ctggcttgca atgcacatat cgctgcagat     300
ttgccgggac ctatatgtcc ccggcaacaa cagccgtata tacgctaccg atcagtgctg     360
ccctcatcat ccttggcacc tgccgtggcg gcctcagtct ccttggcgtt ccacccggcg     420
acggcattcc aaccactcca tccgatgacc actagcaagc acagcgagaa gacaatagtg     480
gcccaa                                                                486
```

<210> SEQ ID NO 43
<211> LENGTH: 400
<212> TYPE: DNA
<213> ORGANISM: Artificial
<220> FEATURE:
<223> OTHER INFORMATION: sequence of SP15 with promoter

<400> SEQUENCE: 43

```
accggcacct gcgccggcga taatgcgcac cggcccttgc aacgtagtcg cggcggtacg      60
ctgccgctca tcgagcccct caagaatccc ctgcgcctgt tccatgcgtc cattgtggca     120
cgattcgcgc tcacggcacg actcatgcct atggctgaat cgggctcacg acaaaacatc     180
gccagaatca tgcgttttgc gtgtcattct gcggtgcgaa tcgccacgga tgtattagtg     240
tggaagggtg atgaaacgta gcgattatat gttggcggca ctcgcctcag ccgtcctgcc     300
gaatctgggg gtggccggcg tacgcgagaa cgtgcaggcc agcgcaaccg acgaggccaa     360
aggcatcgat cagaccgtga ttcaagatgc ctcaggcaag                           400
```

<210> SEQ ID NO 44
<211> LENGTH: 435
<212> TYPE: DNA
<213> ORGANISM: Artificial
<220> FEATURE:
<223> OTHER INFORMATION: sequence of SP16 with promoter

<400> SEQUENCE: 44

```
atcgcaacac ctccatattg ttcctgttgt tttacccttc ccgaatttgt gccactgaca      60
tcgcgtcagc gtcacaaatt cgggagatgt tgctcggcgg aggcgtctat gtatcacgaa     120
tggacgggga cgcgccagac ctgacgacac gtatcgaaca aatccgtcac gataatgtcc     180
atgttggcgc atagcgtcgg cactgtaatg caggggaact cgcatgtggt tcgcgagttg     240
agaaaggcct gagcctgacc cttagaacct gttggttaag accatcgtag ggagcagtaa     300
atgagcaata gtgcatcatc gtttaccggc gtgtccagcg gttataccgc cgggactccg     360
gttccagccg attcacccat ccgtgacaat atcgccgatg ccgttcgccg cgtacgcgag     420
acgactccgt tggcc                                                       435

<210> SEQ ID NO 45
<211> LENGTH: 361
<212> TYPE: DNA
<213> ORGANISM: Artificial
<220> FEATURE:
<223> OTHER INFORMATION: sequence of HU promoter

<400> SEQUENCE: 45
gtcttcctgc tggcctatgc attgggttcc gcagtgccca ctccaggcgg tctgggcggt      60
gtggaagcgg cgctgacatt cgcgttcgtg gcggtcggag tgccgcaggg cgtggcgctt     120
tccgccactt tgctgcaccg cgtggtgttc tactggctgc gcattccgct gggcgcggcg     180
gccatgaagt ggcttgacaa gcataatctt gtctgattcg tctattttca tacccccttc     240
ggggaaatag atgtgaaaac ccttataaaa cgcgggtttt cgcagaaaca tgcgctagta     300
tcattgatga caacatggac taagcaaaag tgcttgtccc ctgacccaag aaggatgctt     360
t                                                                      361

<210> SEQ ID NO 46
<211> LENGTH: 114
<212> TYPE: DNA
<213> ORGANISM: Artificial
<220> FEATURE:
<223> OTHER INFORMATION: sequence of Hu terminator

<400> SEQUENCE: 46
ccttctgctc gtagcgatta cttcgagcat tactgacgac aaagaccccg accgagatgg      60
tcggggtctt tttgttgtgg tgctgtgacg tgttgtccaa ccgtattatt ccgg           114

<210> SEQ ID NO 47
<211> LENGTH: 166
<212> TYPE: PRT
<213> ORGANISM: Artificial Sequence
<220> FEATURE:
<223> OTHER INFORMATION: amino acid sequence of mature human IL18mut-His

<400> SEQUENCE: 47

Met Tyr Phe Gly Lys Leu Ala Ser Lys Leu Ser Val Ile Arg Asn Leu
1               5                   10                  15

Asn Asp Gln Val Leu Phe Ile Asp Gln Gly Asn Arg Pro Leu Phe Glu
            20                  25                  30

Asp Met Thr Asp Ser Asp Cys Arg Asp Asn Ala Pro Arg Thr Ile Phe
        35                  40                  45

Ile Ile Ser Met Tyr Ala Asp Ser Gln Pro Arg Gly Met Ala Val Thr
    50                  55                  60

Ile Ser Val Lys Cys Glu Lys Ile Ser Thr Leu Ser Cys Glu Asn Lys
65                  70                  75                  80

Ile Ile Ser Phe Lys Glu Met Asn Pro Pro Asp Asn Ile Lys Asp Thr
```

```
                     85                  90                  95
Lys Ser Asp Ile Ile Phe Phe Gln Arg Ser Val Pro Gly His Asp Asn
            100                 105                 110

Lys Met Gln Phe Glu Ser Ser Ser Tyr Glu Gly Tyr Phe Leu Ala Cys
            115                 120                 125

Glu Lys Glu Arg Asp Leu Phe Lys Leu Ile Leu Lys Lys Glu Asp Glu
            130                 135                 140

Leu Gly Asp Arg Ser Ile Met Phe Thr Val Gln Asn Glu Asp Leu Gln
145                 150                 155                 160

His His His His His His
            165

<210> SEQ ID NO 48
<211> LENGTH: 4346
<212> TYPE: DNA
<213> ORGANISM: Artificial Sequence
<220> FEATURE:
<223> OTHER INFORMATION: DNA sequence of phIL18mut-His

<400> SEQUENCE: 48
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg tgttctact ggctgcgcat tccgctgggc      180
gcggcggcca tgaagtggct tgacaagcat aatcttgtct gattcgtcta ttttcatacc     240
cccttcgggg aaatagatgt gaaaacccctt ataaaacgcg gttttcgca gaaacatgcg     300
ctagtatcat tgatgacaac atggactaag caaaagtgct tgtcccctga cccaagaagg     360
aacgcgtatg tacttcggca agctggcctc caagctgtcc gtgatccgta acctgaacga     420
ccaggtgctg ttcatcgacc agggcaaccg tccgctgttc aagatatga ccgactccga      480
ttgccgcgac aacgccccgc gtaccatctt catcatctcg atgtacgccg attcccagcc     540
gcgtggcatg ccgtgacca tctccgtcaa gtgcgagaag atcagcaccc tgagctgcga      600
aaacaagatc atctccttca aggagatgaa cccgccggac aacatcaagg ataccaagag     660
cgacatcatc ttcttccagc gctccgtgcc gggccacgac aacaagatgc agttcgagtc     720
cagctcgtac gaaggctact cctggcctg cgagaaggaa cgcgacctgt tcaagctgat      780
cctgaagaag gaagacgaac tgggcgaccg tagcatcatg ttcaccgtcc agaacgagga     840
tctgcagcat catcatcatc atcattgatg accttctgct cgtagcgatt acttcgagca     900
ttactgacga caaagacccc gaccgagatg gtcgggtctc tttgttgtg gtgctgtgac      960
gtgttgtcca accgtattat tccggactag tcctccagga cctcgtctac gaggcgctga    1020
gcgaggaatg gcgcaaaagg gacggcgaga tcagcgaccc atgggccaac gacgaggcgg    1080
acggatacca gccgccctca tacgagccgg tcaaccccga acgcaggact ccccagacgc    1140
cctccgatgg cctgatctga cgtccgaaaa aaggcgctgt gcgccctttt taaatctttt    1200
ataaatcttt ttacattctt ttagcccctc cgcagcctta ctctcccaac gggtttcagc    1260
cgaaacctac accaaaaggg gagcgaacct acaccaaaag gggagcgaac ctacaccaaa    1320
aggggagcga acctacacca aaaggggagc tatatacacc ttttgttatt taaggtgcaa    1380
gttgtgctat gctgaggcca tgtccaatga gatcgtgaag ttcagcaacc agttcaacaa    1440
cgtcgcgctg aagaagttcg acgccgtgca cctggacgtg ctcatggcga tcgcctcaag    1500
ggtgagggag aagggcacgg ccacggtgga gttctcgttc gaggagctgc gcggcctcat    1560
gcgattgagg aagaacctga ccaacaagca gctggccgac aagatcgtgc agacgaacgc    1620
```

```
gcgcctgctg gcgctgaact acatgttcga ggattcgggc aagatcatcc agttcgcgct   1680
gttcacgaag ttcgtcaccg acccgcagga ggcgactctc gcggttgggg tcaacgagga   1740
gttcgcgttc ctgctcaacg acctgaccag ccagttcacg cgcttcgagc tggccgagtt   1800
cgccgacctc aagagcaagt acgccaagga gttctaccgc agggccaagc agtaccgcag   1860
ctccggaatc tggaagatcg gccgcgacga gttctgccga ctgcttggcg ttccaccgtc   1920
ggcaataacc cagacacgat atctgaatca gaaggttctt cagccaattc aggaggagtg   1980
tgggcctctc cttggcctga agatcgagcg ccagtacgtg aaacgcaggc tgtcgggctt   2040
cgtgttcaca ttcgcccgcg agacccctcc ggtgatcgac gccaggcccg tggaggcgag   2100
gaagacggac ggcgacggca agggccattg acgagcgtt gccgggtacg gcgaggtgtt   2160
cacgaccacg gcgttgttcg acgtgacggc cgcccgggct cacttcgacg gcaccgttga   2220
agccggggag tgccgtttct gcgcgtttga cgcgcgcaac cgcgaacatc atgcgcggaa   2280
cgccggaagg ctgttctagc ggccgtgtcc gcgcctctgg ggcggttgcg cctgccatgg   2340
gtcgatctgc cgctgttcgg cctcacgctg gtctgtgcgc tgcctgatct ccctgagcag   2400
gtcggccttg gtcctggggg cgcttcgctc ctcgaacggg ccgctctccc ccaggtcctc   2460
gggctcgctc aggtccaacg gctcgtcacc ggacggctcg ggccggttct ctccctgtgc   2520
cgggttctcc gcctgtgcgc gttgttcggc catgcgcagt gcgagggcct tcacctgttc   2580
ggggcttgtc gactcgattt tcgttcgtga atacatgtta taataactat aactaataac   2640
gtaacgtgac tggcaagaga tattttaaa caatgaata ggtttacact tactttagtt    2700
ttatggaaat gaaagatcat atcatatata atctagaata aaattaacta aataattat    2760
tatctagata aaaaatttag aagccaatga aatctataaa taaactaaat taagtttatt   2820
taattaacaa ctatggatat aaaataggta ctaatcaaaa tagtgaggag gatatatttg   2880
aatacatacg aacaaattaa taaagtgaaa aaaatacttc ggaaacattt aaaaaataac   2940
cttattggta cttacatgtt tggatcagga gttgagagtg gactaaaacc aaatagtgat   3000
cttgactttt tagtcgtcgt atctgaacca ttgacagatc aaagtaaaga aatacttata   3060
caaaaaatta gacctatttc aaaaaaaata ggagataaaa gcaacttacg atatattgaa   3120
ttaacaatta ttattcagca agaaatggta ccgtggaatc atcctcccaa acaagaattt   3180
atttatggag aatggttaca agagctttat gaacaaggat acattcctca gaaggaatta   3240
aattcagatt taaccataat gctttaccaa gcaaaacgaa aaaataaaag aatatacgga   3300
aattatgact tagaggaatt actacctgat attccatttt ctgatgtgag aagagccatt   3360
atggattcgt cagaggaatt aatagataat tatcaggatg atgaaaccaa ctctatatta   3420
actttatgcc gtatgatttt aactatggac acgggtaaaa tcataccaaa agatattgcg   3480
ggaaatgcag tggctgaatc ttctccatta gaacataggg agagaatttt gttagcagtt   3540
cgtagttatc ttggagagaa tattgaatgg actaatgaaa atgtaaattt aactataaac   3600
tatttaaata acagattaaa aaaattataa aaaaattgaa aaaatggtgg aaacactttt   3660
ttcaattttt ttagatcttg agcaaaaggc cagcaaaagg ccaggaaccg taaaaaggcc   3720
gcgttgctgg cgttttttcca taggctccgc cccctgacg agcatcacaa aaatcgacgc   3780
tcaagtcaga ggtggcgaaa cccgacagga ctataaagat accaggcgtt tcccctgga   3840
agctccctcg tgcgctctcc tgttccgacc ctgccgctta ccggatacct gtccgccttt   3900
ctcccttcgg gaagcgtggc gctttctcat agctcacgct gtaggtatct cagttcggtg   3960
taggtcgttc gctccaagct gggctgtgtg cacgaacccc ccgttcagcc cgaccgctgc   4020
```

```
gccttatccg gtaactatcg tcttgagtcc aacccggtaa gacacgactt atcgccactg    4080
gcagcagcca ctggtaacag gattagcaga gcgaggtatg taggcggtgc tacagagttc    4140
ttgaagtggt ggcctaacta cggctacact agaagaacag tatttggtat ctgcgctctg    4200
ctgaagccag ttaccttcgg aaaaagagtt ggtagctctt gatccggcaa acaaaccacc    4260
gctggtagcg gtggtttttt tgtttgcaag cagcagatta cgcgcagaaa aaaggatct    4320 caagaagatc ctttgatctt ttctac                                         4346

<210> SEQ ID NO 49
<211> LENGTH: 4484
<212> TYPE: DNA
<213> ORGANISM: Artificial Sequence
<220> FEATURE:
<223> OTHER INFORMATION: DNA sequence of pSP3B-hIL18mut

<400> SEQUENCE: 49
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaaccctt ataaaacgcg ggttttcgca gaaacatgcg     300
ctagtatcat tgatgacaac atggactaag caaaagtgct tgtcccctga cccaagaagg     360
atgctttatg ttcaataagc gacacatcgt ccgtaccatt gcggccaccg ccagcatcct     420
ggctctgtcg ttcaccgcag cctgcggttc cggccagtcc accgcatcca attccaccga     480
ttcggacgac atcacccagc agacgtacaa gccgggcaag ctgaccatcg cctacttcgg     540
caagctggcc tccaagctgt ccgtgatccg taacctgaac gaccaggtgc tgttcatcga     600
ccagggcaac cgtccgctgt tcgaagatat gaccgactcc gattgccgcg caacgccccc     660
gcgtaccatc ttcatcatct cgatgtacgc cgattcccag ccgcgtggca tggccgtgac     720
catctccgtc aagtgcgaga agatcagcac cctgagctgc gaaaacaaga tcatctcctt     780
caaggagatg aacccgccgg acaacatcaa ggataccaag agcgacatca tcttcttcca     840
gcgctccgtg ccgggccacg acaacaagat gcagttcgag tccagctcgt acgaaggcta     900
cttcctggcc tgcgagaagg aacgcgacct gttcaagctg atcctgaaga aggaagacga     960
actgggcgac cgtagcatca tgttcaccgt ccagaacgag gattgatgac cttctgctcg    1020
tagcgattac ttcgagcatt actgacgaca aagaccccga ccgagatggt cggggtcttt    1080
ttgttgtggt gctgtgacgt gttgtccaac cgtattattc cggactagtc ctccaggacc    1140
tcgtctacga ggcgctgagc gaggaatggc gcaaagggga cggcgagatc agcgacccat    1200
gggccaacga cgaggcggac ggataccagc cgccctcata cgagccggtc aaccccgaac    1260
gcaggactcc ccagacgccc tccgatggcc tgatctgacg tccgaaaaaa ggcgctgtgc    1320
gcccttttta aatctttat aaatcttttt acattctttt agcccctccg cagccttact    1380
ctcccaacgg gtttcagccg aaacctacac caaaagggga gcgaacctac accaaaaggg    1440
gagcgaacct acaccaaaag gggagcgaac ctacaccaaa aggggagcta tatacacctt    1500
tgttatttta aggtgcaagt tgtgctatgc tgaggccatg tccaatgaga tcgtgaagtt    1560
cagcaaccag ttcaacaacg tcgcgctgaa gaagttcgac gccgtgcacc tggacgtgct    1620 catgcgatc gcctcaaggg tgaggagaa gggcacggcc acgtggagt tctcgttcga    1680 ggagctgcgc ggcctcatgc gattgaggaa gaacctgacc aacaagcagc tggccgacaa    1740
```

```
gatcgtgcag acgaacgcgc gcctgctggc gctgaactac atgttcgagg attcgggcaa      1800
gatcatccag ttcgcgctgt tcacgaagtt cgtcaccgac ccgcaggagg cgactctcgc      1860
ggttggggtc aacgaggagt tcgcgttcct gctcaacgac ctgaccagcc agttcacgcg      1920
cttcgagctg gccgagttcg ccgacctcaa gagcaagtac gccaaggagt tctaccgcag      1980
ggccaagcag taccgcagct ccggaatctg gaagatcggc cgcgacgagt tctgccgact      2040
gcttggcgtt ccaccgtcgg caataaccca gacacgatat ctgaatcaga aggttcttca      2100
gccaattcag gaggagtgtg ggcctctcct tggcctgaag atcgagcgcc agtacgtgaa      2160
acgcaggctg tcgggcttcg tgttcacatt cgcccgcgag acccctccgg tgatcgacgc      2220
caggcccgtg gaggcgagga agacggacgg cgacggcaag ggccattgga cgagcgttgc      2280
cgggtacggc gaggtgttca cgaccacggc gttgttcgac gtgacggccg cccgggctca      2340
cttcgacggc accgttgaag ccggggagtg ccgtttctgc gcgtttgacg cgcgcaaccg      2400
cgaacatcat gcgcggaacg ccggaaggct gttctagcgg ccgtgtccgc gcctctgggg      2460
cggttgcgcc tgccatgggt cgatctgccg ctgttcggcc tcacgctggt ctgtgcgctg      2520
cctgatctcc ctgagcaggt cggccttggt cctgggggcg cttcgctcct cgaacgggcc      2580
gctctccccc aggtcctcgg gctcgctcag gtccaacggc tcgtcaccgg acggctcggg      2640
ccggttctct cccgtgccg ggtctccgc ctgtgcgcgt tgttcggcca tgcgcagtgc      2700
gagggccttc acctgttcgg ggcttgtcga ctcgattttc gttcgtgaat acatgttata      2760
ataactataa ctaataacgt aacgtgactg gcaagagata ttttaaaac aatgaatagg      2820
tttacactta ctttagtttt atggaaatga aagatcatat catatataat ctagaataaa      2880
attaactaaa ataattatta tctagataaa aaatttagaa gccaatgaaa tctataaata      2940
aactaaatta agtttattta attaacaact atggatataa aataggtact aatcaaaata      3000
gtgaggagga tatatttgaa tacatacgaa caaattaata aagtgaaaaa atacttcgg      3060
aaacatttaa aaaataacct tattggtact tacatgtttg gatcaggagt tgagagtgga      3120
ctaaaaccaa atagtgatct tgactttta gtcgtcgtat ctgaaccatt gacagatcaa      3180
agtaaagaaa tacttataca aaaaattaga cctatttcaa aaaaaatagg agataaaagc      3240
aacttacgat atattgaatt aacaattatt attcagcaag aaatggtacc gtggaatcat      3300
cctcccaaac aagaatttat ttatggagaa tggttacaag agctttatga acaaggatac      3360
attcctcaga aggaattaaa ttcagattta accataatgc tttaccaagc aaaacgaaaa      3420
aataaaagaa tatacggaaa ttatgactta gaggaattac tacctgatat tccattttct      3480
gatgtgagaa gagccattat ggattcgtca gaggaattaa tagataatta tcaggatgat      3540
gaaaccaact ctatattaac tttatgccgt atgatttta ctatggacac gggtaaaatc      3600
ataccaaaag atattgcggg aaatgcagtg gctgaatctt ctccattaga acataggag      3660
agaatttgt tagcagttcg tagttatctt ggagagaata ttgaatggac taatgaaaat      3720
gtaaatttaa ctataaacta tttaaataac agattaaaaa aattataaaa aaattgaaaa      3780
aatggtggaa acacttttt caattttttt agatcttgag caaaaggcca gcaaaaggcc      3840
aggaaccgta aaaaggccgc gttgctggcg tttttccata ggctccgccc ccctgacgag      3900
catcacaaaa atcgacgctc aagtcagagg tggcgaaacc cgacaggact ataaagatac      3960
caggcgtttc ccctggaag ctccctcgtg cgctctcctg ttccgaccct gccgcttacc      4020
ggatacctgt ccgcctttct cccttcggga agcgtggcgc tttctcatag ctcacgctgt      4080
aggtatctca gttcggtgta ggtcgttcgc tccaagctgg gctgtgtgca cgaaccccc      4140
```

```
gttcagcccg accgctgcgc cttatccggt aactatcgtc ttgagtccaa cccggtaaga   4200
cacgacttat cgccactggc agcagccact ggtaacagga ttagcagagc gaggtatgta   4260
ggcggtgcta cagagttctt gaagtggtgg cctaactacg gctacactag aagaacagta   4320
tttggtatct gcgctctgct gaagccagtt accttcggaa aaagagttgg tagctcttga   4380
tccggcaaac aaaccaccgc tggtagcggt ggttttttttg tttgcaagca gcagattacg   4440
cgcagaaaaa aaggatctca agaagatcct ttgatctttt ctac                    4484

<210> SEQ ID NO 50
<211> LENGTH: 3863
<212> TYPE: DNA
<213> ORGANISM: Artificial Sequence
<220> FEATURE:
<223> OTHER INFORMATION: DNA sequence of pBEshuttle

<400> SEQUENCE: 50
ggatccgtct tcctgctggc ctatgcattg ggttccgcag tgcccactcc aggcggtctg     60
ggcggtgtgg aagcggcgct gacattcgcg ttcgtggcgg tcggagtgcc gcagggcgtg    120
gcgctttccg ccactttgct gcaccgcgtg gtgttctact ggctgcgcat tccgctgggc    180
gcggcggcca tgaagtggct tgacaagcat aatcttgtct gattcgtcta ttttcatacc    240 ccctttcgggg aaatagatgt gaaaacccctt ataaaacgcg ggttttcgca gaaacatgcg   300
ctagtatcat tgatgacaac atggactaag caaaagtgct tgtcccctga cccaagaagg    360
atgctttatg aagcttatcc tgcagtgacc ttctgctcgt agcgattact cgagcatta    420 ctgacgacaa agaccccgac cgagatggtc ggggtctttt tgttgtggtg ctgtgacgtg    480
ttgtccaacc gtattattcc ggactagtcc tccaggacct cgtctacgag cgctgagcg    540 aggaatggcg caaagggac ggcgagatca gcgacccatg ggccaacgac gaggcggacg    600
gataccagcc gccctcatac gagccggtca accccgaacg caggactccc cagacgccct    660
ccgatggcct gatctgacgt ccgaaaaaag gcgctgtgcg cccttttaa atctttata     720 aatcttttta cattcttta gccctccgc agccttactc tcccaacggg tttcagccga    780
aacctacacc aaaaggggag cgaacctaca ccaaaagggg agcgaaccta caccaaaagg    840
ggagcgaacc tacaccaaaa ggggagctat atacaccttt tgttatttaa ggtgcaagtt    900
gtgctatgct gaggccatgt ccaatgagat cgtgaagttc agcaaccagt tcaacaacgt    960
cgcgctgaag aagttcgacg ccgtgcacct ggacgtgctc atggcgatcg cctcaagggt   1020
gagggagaag ggcacggcca cggtggagtt ctcgttcgag gagctgcgcg gcctcatgcg   1080
attgaggaag aacctgacca caagcagct ggccgacaag atcgtgcaga cgaacgcgcg   1140
cctgctggcg ctgaactaca tgttcgagga ttcgggcaag atcatccagt tcgcgctgtt   1200
cacgaagttc gtcaccgacc gcaggaggc gactctcgcg gttggggtca acgaggagtt   1260
cgcgttcctg ctcaacgacc tgaccagcca gttcacgcgc ttcgagctgg ccgagttcgc   1320
cgacctcaag agcaagtacg ccaaggagtt ctaccgcagg gccaagcagt accgcagctc   1380
cggaatctgg aagatcggcc gcgacgagtt ctgccgactg cttggcgttc caccgtcggc   1440
aataacccag acacgatatc tgaatcagaa ggttcttcag ccaattcagg aggagtgtgg   1500
gcctctcctt ggcctgaaga tcgagcgcca gtacgtgaaa cgcaggctgt cgggcttcgt   1560
gttcacattc gcccgcgaga ccctccggt gatcgacgcc aggcccgtgg aggcgaggaa   1620 gacgacggc gacggcaagg gccattggac gagcgttgcc gggtacgcg aggtgttcac    1680 gaccacggcg ttgttcgacg tgacggccgc ccgggctcac ttcgacggca ccgttgaagc   1740
```

-continued

```
cggggagtgc cgtttctgcg cgtttgacgc gcgcaaccgc gaacatcatg cgcggaacgc    1800
cggaaggctg ttctagcggc cgtgtccgcg cctctggggc ggttgcgcct gccatgggtc    1860
gatctgccgc tgttcggcct cacgctggtc tgtgcgctgc ctgatctccc tgagcaggtc    1920
ggccttggtc ctggggcgc ttcgctcctc gaacgggccg ctctccccca ggtcctcggg    1980
ctcgctcagg tccaacggct cgtcaccgga cggctcgggc cggttctctc cctgtgccgg    2040
gttctccgcc tgtgcgcgtt gttcggccat gcgcagtgcg agggccttca cctgttcggg    2100
gcttgtcgac tcgattttcg ttcgtgaata catgttataa taactataac taataacgta    2160
acgtgactgg caagagatat ttttaaaaca atgaataggt ttacacttac tttagtttta    2220
tggaaatgaa agatcatatc atatataatc tagaataaaa ttaactaaaa taattattat    2280
ctagataaaa aatttagaag ccaatgaaat ctataaataa actaaattaa gtttatttaa    2340
ttaacaacta tggatataaa ataggtacta atcaaaatag tgaggaggat atatttgaat    2400
acatacgaac aaattaataa agtgaaaaaa atacttcgga aacatttaaa aaataaccctt   2460
attggtactt acatgtttgg atcaggagtt gagagtggac taaaaccaaa tagtgatctt    2520
gacttttttag tcgtcgtatc tgaaccattg acagatcaaa gtaaagaaat acttatacaa    2580
aaaattagac ctatttcaaa aaaaatagga gataaaagca acttacgata tattgaatta    2640
acaattatta ttcagcaaga aatggtaccg tggaatcatc ctcccaaaca agaatttatt    2700
tatggagaat ggttacaaga gctttatgaa caaggataca ttcctcagaa ggaattaaat    2760
tcagatttaa ccataatgct ttaccaagca aaacgaaaaa ataaaagaat atacggaaat    2820
tatgacttag aggaattact acctgatatt ccattttctg atgtgagaag agccattatg    2880
gattcgtcag aggaattaat agataattat caggatgatg aaaccaactc tatattaact    2940
ttatgccgta tgattttaac tatggacacg ggtaaaatca taccaaaaga tattgcggga    3000
aatgcagtgg ctgaatcttc tccattagaa catagggaga gaattttgtt agcagttcgt    3060
agttatcttg gagagaatat tgaatggact aatgaaaatg taaatttaac tataaactat    3120
ttaaataaca gattaaaaaa attataaaaa aattgaaaaa atggtggaaa cacttttttc    3180
aattttttta gatcttgagc aaaaggccag caaaaggcca ggaaccgtaa aaaggccgcg    3240
ttgctggcgt ttttccatag gctccgcccc cctgacgagc atcacaaaaa tcgacgctca    3300
agtcagaggt ggcgaaaccc gacaggacta taaagatacc aggcgtttcc ccctggaagc    3360
tccctcgtgc gctctcctgt tccgaccctg ccgcttaccg gatacctgtc cgcctttctc    3420
ccttcgggaa gcgtggcgct ttctcatagc tcacgctgta ggtatctcag ttcggtgtag    3480
gtcgttcgct ccaagctggg ctgtgtgcac gaaccccccg ttcagcccga ccgctgcgcc    3540
ttatccggta actatcgtct tgagtccaac ccggtaagac acgacttatc gccactggca    3600
gcagccactg gtaacaggat tagcagagcg aggtatgtag cggtgctac agagttcttg    3660
aagtggtggc ctaactacgg ctacactaga agaacagtat ttggtatctg cgctctgctg    3720
aagccagtta ccttcggaaa aagagttggt agctcttgat ccggcaaaca aaccaccgct    3780
ggtagcggtg gtttttttgt ttgcaagcag cagattacgc gcagaaaaaa aggatctcaa    3840
gaagatcctt tgatcttttc tac                                            3863
```

<210> SEQ ID NO 51
<211> LENGTH: 4319
<212> TYPE: DNA
<213> ORGANISM: Artificial Sequence
<220> FEATURE:
<223> OTHER INFORMATION: DNA sequence of pTNF3

```
<400> SEQUENCE: 51
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg ggttttcgca gaaacatgcg     300
ctagtatcat tgatgacaac atggactaag caaaagtgct tgtccctga cccaagaagg      360 atgctttatg gtgcgctcct cctcccgtac cccgtccgat aagccggtcg cccatgtggt     420
cgccaacccg caggccgagg ccagctgca gtggctgaac cgtcgcgcca acgccctgct      480
ggccaacggc gtggaactgc gcgacaacca gctggtcgtg ccgtccgagg gcctgtacct     540
gatctactcc caggtgctgt tcaagggcca gggctgcccg tccacccacg tcctgctgac     600
ccataccatc tcccgcatcg ccgtgtccta ccagaccaag gtcaacctgc tgtccgccat     660
caagtccccg tgccagcgtg agaccccgga aggcgccgag ccaagccgt ggtacgaacc      720 gatctacctg gcggcgtgt tccagctgga aaagggcgat cgtctgtccg ccgagatcaa      780
ccgtccggac tacctggatt cgccgagtc cggccaggtc tacttcggca tcatcgccct     840
gtgaccttct gctcgtagcg attacttcga gcattactga cgacaaagac cccgaccgag    900
atggtcgggg tcttttttgtt gtggtgctgt gacgtgttgt ccaaccgtat tattccggac    960
tagtcctcca ggacctcgtc tacgaggcgc tgagcgagga atggcgcaaa agggacggcg   1020
agatcagcga cccatgggcc aacgacgagg cggacggata ccagccgccc tcatacgagc   1080
cggtcaaccc cgaacgcagg actcccccaga cgccctccga tggcctgatc tgacgtccga   1140
aaaaaggcgc tgtgcgccct ttttaaatct tttataaatc tttttacatt cttttagccc   1200
ctccgcagcc ttactctccc aacgggtttc agccgaaacc tacaccaaaa ggggagcgaa   1260
cctacaccaa aaggggagcg aacctacacc aaaaggggag cgaacctaca ccaaaagggg   1320
agctatatac acctttttgtt atttaaggtg caagttgtgc tatgctgagg ccatgtccaa   1380
tgagatcgtg aagttcagca accagttcaa caacgtcgcg ctgaagaagt tcgacgccgt   1440
gcacctggac gtgctcatgg cgatcgcctc aagggtgagg gagaagggca cggcacggt    1500 ggagttctcg ttcgaggagc tgcgcggcct catgcgattg aggaagaacc tgaccaacaa   1560
gcagctggcc gacaagatcg tgcagacgaa cgcgcgcctg ctggcgctga actacatgtt   1620
cgaggattcg ggcaagatca tccagttcgc gctgttcacg aagttcgtca ccgacccgca   1680
ggaggcgact ctcgcggttg gggtcaacga ggagttcgcg ttcctgctca acgacctgac   1740
cagccagttc acgcgcttcg agctggccga gttcgccgac ctcaagagca agtacgccaa   1800
ggagttctac cgcagggcca agcagtaccg cagctccgga atctggaaga tcggccgcga   1860
cgagttctgc cgactgcttg gcgttccacc gtcggcaata acccagacac gatatctgaa   1920
tcagaaggtt cttcagccaa ttcaggagga gtgtgggcct ctccttggcc tgaagatcga   1980
gcgccagtac gtgaaacgca ggctgtcggg cttcgtgttc acattcgccc gcgagacccc   2040
tccggtgatc gacgccaggc ccgtggaggc gaggaagacg gacggcgacg gcaagggcca   2100
ttggacgagc gttgccgggt acggcgaggt gttcacgacc acgcgttgt tcgacgtgac    2160 ggccgcccgg gctcacttcg acggcaccgt tgaagccggg gagtgccgtt tctgcgcgtt   2220
tgacgcgcgc aaccgcgaac atcatgcgcg gaacgccgga aggctgttct agcggccgtg   2280
tccgcgcctc tggggcggtt gcgcctgcca tgggtcgatc tgccgctgtt cggcctcacg   2340
```

-continued

```
ctggtctgtg cgctgcctga tctccctgag caggtcggcc ttggtcctgg gggcgcttcg    2400
ctcctcgaac gggccgctct cccccaggtc ctcgggctcg ctcaggtcca acggctcgtc    2460
accggacggc tcgggccggt tctctccctg tgccgggttc tccgcctgtg cgcgttgttc    2520
ggccatgcgc agtgcgaggg ccttcacctg ttcggggctt gtcgactcga ttttcgttcg    2580
tgaatacatg ttataataac tataactaat aacgtaacgt gactggcaag agatatttt     2640 aaaacaatga ataggtttac acttacttta gttttatgga aatgaaagat catatcatat    2700
ataatctaga ataaaattaa ctaaataat tattatctag ataaaaaatt tagaagccaa     2760
tgaaatctat aaataaacta aattaagttt atttaattaa caactatgga tataaaatag    2820
gtactaatca aaatagtgag gaggatatat ttgaatacat acgaacaaat taataaagtg    2880
aaaaaaatac ttcggaaaca tttaaaaaat aaccttattg gtacttacat gtttggatca    2940
ggagttgaga gtggactaaa accaaatagt gatcttgact ttttagtcgt cgtatctgaa    3000
ccattgacag atcaaagtaa agaaatactt atacaaaaaa ttagacctat ttcaaaaaaa    3060
ataggagata aaagcaactt acgatatatt gaattaacaa ttattattca gcaagaaatg    3120
gtaccgtgga atcatcctcc caaacaagaa tttatttatg gagaatggtt acaagagctt    3180
tatgaacaag gatacattcc tcagaaggaa ttaaattcag atttaaccat aatgctttac    3240
caagcaaaac gaaaaaataa aagaatatac ggaaattatg acttagagga attactacct    3300
gatattccat tttctgatgt gagaagagcc attatggatt cgtcagagga attaatagat    3360
aattatcagg atgatgaaac caactctata ttaacttat gccgtatgat tttaactatg      3420
gacacgggta aaatcatacc aaaagatatt gcgggaaatg cagtggctga atcttctcca    3480
ttagaacata gggagagaat tttgttagca gttcgtagtt atcttggaga gaatattgaa     3540
tggactaatg aaaatgtaaa tttaactata aactattta ataacagatt aaaaaaaatta     3600 taaaaaaatt gaaaaaatgg tggaaacact tttttcaatt tttttagatc ttgagcaaaa    3660
ggccagcaaa aggccaggaa ccgtaaaaag gccgcgttgc tggcgttttt ccataggctc    3720
cgcccccctg acgagcatca aaaaatcga cgctcaagtc agaggtggcg aaacccgaca     3780
ggactataaa gataccaggc gtttccccct ggaagctccc tcgtgcgctc tcctgttccg    3840
accctgccgc ttaccggata cctgtccgcc tttctccctt cgggaagcgt ggcgctttct    3900
catagctcac gctgtaggta tctcagttcg gtgtaggtcg ttcgctccaa gctgggctgt    3960
gtgcacgaac cccccgttca gcccgaccgc tgcgccttat ccggtaacta tcgtcttgag    4020
tccaacccgg taagacacga cttatcgcca ctggcagcag ccactggtaa caggattagc    4080
agagcgaggt atgtaggcgg tgctacagag ttcttgaagt ggtggcctaa ctacggctac    4140
actagaagaa cagtatttgg tatctgcgct ctgctgaagc cagttacctt cggaaaaaga    4200
gttggtagct cttgatccgg caaacaaacc accgctggta gcggtggttt ttttgtttgc    4260
aagcagcaga ttacgcgcag aaaaaaagga tctcaagaag atcctttgat cttttctac      4319
```

<210> SEQ ID NO 52
<211> LENGTH: 34
<212> TYPE: DNA
<213> ORGANISM: Artificial
<220> FEATURE:
<223> OTHER INFORMATION: Forward primer for SP1A

<400> SEQUENCE: 52
cttttctacg gatcctctcg tgtacgcgaa tacg    34

```
<210> SEQ ID NO 53
<211> LENGTH: 32
<212> TYPE: DNA
<213> ORGANISM: Artificial
<220> FEATURE:
<223> OTHER INFORMATION: Reverse primer for SP1A

<400> SEQUENCE: 53
ctcctcgccc ttggattcca cgcgctcctt gg                           32

<210> SEQ ID NO 54
<211> LENGTH: 34
<212> TYPE: DNA
<213> ORGANISM: Artificial
<220> FEATURE:
<223> OTHER INFORMATION: Forward primer for SP2A

<400> SEQUENCE: 54
cttttctacg gatcccgcgc tgcaatggcg tcgg                         34

<210> SEQ ID NO 55
<211> LENGTH: 34
<212> TYPE: DNA
<213> ORGANISM: Artificial
<220> FEATURE:
<223> OTHER INFORMATION: Reverse primer for SP2A

<400> SEQUENCE: 55
ctcctcgccc ttggacaaaa acagcacgcg ggtg                         34

<210> SEQ ID NO 56
<211> LENGTH: 34
<212> TYPE: DNA
<213> ORGANISM: Artificial
<220> FEATURE:
<223> OTHER INFORMATION: Forward primer for SP3A

<400> SEQUENCE: 56
cttttctacg gatccggcgt ctggcagcgc acag                         34

<210> SEQ ID NO 57
<211> LENGTH: 32
<212> TYPE: DNA
<213> ORGANISM: Artificial
<220> FEATURE:
<223> OTHER INFORMATION: Reverse primer for SP3A

<400> SEQUENCE: 57
ctcctcgccc ttggaggcga tggtcagctt gc                           32

<210> SEQ ID NO 58
<211> LENGTH: 32
<212> TYPE: DNA
<213> ORGANISM: Artificial
<220> FEATURE:
<223> OTHER INFORMATION: Forward primer for SP4A

<400> SEQUENCE: 58
cttttctacg gatccatcag aggagccggt gc                           32

<210> SEQ ID NO 59
<211> LENGTH: 33
<212> TYPE: DNA
<213> ORGANISM: Artificial
<220> FEATURE:
<223> OTHER INFORMATION: Reverse primer for SP4A

<400> SEQUENCE: 59
```

-continued ctcctcgccc ttggagccga acagacgcgg ggg                33

<210> SEQ ID NO 60
<211> LENGTH: 33
<212> TYPE: DNA
<213> ORGANISM: Artificial
<220> FEATURE:
<223> OTHER INFORMATION: Forward primer for SP5A

<400> SEQUENCE: 60
cttttctacg gatccctcgc gggcttggcg gtc                33

<210> SEQ ID NO 61
<211> LENGTH: 34
<212> TYPE: DNA
<213> ORGANISM: Artificial
<220> FEATURE:
<223> OTHER INFORMATION: Reverse primer for SP5A

<400> SEQUENCE: 61
ctcctcgccc ttggattggt cgatgatggc cttg                34

<210> SEQ ID NO 62
<211> LENGTH: 33
<212> TYPE: DNA
<213> ORGANISM: Artificial
<220> FEATURE:
<223> OTHER INFORMATION: Forward primer for SP6A

<400> SEQUENCE: 62
cttttctacg gatccgttcg ggtccgggtg cgg                33

<210> SEQ ID NO 63
<211> LENGTH: 35
<212> TYPE: DNA
<213> ORGANISM: Artificial
<220> FEATURE:
<223> OTHER INFORMATION: Reverse primer for SP6A

<400> SEQUENCE: 63
ctcctcgccc ttggaatcga caataggact tttcc                35

<210> SEQ ID NO 64
<211> LENGTH: 34
<212> TYPE: DNA
<213> ORGANISM: Artificial
<220> FEATURE:
<223> OTHER INFORMATION: Forward primer for SP7A

<400> SEQUENCE: 64
cttttctacg gatccaggcg gtccatggtg gatg                34

<210> SEQ ID NO 65
<211> LENGTH: 32
<212> TYPE: DNA
<213> ORGANISM: artificial
<220> FEATURE:
<223> OTHER INFORMATION: Reverse primer for SP7A

<400> SEQUENCE: 65
ctcctcgccc ttggaggtgg aggtggattc gg                32

<210> SEQ ID NO 66
<211> LENGTH: 33
<212> TYPE: DNA
<213> ORGANISM: Artificial

```
<220> FEATURE:
<223> OTHER INFORMATION: Forward primer for SP8A

<400> SEQUENCE: 66
cttttctacg gatccaacca ttcggacgcg cag                              33

<210> SEQ ID NO 67
<211> LENGTH: 32
<212> TYPE: DNA
<213> ORGANISM: Artificial
<220> FEATURE:
<223> OTHER INFORMATION: Reverse primer for SP8A

<400> SEQUENCE: 67
ctcctcgccc ttggacatcg ttgcctcgcc cg                               32

<210> SEQ ID NO 68
<211> LENGTH: 34
<212> TYPE: DNA
<213> ORGANISM: artificial
<220> FEATURE:
<223> OTHER INFORMATION: Forward primer for SP9A

<400> SEQUENCE: 68
cttttctacg gatccccagg gcccgaagga agag                             34

<210> SEQ ID NO 69
<211> LENGTH: 34
<212> TYPE: DNA
<213> ORGANISM: artificial
<220> FEATURE:
<223> OTHER INFORMATION: Reverse primer for SP9A

<400> SEQUENCE: 69
ctcctcgccc ttggagacga tctgatgcgc cagc                             34

<210> SEQ ID NO 70
<211> LENGTH: 33
<212> TYPE: DNA
<213> ORGANISM: Artificial
<220> FEATURE:
<223> OTHER INFORMATION: Forward primer for SP10A

<400> SEQUENCE: 70
cttttctacg gatcccagcc catcgctatg gag                              33

<210> SEQ ID NO 71
<211> LENGTH: 34
<212> TYPE: DNA
<213> ORGANISM: Artificial
<220> FEATURE:
<223> OTHER INFORMATION: Reverse primer for SP10A

<400> SEQUENCE: 71
ctcctcgccc ttggatcgct gcttgagttt gccg                             34

<210> SEQ ID NO 72
<211> LENGTH: 34
<212> TYPE: DNA
<213> ORGANISM: artificial
<220> FEATURE:
<223> OTHER INFORMATION: Forward primer for SP11A

<400> SEQUENCE: 72
cttttctacg gatcctctgt agcgggaggt tgcg                             34
```

```
<210> SEQ ID NO 73
<211> LENGTH: 34
<212> TYPE: DNA
<213> ORGANISM: Artificial
<220> FEATURE:
<223> OTHER INFORMATION: Reverse primer for SP11A

<400> SEQUENCE: 73
ctcctcgccc ttggacagcg tgggctccca agcc                                 34

<210> SEQ ID NO 74
<211> LENGTH: 34
<212> TYPE: DNA
<213> ORGANISM: Artificial
<220> FEATURE:
<223> OTHER INFORMATION: Forward primer for SP12A

<400> SEQUENCE: 74
cttttctacg gatccgcgtt acttccatgt tcgc                                 34

<210> SEQ ID NO 75
<211> LENGTH: 34
<212> TYPE: DNA
<213> ORGANISM: Artificial
<220> FEATURE:
<223> OTHER INFORMATION: Reverse primer for SP12A

<400> SEQUENCE: 75
ctcctcgccc ttggaggaac gggtccacag ggtg                                 34

<210> SEQ ID NO 76
<211> LENGTH: 34
<212> TYPE: DNA
<213> ORGANISM: Artificial
<220> FEATURE:
<223> OTHER INFORMATION: Forward primer for SP13A

<400> SEQUENCE: 76
cttttctacg gatccccttc tcaacgccag cggc                                 34

<210> SEQ ID NO 77
<211> LENGTH: 34
<212> TYPE: DNA
<213> ORGANISM: Artificial
<220> FEATURE:
<223> OTHER INFORMATION: Reverse primer for SP13A

<400> SEQUENCE: 77
ctcctcgccc ttggaagact cgctagcaca gcac                                 34

<210> SEQ ID NO 78
<211> LENGTH: 36
<212> TYPE: DNA
<213> ORGANISM: Artificial
<220> FEATURE:
<223> OTHER INFORMATION: Forward primer for SP14A

<400> SEQUENCE: 78
cttttctacg gatccgacat agcgcggttt catacc                               36

<210> SEQ ID NO 79
<211> LENGTH: 34
<212> TYPE: DNA
<213> ORGANISM: Artificial
<220> FEATURE:
<223> OTHER INFORMATION: Reverse primer for SP14A

<400> SEQUENCE: 79
```

```
ctcctcgccc ttggattggg ccactattgt cttc                          34

<210> SEQ ID NO 80
<211> LENGTH: 34
<212> TYPE: DNA
<213> ORGANISM: Artificial
<220> FEATURE:
<223> OTHER INFORMATION: Forward primer for SP15A

<400> SEQUENCE: 80
cttttctacg gatccaccgg cacctgcgcc ggcg                          34

<210> SEQ ID NO 81
<211> LENGTH: 33
<212> TYPE: DNA
<213> ORGANISM: Artificial
<220> FEATURE:
<223> OTHER INFORMATION: Reverse primer for SP15A

<400> SEQUENCE: 81
ctcctcgccc ttggacttgc ctgaggcatc ttg                           33

<210> SEQ ID NO 82
<211> LENGTH: 39
<212> TYPE: DNA
<213> ORGANISM: Artificial
<220> FEATURE:
<223> OTHER INFORMATION: Forward primer for SP16A

<400> SEQUENCE: 82
cttttctacg gatccatcgc aacacctcca tattgttcc                     39

<210> SEQ ID NO 83
<211> LENGTH: 34
<212> TYPE: DNA
<213> ORGANISM: Artificial
<220> FEATURE:
<223> OTHER INFORMATION: Reverse primer for SP16A

<400> SEQUENCE: 83
ctcctcgccc ttggaggcca acggagtcgt ctcg                          34

<210> SEQ ID NO 84
<211> LENGTH: 37
<212> TYPE: DNA
<213> ORGANISM: Artificial
<220> FEATURE:
<223> OTHER INFORMATION: Forward primer for SP1

<400> SEQUENCE: 84
caagaaggat gctttatggc ggaaactacc gttaagc                       37

<210> SEQ ID NO 85
<211> LENGTH: 34
<212> TYPE: DNA
<213> ORGANISM: Artificial
<220> FEATURE:
<223> OTHER INFORMATION: Forward primer for SP2

<400> SEQUENCE: 85
caagaaggat gctttgtggg tatgactgag aacg                          34

<210> SEQ ID NO 86
<211> LENGTH: 33
<212> TYPE: DNA
<213> ORGANISM: Artificial
```

-continued

```
<220> FEATURE:
<223> OTHER INFORMATION: Forward primer for SP3

<400> SEQUENCE: 86
caagaaggat gctttatgtt caataagcga cac                                      33

<210> SEQ ID NO 87
<211> LENGTH: 33
<212> TYPE: DNA
<213> ORGANISM: Artificial
<220> FEATURE:
<223> OTHER INFORMATION: Forward primer for SP4

<400> SEQUENCE: 87
caagaaggat gctttatgac cactcacaac agc                                      33

<210> SEQ ID NO 88
<211> LENGTH: 33
<212> TYPE: DNA
<213> ORGANISM: Artificial
<220> FEATURE:
<223> OTHER INFORMATION: Forward primer for SP5

<400> SEQUENCE: 88
caagaaggat gctttatgac cgcgattgac gag                                      33

<210> SEQ ID NO 89
<211> LENGTH: 35
<212> TYPE: DNA
<213> ORGANISM: Artificial
<220> FEATURE:
<223> OTHER INFORMATION: Forward primer for SP6

<400> SEQUENCE: 89
caagaaggat gctttatgaa gattgcggtt gcagg                                    35

<210> SEQ ID NO 90
<211> LENGTH: 33
<212> TYPE: DNA
<213> ORGANISM: Artificial
<220> FEATURE:
<223> OTHER INFORMATION: Forward primer for SP7

<400> SEQUENCE: 90
caagaaggat gctttatgtt tgcgtgcgta gcc                                      33

<210> SEQ ID NO 91
<211> LENGTH: 33
<212> TYPE: DNA
<213> ORGANISM: Artificial
<220> FEATURE:
<223> OTHER INFORMATION: Forward primer for SP8

<400> SEQUENCE: 91
caagaaggat gctttatggt tggtgacgac acc                                      33

<210> SEQ ID NO 92
<211> LENGTH: 32
<212> TYPE: DNA
<213> ORGANISM: Artificial
<220> FEATURE:
<223> OTHER INFORMATION: Forward primer for SP9

<400> SEQUENCE: 92
caagaaggat gctttatggg caccatgatg cg                                       32
```

```
<210> SEQ ID NO 93
<211> LENGTH: 34
<212> TYPE: DNA
<213> ORGANISM: Artificial
<220> FEATURE:
<223> OTHER INFORMATION: Forward primer for SP10

<400> SEQUENCE: 93
caagaaggat gctttatgat gactggtgca cagg                               34

<210> SEQ ID NO 94
<211> LENGTH: 32
<212> TYPE: DNA
<213> ORGANISM: Artificial
<220> FEATURE:
<223> OTHER INFORMATION: Forward primer for SP11

<400> SEQUENCE: 94
caagaaggat gctttatgaa gttcaccgtt gc                                 32

<210> SEQ ID NO 95
<211> LENGTH: 39
<212> TYPE: DNA
<213> ORGANISM: Artificial
<220> FEATURE:
<223> OTHER INFORMATION: Forward primer for SP12

<400> SEQUENCE: 95
caagaaggat gctttatggt gtctttcaat aaactgacc                          39

<210> SEQ ID NO 96
<211> LENGTH: 33
<212> TYPE: DNA
<213> ORGANISM: Artificial
<220> FEATURE:
<223> OTHER INFORMATION: Forward primer for SP13

<400> SEQUENCE: 96
caagaaggat gctttatggt cgccgtcctc agg                                33

<210> SEQ ID NO 97
<211> LENGTH: 35
<212> TYPE: DNA
<213> ORGANISM: Artificial
<220> FEATURE:
<223> OTHER INFORMATION: Forward primer for SP14

<400> SEQUENCE: 97
caagaaggat gcttttgcc gggacctata tgtcc                               35

<210> SEQ ID NO 98
<211> LENGTH: 40
<212> TYPE: DNA
<213> ORGANISM: Artificial
<220> FEATURE:
<223> OTHER INFORMATION: Forward primer for SP15

<400> SEQUENCE: 98
caagaaggat gctttatgaa acgtagcgat tatatgttgg                         40

<210> SEQ ID NO 99
<211> LENGTH: 36
<212> TYPE: DNA
<213> ORGANISM: Artificial
<220> FEATURE:
<223> OTHER INFORMATION: Forward primer for SP16

<400> SEQUENCE: 99
```

-continued

```
caagaaggat gctttatgag caatagtgca tcatcg                                    36

<210> SEQ ID NO 100
<211> LENGTH: 34
<212> TYPE: DNA
<213> ORGANISM: Artificial
<220> FEATURE:
<223> OTHER INFORMATION: Forward primer for SP19

<400> SEQUENCE: 100
caagaaggat gcttttggc aagatgggtc actc                                       34

<210> SEQ ID NO 101
<211> LENGTH: 34
<212> TYPE: DNA
<213> ORGANISM: Artificial
<220> FEATURE:
<223> OTHER INFORMATION: Reverse primer for SP19

<400> SEQUENCE: 101
ctcctcgccc ttggagccca tgaccggcat gaac                                      34

<210> SEQ ID NO 102
<211> LENGTH: 37
<212> TYPE: DNA
<213> ORGANISM: Artificial
<220> FEATURE:
<223> OTHER INFORMATION: Forward primer for SP21

<400> SEQUENCE: 102
caagaaggat gctttatggc attgactgat gaacagg                                   37

<210> SEQ ID NO 103
<211> LENGTH: 34
<212> TYPE: DNA
<213> ORGANISM: Artificial
<220> FEATURE:
<223> OTHER INFORMATION: Reverse primer for SP21

<400> SEQUENCE: 103
ctcctcgccc ttggaacgtg cagtggtatg gatg                                      34

<210> SEQ ID NO 104
<211> LENGTH: 33
<212> TYPE: DNA
<213> ORGANISM: Artificial
<220> FEATURE:
<223> OTHER INFORMATION: Forward primer for SP22

<400> SEQUENCE: 104
caagaaggat gcttttggt gtctatgaga agc                                        33

<210> SEQ ID NO 105
<211> LENGTH: 32
<212> TYPE: DNA
<213> ORGANISM: Artificial
<220> FEATURE:
<223> OTHER INFORMATION: Reverse primer for SP22

<400> SEQUENCE: 105
ctcctcgccc ttggagatgc gctcacgctt gg                                        32

<210> SEQ ID NO 106
<211> LENGTH: 30
<212> TYPE: DNA
<213> ORGANISM: Artificial
```

```
<220> FEATURE:
<223> OTHER INFORMATION: Forward primer for SP23

<400> SEQUENCE: 106
gaaggatgct ttatgaacaa gcgatggaac                                    30

<210> SEQ ID NO 107
<211> LENGTH: 38
<212> TYPE: DNA
<213> ORGANISM: Artificial
<220> FEATURE:
<223> OTHER INFORMATION: Reverse primer for SP23

<400> SEQUENCE: 107
ctcctcgccc ttggagatcg tcttgagaat cttcagac                           38

<210> SEQ ID NO 108
<211> LENGTH: 33
<212> TYPE: DNA
<213> ORGANISM: Artificial
<220> FEATURE:
<223> OTHER INFORMATION: Forward primer for SP24

<400> SEQUENCE: 108
caagaaggat gctttatggt cggcatgcgc gac                                33

<210> SEQ ID NO 109
<211> LENGTH: 34
<212> TYPE: DNA
<213> ORGANISM: Artificial
<220> FEATURE:
<223> OTHER INFORMATION: Reverse primer for SP24

<400> SEQUENCE: 109
ctcctcgccc ttggagttgg tgcggttccg gtag                               34

<210> SEQ ID NO 110
<211> LENGTH: 32
<212> TYPE: DNA
<213> ORGANISM: Artificial
<220> FEATURE:
<223> OTHER INFORMATION: Forward primer for SP25

<400> SEQUENCE: 110
caagaaggat gctttgtgat gttatccaca cc                                 32

<210> SEQ ID NO 111
<211> LENGTH: 34
<212> TYPE: DNA
<213> ORGANISM: Artificial
<220> FEATURE:
<223> OTHER INFORMATION: Reverse primer for SP25

<400> SEQUENCE: 111
ctcctcgccc ttggactgct catgatcggc ccag                               34

<210> SEQ ID NO 112
<211> LENGTH: 37
<212> TYPE: DNA
<213> ORGANISM: Artificial
<220> FEATURE:
<223> OTHER INFORMATION: Forward primer for Sec2

<400> SEQUENCE: 112
caagaaggat gcttttttgga acatatgaag atgttcc                           37
```

<210> SEQ ID NO 113
<211> LENGTH: 34
<212> TYPE: DNA
<213> ORGANISM: Artificial
<220> FEATURE:
<223> OTHER INFORMATION: Reverse primer for Sec2

<400> SEQUENCE: 113
ctcctcgccc ttggagtcga gtttcattgt atcg                              34

<210> SEQ ID NO 114
<211> LENGTH: 35
<212> TYPE: DNA
<213> ORGANISM: Artificial
<220> FEATURE:
<223> OTHER INFORMATION: Forward primer for TNF alpha

<400> SEQUENCE: 114
gaaggatgct ttatgtccac cgaatccatg atccg                             35

<210> SEQ ID NO 115
<211> LENGTH: 34
<212> TYPE: DNA
<213> ORGANISM: Artificial
<220> FEATURE:
<223> OTHER INFORMATION: Reverse primer for TNF alpha

<400> SEQUENCE: 115
acgagcagaa ggtcacaggg cgatgatgcc gaag                              34

<210> SEQ ID NO 116
<211> LENGTH: 20
<212> TYPE: DNA
<213> ORGANISM: Artificial
<220> FEATURE:
<223> OTHER INFORMATION: Forward primer for pTNF1

<400> SEQUENCE: 116
gtgcgctcct cctcccgtac                                              20

<210> SEQ ID NO 117
<211> LENGTH: 25
<212> TYPE: DNA
<213> ORGANISM: Artificial
<220> FEATURE:
<223> OTHER INFORMATION: Reverse primer for pTNF1

<400> SEQUENCE: 117
gccgtagtta ggccaccact tcaag                                        25

<210> SEQ ID NO 118
<211> LENGTH: 20
<212> TYPE: DNA
<213> ORGANISM: Artificial
<220> FEATURE:
<223> OTHER INFORMATION: Forward primer for pSPxA-TNF or pSPxB-TNF

<400> SEQUENCE: 118
tggcctaact acggctacac                                              20

<210> SEQ ID NO 119
<211> LENGTH: 37
<212> TYPE: DNA
<213> ORGANISM: Artificial
<220> FEATURE:
<223> OTHER INFORMATION: Reverse primer for pSP7A-TNF

<400> SEQUENCE: 119

```
ggaggaggag cgcacggtgg aggtggattc ggcgaac                                    37

<210> SEQ ID NO 120
<211> LENGTH: 36
<212> TYPE: DNA
<213> ORGANISM: Artificial
<220> FEATURE:
<223> OTHER INFORMATION: Reverse primer for pSP12A-TNF

<400> SEQUENCE: 120
ggaggaggag cgcacggaac gggtccacag ggtgat                                     36

<210> SEQ ID NO 121
<211> LENGTH: 37
<212> TYPE: DNA
<213> ORGANISM: Artificial
<220> FEATURE:
<223> OTHER INFORMATION: Reverse primer for pSP1B-TNF

<400> SEQUENCE: 121
ggaggaggag cgcacttcca cgcgctcctt ggcgatg                                    37

<210> SEQ ID NO 122
<211> LENGTH: 34
<212> TYPE: DNA
<213> ORGANISM: Artificial
<220> FEATURE:
<223> OTHER INFORMATION: Reverse primer for pSP2B-TNF

<400> SEQUENCE: 122
ggaggaggag cgcaccaaaa acagcacgcg ggtg                                       34

<210> SEQ ID NO 123
<211> LENGTH: 32
<212> TYPE: DNA
<213> ORGANISM: Artificial
<220> FEATURE:
<223> OTHER INFORMATION: Reverse primer for pSP3B-TNF

<400> SEQUENCE: 123
ggaggaggag cgcacggcga tggtcagctt gc                                         32

<210> SEQ ID NO 124
<211> LENGTH: 35
<212> TYPE: DNA
<213> ORGANISM: Artificial
<220> FEATURE:
<223> OTHER INFORMATION: Reverse primer for pSP4B-TNF

<400> SEQUENCE: 124
ggaggaggag cgcacgccga acagacgcgg gggaa                                      35

<210> SEQ ID NO 125
<211> LENGTH: 39
<212> TYPE: DNA
<213> ORGANISM: Artificial
<220> FEATURE:
<223> OTHER INFORMATION: Reverse primer for pSP9B-TNF

<400> SEQUENCE: 125
ggaggaggag cgcacgacga tctgatgcgc cagcgcatc                                  39

<210> SEQ ID NO 126
<211> LENGTH: 40
<212> TYPE: DNA
<213> ORGANISM: Artificial
```

```
<220> FEATURE:
<223> OTHER INFORMATION: Reverse primer for pSP10B-TNF

<400> SEQUENCE: 126
ggaggaggag cgcactcgct gcttgagttt gccggaaatc                        40

<210> SEQ ID NO 127
<211> LENGTH: 33
<212> TYPE: DNA
<213> ORGANISM: Artificial
<220> FEATURE:
<223> OTHER INFORMATION: Reverse primer for pSP16B-TNF

<400> SEQUENCE: 127
ggaggaggag cgcacggcca acggagtcgt ctc                              33

<210> SEQ ID NO 128
<211> LENGTH: 39
<212> TYPE: DNA
<213> ORGANISM: Artificial
<220> FEATURE:
<223> OTHER INFORMATION: Reverse primer for pSP23B-TNF

<400> SEQUENCE: 128
ggaggaggag cgcacgatcg tcttgagaat cttcagacg                        39

<210> SEQ ID NO 129
<211> LENGTH: 21
<212> TYPE: DNA
<213> ORGANISM: Artificial
<220> FEATURE:
<223> OTHER INFORMATION: Forward primer for pSec2-TNF

<400> SEQUENCE: 129
tacggatccg tcttcctgct g                                           21

<210> SEQ ID NO 130
<211> LENGTH: 39
<212> TYPE: DNA
<213> ORGANISM: Artificial
<220> FEATURE:
<223> OTHER INFORMATION: Reverse primer for pSec2-TNF

<400> SEQUENCE: 130
gtacgggagg aggagcgcac gtcgagtttc attgtatcg                        39

<210> SEQ ID NO 131
<211> LENGTH: 39
<212> TYPE: DNA
<213> ORGANISM: Artificial
<220> FEATURE:
<223> OTHER INFORMATION: Forward primer for pSec2-TNF

<400> SEQUENCE: 131
cgatacaatg aaactcgacg tgcgctcctc ctcccgtac                        39

<210> SEQ ID NO 132
<211> LENGTH: 23
<212> TYPE: DNA
<213> ORGANISM: Artificial
<220> FEATURE:
<223> OTHER INFORMATION: Reverse primer for pSec2-TNF

<400> SEQUENCE: 132
aggactagtc cggaataata cgg                                         23
```

```
<210> SEQ ID NO 133
<211> LENGTH: 23
<212> TYPE: DNA
<213> ORGANISM: Artificial
<220> FEATURE:
<223> OTHER INFORMATION: Forward primer sequence complementary to a part
      of AAD9 cassette region

<400> SEQUENCE: 133
tgacttagag gaattactac ctg                                             23

<210> SEQ ID NO 134
<211> LENGTH: 20
<212> TYPE: DNA
<213> ORGANISM: Artificial
<220> FEATURE:
<223> OTHER INFORMATION: Reverse primer sequence complementary to a part
      of HU promoter region

<400> SEQUENCE: 134
aaagtggcgg aaagcgccac                                                 20

<210> SEQ ID NO 135
<211> LENGTH: 35
<212> TYPE: DNA
<213> ORGANISM: Artificial
<220> FEATURE:
<223> OTHER INFORMATION: Forward primer for A fragment of pBEshuttle

<400> SEQUENCE: 135
aagcttatcc tgcagtgacc ttctgctcgt agcga                                35

<210> SEQ ID NO 136
<211> LENGTH: 33
<212> TYPE: DNA
<213> ORGANISM: Artificial
<220> FEATURE:
<223> OTHER INFORMATION: Reverse primer for B fragment of pBEshuttle

<400> SEQUENCE: 136
ctgcaggata agcttcataa agcatccttc ttg                                  33

<210> SEQ ID NO 137
<211> LENGTH: 17
<212> TYPE: DNA
<213> ORGANISM: Artificial
<220> FEATURE:
<223> OTHER INFORMATION: Forward primer for IL-18 insert

<400> SEQUENCE: 137
tacttcggca agctggc                                                    17

<210> SEQ ID NO 138
<211> LENGTH: 35
<212> TYPE: DNA
<213> ORGANISM: Artificial
<220> FEATURE:
<223> OTHER INFORMATION: Reverse primer for IL-18 insert

<400> SEQUENCE: 138
gagcagaagg tcatcaatcc tcgttctgga cggtg                                35

<210> SEQ ID NO 139
<211> LENGTH: 21
<212> TYPE: DNA
<213> ORGANISM: Artificial
<220> FEATURE:
<223> OTHER INFORMATION: Forward primer for pSP3B-hIL18mut
```

-continued

```
<400> SEQUENCE: 139
gatgaccttc tgctcgtagc g                                          21

<210> SEQ ID NO 140
<211> LENGTH: 33
<212> TYPE: DNA
<213> ORGANISM: Artificial
<220> FEATURE:
<223> OTHER INFORMATION: Reverse primer for pSP3B-hIL18mut

<400> SEQUENCE: 140
cagcttgccg aagtaggcga tggtcagctt gcc                             33

<210> SEQ ID NO 141
<211> LENGTH: 29
<212> TYPE: DNA
<213> ORGANISM: Artificial Sequence
<220> FEATURE:
<223> OTHER INFORMATION: TNF_F3_primer

<400> SEQUENCE: 141
gaaggatgct ttatggtgcg ctcctcccg                                  29

<210> SEQ ID NO 142
<211> LENGTH: 34
<212> TYPE: DNA
<213> ORGANISM: Artificial Sequence
<220> FEATURE:
<223> OTHER INFORMATION: TNF_R1_primer

<400> SEQUENCE: 142
acgagcagaa ggtcacaggg cgatgatgcc caag                            34

<210> SEQ ID NO 143
<211> LENGTH: 19
<212> TYPE: DNA
<213> ORGANISM: Artificial Sequence
<220> FEATURE:
<223> OTHER INFORMATION: pCDshuttle_F1_primer

<400> SEQUENCE: 143
tgaccttctg ctcgtagcg                                             19

<210> SEQ ID NO 144
<211> LENGTH: 24
<212> TYPE: DNA
<213> ORGANISM: Artificial Sequence
<220> FEATURE:
<223> OTHER INFORMATION: pCDshuttle_R1_primer

<400> SEQUENCE: 144
cataaagcat ccttcttggg tcag                                       24
```

TRANSFECTION VECTOR

TECHNICAL FIELD

The present invention relates to a plasmid for transformation used for the production of a transformed anaerobic bacterium useful as a gene transfer carrier for treating an anaerobic disease such as solid tumor, the plasmid comprising an expression cassette containing a secretory signal peptide that functions in the anaerobic bacterium, and the plasmid being a non-shuttle plasmid. The invention also relates to a gene transfer carrier consisting of an anaerobic bacterium which has been transformed with said transforming plasmid, and to a pharmaceutical composition comprising the gene transfer carrier, as well as to an agent for treating an anaerobic disease comprising the gene transfer carrier.

The invention further relates to a DNA fragment useful for the production of the transformed anaerobic bacterium for treating the anaerobic disease, consisting of a nucleotide sequence encoding a novel secretory signal peptide.

BACKGROUND ART

Recently, in the therapies of a malignant tumor, methods of using a transformed anaerobic bacterium as a carrier for gene transfer have been highlighted. For instance, methods of such as using a transformed *Clostridium* for transferring to the tumor site a gene that expresses nitroreductase, an enzyme that transforms a prodrug of an antitumor substance to the antitumor substance, has been proposed (see Patent Literatures 1 to 3).

Furthermore, methods of using invasive anaerobic bacteria such as *Salmonella*, enteroinvasive *Escherichia coli, Listeria* and *Shigella* for transferring a gene encoding a nucleic acid that abolishes or interferes the expression of a gene involved in an anaerobic disease by RNA interfering to tumor cells, such as small interfering RNAs (siRNAs), short interfering RNAs and short hairpin RNAs, have been investigated (see Patent Literatures 4 to 6).

Nevertheless, since all these microorganisms are pathogenic bacteria which have been mutated to be avirulent, the possibility cannot be denied that back mutation might be happened to return to the original pathogenic bacteria and exert harmfulness. Furthermore, for their motility and invasiveness, these bacteria might express their effect not only in the disease tissue but also in a normal tissue, causing a systemic side effect. Thus, their safety is still a matter of concern.

The inventors focused on *Bifidobacterium* which is a non-pathogenic enteric bacterium being present in human intestine to form a flora and which is known to be an extremely safe obligate anaerobe, and developed a method for treating a malignant tumor using a transformed bacterium of this *Bifidobacterium*.

The inventors then developed a *Bifidobacterium longum* 105A which have been transformed to express cytosine deaminase (hereinbelow referred to as CD), which is an enzyme that converts 5-fluorocytosine (hereinbelow referred to as 5-FC) (a prodrug of an antitumor substance 5-fluorouracil (hereinbelow referred to as 5-FU)) to 5-FU (see Patent Literatures 7 and 8).

This transformed *Bifidobacterium* is characterized in that when being administered into a model animal of solid tumor, which is an anaerobic disease, it specifically colonizes and proliferates in the anaerobic disease tissue which is in hypoxic condition, whereas it quickly disappears in a normal tissue which is not in a hypoxic environment (see non-Patent Literatures 1 and 2).

Furthermore, this transformed *Bifidobacterium* is also characterized in that it does not exhibit antigenicity even when being administered intravenously. It may therefore be expected as an excellent therapeutic for malignant tumor.

Since these transformed bifidobacteria have been transformed using an *Escherichia coli* (*E. coli*)-*Bifidobacterium* shuttle plasmid such as pBLES100-S-eCD and pAV001-HU-eCD-M968, if they are horizontally transferred to an *E. coli*, they might be replicated in that *E. coli*. Therefore, the inventors improved the plasmid to solve this problem and developed a non-shuttle plasmid pBifiCD which does not have a replication origin that functions in *E. coli* (see Patent Literature 9).

On the hand, since these non-shuttle plasmids did not possess a secretory signal, the transformed bifidobacteria could not secrete expressed CD extracellularly.

Therefore, it has been desired to develop a secretory signal peptide that is capable of functioning in *Bifidobacterium* and secreting expressed proteins from the bacteria cell.

As examples of secretory proteins of *Bifidobacterium*, amylase of *Bifidobacterium adolescentis*, and Sec1, Sec2 and Sec 3 of *Bifidobacterium breve* have been reported, and plasmids introduced their secretory signals have also been reported.

For example, *Bifidobacterium longum* MG1 has been reported, which has been transformed with an *E. coli-Bifidobacterium* shuttle plasmid pYBamy59 in which a secretory signal peptide gene of *Bifidobacterium adolescentis* amylase have been transferred (see Patent Literature 3).

Also, *Bifidobacterium breve* UCC2003 has been reported, which has been transformed with an *E. coli-Bifidobacterium* shuttle plasmid such as pESH86 or pESH87 in which a fusion gene of a secretory signal peptide of Sec2 of *B. breve* and human fibroblast growth factor 2 (FGF-2) have been transferred (see Patent Literature 4).

Furthermore, there have been reports of an expression cassette containing a promoter and a signal sequence derived from *Bifidobacterium*, in particular an expression cassette containing a signal of BL1181 gene product or a signal sequence of amyB gene product; indeed, a significant secretion of the expressed protein was confirmed in *B. breve* and *B. longum* (see, Patent Literature 10).

Nevertheless, said plasmids are all *E. coli-Bifidobacterium* shuttle plasmid. A non-shuttle plasmid that does not possess a replication origin that functions in *E. coli* and, that has a secretory signal that functions in *Bifidobacterium*, such as a plasmid of the present invention, was not known. Moreover, it has not been ascertained whether any of these secretory signals function in a bacterial strain other than those already confirmed. Furthermore, the secretion of target protein by the transformed bacterium is expected to be small. Therefore, it was also desired to develop a secretory signal peptide for practical use that is capable of exerting a good secretory function.

CITATION LIST

[Patent Literature 1] U.S. Pat. No. 6,416,754
[Patent Literature 2] U.S. Pat. No. 6,652,849
[Patent Literature 3] US Patent Application No. 2003/0103952
[Patent Literature 4] JP A No. 2008-519002
[Patent Literature 5] JP A No. 2008-92956, WO2006-066048
[Patent Literature 6] WO 2008-091375
[Patent Literature 7] JP A No. 2002-97144
[Patent Literature 8] WO 2007-136107

[Patent Literature 9] WO 2009-128272
[Patent Literature 9] WO 2010-126073
[Non-Patent Literature 1] Yazawa et al., Cancer Gene Therapy, Vol. 7, No. 2, 2000: pp 269-274
[Non-Patent Literature 2] Yazawa et al., Breast Cancer Research and Treatment, Vol. 66, 2001: pp 165-170
[Non-Patent Literature 3] Seong et al., Biotechnology Letters, 2006, Vol. 28: pp 163-168
[Non-Patent Literature 4] Shkoporov et al., Biotechnology Letters, 2008 Vol. 30: pp 1983-1988

SUMMARY OF THE INVENTION

Problems to be Solved by the Invention

The object of the present invention is to provide a transforming plasmid for the production of a transformed anaerobic bacterium, the plasmid that possesses a secretory signal that functions in the anaerobic bacterium and that is a non-shuttle plasmid which does not possess a replication origin that functions in an bacterium other than said anaerobic bacterium, and to provide a transformed anaerobic bacterium transformed with said transforming plasmid, a gene transfer carrier consisting of said transformed anaerobic bacterium, a pharmaceutical composition comprising said gene transfer carrier, and an agent for treating an anaerobic disease comprising said transformed anaerobic bacterium.

Another object of the present invention is to provide a gene transfer carrier consisting of a transformed anaerobic bacterium transformed with said transforming plasmid, a pharmaceutical composition comprising said gene transfer carrier, and an agent for treating an anaerobic disease comprising said transformed anaerobic bacterium.

Furthermore, another object of the present invention is to provide a novel secretory signal that is capable of exerting its function in, e.g., *Bifidobacterium longum* 105A.

Means for Solving the Problems

The inventors previously produced plasmids such as pBLES100-S-eCD and pAV001-HU-eCD-M968 which contains a gene that expresses CD, one of proteins having an activity to convert a precursor of an antitumor substance to the antitumor substance. The inventors then found and reported that an obligate anaerobic bacterium that underwent a recombination with these plasmids, e.g., *Bifidobacterium longum* 105A/pBLES100-S-eCD and *Bifidobacterium longum* 105A/pAV001-HU-eCD-M968 could be expected to be a useful therapeutic for malignant tumor (see Patent Literatures 7 and 8).

The plasmids pBLES100-S-eCD and pAV001-HU-eCD-M968 used for the production of the transformed bacteria in Patent Literatures 7 and 8 above were both *E. coli-Bifidobacterium* shuttle plasmids, and therefore in the case they are horizontally transferred to *E. coli*, they might be replicated in it.

Nevertheless, in a method of treating malignant tumor using a transforming gene transfer carrier, it is critical that the transforming gene in the gene transfer carrier is not to be horizontally transferred to any pathogenic bacteria or aerobic or facultative anaerobic bacteria other than said gene transfer carrier, and that even if it was horizontally transferred, it will not be replicated in those other bacteria. Thus, the plasmid should be a non-shuttle plasmid that does not have a replication origin that functions in a bacterium other than the transformed bacterium, i.e., that is not mutually replicated in both the transformant and other bacteria.

Accordingly, the inventors improved the plasmid to solve this problem and developed a non-shuttle plasmid pBifiCD which does not possess an origin of replication that functions in *E. coli* (Patent Literature 9).

On the other hand, these plasmids are all transforming plasmid having no secretory signal and therefore the transformed bacteria that underwent the recombination using these plasmids do not extracellularly secrete expressed CD. Thus, there still remains the problem that the expression of CD does not directly reflect to CD enzymatic activity, i.e., the drug efficacy.

Moreover, in the case when the bacterium is not to produce an enzyme such as CD that convert a prodrug to an antitumor substance but to produce an antitumor protein or antitumor nucleic acid, it is necessary to induce the bacterium to extracellularly release produced antitumor substance, and therefore the bacterium has to be killed after its proliferation in the anaerobic disease tissue. Therefore, the inventors reached a conclusion that a transforming plasmid having a secretory signal that functions in an obligate anaerobic bacterium, especially in *Bifidobacterium*, is preferred. The inventors devotedly continued the research and completed the invention.

Namely, the present invention relates to the followings:

[1] A plasmid for producing a transformed anaerobic bacterium, the plasmid comprising an expression cassette containing a secretory signal that functions in the anaerobic bacterium, and the plasmid being a non-shuttle plasmid.

[2] The plasmid according to [1], wherein the anaerobic bacterium is *Bifidobacterium*.

[3] The transforming plasmid according to [1] or [2], wherein the secretory signal peptide is derived from *Bifidobacterium*.

[4] The transforming plasmid according to [3], wherein the secretory signal peptide is derived from *Bifidobacterium longum*.

[5] The transforming plasmid according to any one of [1] to [4], wherein the secretory signal is a DNA according to any one of the nucleotide sequences of SEQ ID No.: 6 to 28, or said sequence in which one or several nucleotide thereof are deleted, substituted or added.

[6] The transforming plasmid according to [5], wherein the secretory signal is a nucleotide sequence of SEQ ID No.: 6, 7, 8, 9, 12, 14, 15, 17, 21, 25 or 28, or said sequence in which one or several nucleotide thereof are deleted, substituted or added.

[7] The transforming plasmid according to [6], wherein the secretory signal is a DNA according to the nucleotide sequence of either SEQ ID No.: 8 or 25 or a single nucleotide polymorphism thereof.

[8] The transforming plasmid according to any one of [1] to [7], wherein a promoter contained in the expression cassette is a DNA according to any one of nucleotide sequences of promoter regions of SEQ ID Nos.: 29 to 44 or the nucleotide sequence of SEQ ID No.: 45, or said sequence in which one or several nucleotide thereof are deleted, substituted or added.

[9] The transforming plasmid according to [8], wherein the promoter contained in the expression cassette is a nucleotide sequence of a promoter region of SEQ ID No.: 35 or the nucleotide sequence of SEQ ID No.: 45, or said sequence in which one or several nucleotide thereof are deleted, substituted or added.

[10] The transforming plasmid according to any one of [1] to [9], wherein a terminator contained in the expression cassette is a DNA according to the nucleotide sequence of SEQ ID No.: 46, or said sequence in which one or several nucleotide thereof are deleted, substituted or added.

[11] The transforming plasmid according to any one of [1] to [10], wherein a target gene contained in the expression cassette is a gene encoding a fluorescent protein.

[12] The transforming plasmid according to any one of [1] to [10], wherein a target gene contained in the expression cassette is a gene encoding a protein having an antitumor activity.
[13] The transforming plasmid according to [12], wherein the protein having an antitumor activity is one selected from the group consisting of cytokines such as interferon (IFN)-α, IFN-β, IFN-γ, granulocyte-macrophage colony-stimulating factor (GM-CSF), interleukin (IL)-1α, IL-1β, IL-2, IL-3, IL-4, IL-6, IL-7, IL-10, IL-12, IL-13, IL-15, IL-18, tumor necrosis factor (TNF)-α, lymphotoxin (LT)-β, TNF-related apoptosis inducing ligand (TRAIL), granulocyte colony-stimulating factor (G-CSF), macrophage colony-stimulating factor (M-CSF), macrophage migration-inhibitory factor (MIF), leukemia-inhibitory factor (LIF), T cell activator co-stimulators B7 (CD80) and B7-2 (CD86), Kit ligand and oncostatin M, and anti-angiogenic agents such as endostatin, angiostatin, kringle-1, kringle-2, kringle-3, kringle-4 and kringle-5.
[14] The transforming plasmid according to [13], wherein the protein having an antitumor activity is either tumor necrosis factor (TNF)-α or TNF-related apoptosis inducing ligand (TRAIL).
[15] The transforming plasmid according to any one of [1] to [10], wherein the target gene is a gene encoding a protein having an activity to convert a precursor of an antitumor substance to the antitumor substance.
[16] The transforming plasmid according to [15], wherein the protein having an activity to convert a precursor of an antitumor substance to the antitumor substance is one selected from the group consisting of cytosine deaminase, nitroreductase and β-glucronidase.
[17] The transforming plasmid according to any one of [1] to [10], wherein the target gene is a gene encoding a protein having a therapeutic activity for an ischemic disease.
[18] The transforming plasmid according to [17], wherein the protein having a therapeutic activity for an ischemic disease is one selected from the group consisting of proteins having a proangiogenic activity such as fibroblast growth factor 2 (FGF2), endothelial cell growth factor (ECGF), vascular endothelial growth factor (VEGF) and hepatocyte growth factor (HGF).
[19] The transforming plasmid according to any one of [1] to [10], wherein the target gene is a nucleic acid having a therapeutic activity for an anaerobic disease.
[20] The transforming plasmid according to [19], wherein the nucleic acid having a therapeutic activity for an anaerobic disease is an siRNA associated with at least one tumor cell growth factor selected from the group consisting of fibroblast growth factor 2(FGF2), endothelial cell growth factor (ECGF), vascular endothelial growth factor (VEGF) and hepatocyte growth factor (HGF).
[21] The transforming plasmid according to any one of [1] to [20], comprising a DNA sequence according to the nucleotide sequence of SEQ ID No.: 5, or said sequence in which one or several nucleotide thereof are deleted, substituted or added (pBifi-SP3B-TNF alpha).
[22] A gene transfer carrier consisting of an anaerobic bacterium transformed with the transforming plasmid according to any one of [1] to [21].
[23] The gene transfer carrier according to [22], wherein the anaerobic bacterium is an avirulent enterobacterium.
[24] The gene transfer carrier according to [22] or [23], wherein the anaerobic bacterium is *Bifidobacterium*.
[25] The gene transfer carrier according to [24], wherein the *Bifidobacterium* is a species selected from the group consisting of *Bifidobacterium adolescentis, Bifidobacterium angulatum, Bifidobacterium animalis, Bifidobacterium asteroides, Bifidobacterium bifidum, Bifidobacterium boum, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacteria globosum, Bifidobacteria indicum, Bifidobacterium infantis, Bifidobacteria inopinatum, Bifidobacterium lactis, Bifidobacterium lactentis, Bifidobacterium liberorum, Bifidobacterium longum, Bifidobacterium magnum, Bifidobacterium merycicum, Bifidobacterium minimum, Bifidobacterium mongoliense, Bifidobacterium parvulorum, Bifidobacterium pseudocatenulatum, Bifidobacterium pseudolongum, Bifidobacterium psychroaerophilum, Bifidobacterium pullorum, Bifidobacterium ruminale, Bifidobacterium ruminantium, Bifidobacterium saeculare, Bifidobacterium scardovii, Bifidobacterium subtile, Bifidobacterium suis, Bifidobacterium thermacidophilum* and *Bifidobacterium thermophilum*.
[26] The gene transfer carrier according to [25], wherein the *Bifidobacterium* is *Bifidobacterium longum*.
[27] The gene transfer carrier according to any one of [22] to [26], being capable of growing in a tumor tissue in an anaerobic environment and being capable of expressing and secreting at least one protein or nucleic acid that is useful for diagnosis or treatment of an anaerobic disease.
[28] The gene transfer carrier according to [27], wherein the protein that is useful for diagnosis of an anaerobic disease is a fluorescent protein.
[29] The gene transfer carrier according to [27], wherein the protein that is useful for treatment of an anaerobic disease is a protein having an antitumor activity.
[30] The gene transfer carrier according to [28], wherein the protein having an antitumor activity is one selected from the group consisting of cytokines such as interferon (IFN)-α, IFN-β, IFN-γ, granulocyte-macrophage colony-stimulating factor (GM-CSF), interleukin (IL)-1α, IL-1β, IL-2, IL-3, IL-4, IL-6, IL-7, IL-10, IL-12, IL-13, IL-15, IL-18, tumor necrosis factor (TNF)-α, lymphotoxin (LT)-β, TNF-related apoptosis inducing ligand (TRAIL), granulocyte colony-stimulating factor (G-CSF), macrophage colony-stimulating factor (M-CSF), macrophage migration-inhibitory factor (MIF), leukemia-inhibitory factor (LIF), T cell activator co-stimulators B7 (CD80) and B7-2 (CD86), Kit ligand and oncostatin M, and anti-angiogenic agents such as endostatin, angiostatin, kringle-1, kringle-2, kringle-3, kringle-4 and kringle-5.
[31] The gene transfer carrier according to [27], wherein the protein that is useful for treatment of an anaerobic disease is a protein having an activity to convert a precursor of an antitumor substance to the antitumor substance.
[32] The gene transfer carrier according to [31], wherein the protein having an activity to convert a precursor of an antitumor substance to the antitumor substance is selected from the group consisting of cytosine deaminase, nitroreductase and β-glucronidase.
[33] The gene transfer carrier according to [27], wherein the nucleic acid that is useful for treatment of an anaerobic disease is an siRNA associated with an anaerobic disease factor.
[34] The gene transfer carrier according to [33], wherein the siRNA associated with an anaerobic disease factor is an siRNA associated with at least one tumor cell growth factor selected from the group consisting of fibroblast growth factor 2(FGF2), endothelial cell growth factor (ECGF), vascular endothelial growth factor (VEGF) and hepatocyte growth factor (HGF).
[35] A pharmaceutical composition comprising the gene transfer carrier according to any one of [22] to [34].

[36] A DNA encoding a secretory signal peptide derived from *Bifidobacterium longum*.

[37] The DNA encoding a secretory signal peptide according to [36], comprising a DNA sequence according to any one of the nucleotide sequences of SEQ ID No.: 6 to 28, or said sequence in which one or several nucleotide thereof are deleted, substituted or added.

[38] A secretory signal peptide encoded by the DNA according to [36] or [37].

[39] A transforming plasmid comprising the DNA according to [36] or [37].

[40] The transforming plasmid according to [39], further comprising a DNA encoding a protein or nucleic acid that is useful for diagnosis or treatment of an anaerobic disease.

[41] The transforming plasmid according to [40], wherein the protein that is useful for diagnosis of an anaerobic disease is a fluorescent protein.

[42] The transforming plasmid according to [40], wherein the protein that is useful for treatment of an anaerobic disease is a protein having an antitumor activity.

[43] The transforming plasmid according to [42], wherein the protein having an antitumor activity is one selected from the group consisting of cytokines such as interferon (IFN)-α, IFN-β, IFN-γ, granulocyte-macrophage colony-stimulating factor (GM-CSF), interleukin (IL)-1α, IL-1β, IL-2, IL-3, IL-4, IL-6, IL-7, IL-10, IL-12, IL-13, IL-15, IL-18, tumor necrosis factor (TNF)-α, lymphotoxin (LT)-β, TNF-related apoptosis inducing ligand (TRAIL), granulocyte colony-stimulating factor (G-CSF), macrophage colony-stimulating factor (M-CSF), macrophage migration-inhibitory factor (MIF), leukemia-inhibitory factor (LIF), T cell activator co-stimulators B7 (CD80) and B7-2 (CD86), Kit ligand and oncostatin M, and anti-angiogenic agents such as endostatin, angiostatin, kringle-1, kringle-2, kringle-3, kringle-4 and kringle-5.

[44] The transforming plasmid according to [40], wherein the protein that is useful for treatment of an anaerobic disease is a protein having an activity to convert a precursor of an antitumor substance to the antitumor substance.

[45] The transforming plasmid according to [44], wherein the protein having an activity to convert a precursor of an antitumor substance to the antitumor substance is one selected from the group consisting of cytosine deaminase, nitroreductase and β-glucronidase.

[46] The transforming plasmid according to [40], wherein the nucleic acid that is useful for treatment of an anaerobic disease is an siRNA associated with an anaerobic disease factor.

[47] The transforming plasmid according to [46], wherein the siRNA associated with an anaerobic disease factor is an siRNA associated with at least one tumor cell growth factor selected from the group consisting of fibroblast growth factor 2(FGF2), endothelial cell growth factor (ECGF), vascular endothelial growth factor (VEGF) and hepatocyte growth factor (HGF).

[48] A gene transfer carrier that is an anaerobic bacterium transformed with the transforming plasmid according to any one of [39] to [47].

[49] The gene transfer carrier according to [48], wherein the anaerobic bacterium is a *Bifidobacterium*.

[50] The gene transfer carrier according to [49], wherein the *Bifidobacterium* is a species selected from the group consisting of *Bifidobacterium adolescentis, Bifidobacterium angulatum, Bifidobacterium animalis, Bifidobacterium asteroides, Bifidobacterium bifidum, Bifidobacterium boum, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacterium globosum, Bifidobacterium indicum, Bifidobacterium infantis, Bifidobacterium inopinatum, Bifidobacterium lactis, Bifidobacterium lactentis, Bifidobacterium liberorum, Bifidobacterium longum, Bifidobacterium magnum, Bifidobacterium merycicum, Bifidobacterium minimum, Bifidobacterium mongoliense, Bifidobacterium parvulorum, Bifidobacterium pseudocatenulatum, Bifidobacterium pseudolongum, Bifidobacterium psychroaerophilum, Bifidobacterium pullorum, Bifidobacterium ruminale, Bifidobacterium ruminantium, Bifidobacterium saeculare, Bifidobacterium scardovii, Bifidobacterium subtile, Bifidobacterium suis, Bifidobacterium thermacidophilum* and *Bifidobacterium thermophilum*.

[51] The gene transfer carrier according to [50], wherein the *Bifidobacterium* is *Bifidobacterium longum*.

[52] A pharmaceutical composition comprising the gene transfer carrier according to any one of [48] to [51].

Effects of the Invention

The plasmid of the present invention is a novel plasmid useful for producing a transformed anaerobic bacterium for treating an anaerobic disease such as solid tumor, comprising an expression cassette having a secretory signal, and being a non-shuttle plasmid. The plasmid of the present invention does not comprise a replication origin that functions in a bacterium other than the transformed bacterium, and it is a non-shuttle plasmid which is not mutually replicated in both the transformant and other bacteria. It is therefore an extremely safe vector.

Furthermore, the anaerobic bacterium transformed with the transforming plasmid of the present invention specifically colonizes and proliferates in an anaerobic disease tissue, and is capable of producing and secreting a protein or nucleic acid having a therapeutic activity for anaerobic disease, thereby being expected as a high-quality gene transfer carrier extremely useful as a therapeutic for an anaerobic disease.

Moreover, the novel secretory signal of the present invention is not only to be inserted into a plasmid, but also is to be incorporated directly into the genome of an anaerobic bacterium, allowing the production of a transformed anaerobic bacterium that is useful for treating an anaerobic disease.

BRIEF DESCRIPTION OF DRAWINGS

FIG. 8 is a picture showing western blotting of *B. longum* 105A/pSP1B-TNF alpha, *B. longum* 105A/pSP3B-TNF alpha, *B. longum* 105A/pSP4B-TNF alpha, *B. longum* 105A/pSP7B-TNF alpha, *B. longum* 105A/pSP12B-TNF alpha, *B. longum* 105A/pSP16B-TNF alpha, *B. longum* 105A/pSP23B-TNF alpha, *B. longum* 105A/pSP7A-TNF alpha and *B. longum* 105A/pSec2-TNF alpha. In this figure, C indicates the lane for intracellular protein extract, T indicates the lane for the culture supernatant concentrate, S indicates the lane for the culture supernatant and the numbers on the vertical axis indicates the molecular weight (kDa).

FIG. 10 is a map showing a summary of the construction of plasmid pBifi-SP3B-TNF alpha.

FIG. 11 is a picture showing the results of western blotting of *Bifidobacterium longum* 105A/pBifiSP3B-TNF alpha. The molecular weight markers of Lane 1 indicate, from the bottom, 20, 30, 40, 50, 60 and 80 kDa, respectively.

FIG. 12 is a map showing a summary of the construction of TNFα-expressing plasmid (pTNF3).

DESCRIPTION OF EMBODIMENTS

Figure 1:
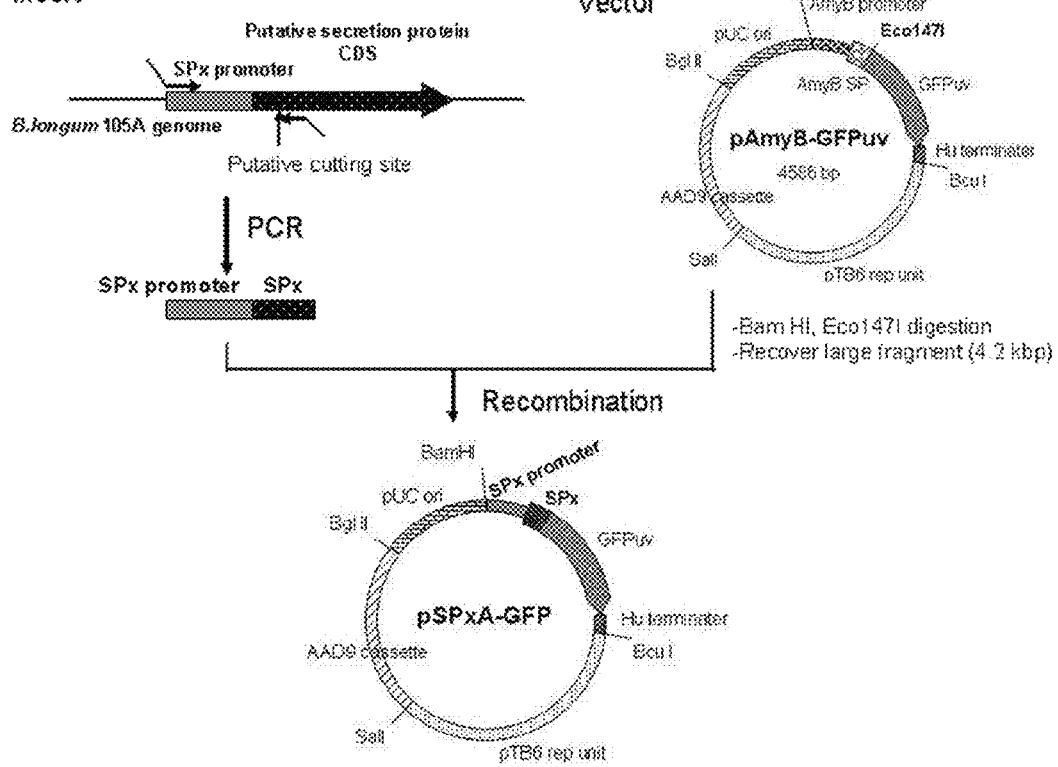
FIG. 1 is a map showing a summary of the construction of a secretory GFP-expressing plasmid (pSPxA-GFP).

A non-shuttle plasmid used herein means a plasmid which comprises a replication origin that functions in the anaerobic bacterium to be transformed but does not comprises a replication origin that functions in other bacterium, and which is not mutually replicated in both the transformed anaerobic bacterium and a bacterium other than the transformed anaerobic bacterium.

The secretory signal used herein means a DNA fragment consisting of a nucleotide sequence encoding a secretory signal peptide (it may be referred to as a secretory signal peptide gene).

Herein, a DNA encoding a protein having an antitumor activity, a DNA encoding a protein having an activity to convert a precursor of an antitumor substance to the antitumor substance, and a DNA encoding a protein having a therapeutic activity for an ischemic disease, etc. may collectively be referred to as "DNA encoding the protein of interest".

An "siRNA" used herein is meant to include any of followings: an siRNA that is referred to as a small interfering RNA or a short interfering RNA, and a short hairpin RNA (shRNA) which is cleaved by an enzyme such as a Dicer within the target cell to generate an siRNA. It may also collectively refer to those including a modified siRNA and an siRNA complex.

An "expression cassette" used herein refers to a set of genes for allowing the expression of certain protein or peptide fragment, and which comprises expression units such as a promoter, a gene encoding a protein to be expressed (target gene) and a terminator, and which may optionally further comprise other useful units. Other useful unit may include such as, for example, a gene encoding a signal peptide such as a secretory signal or a gene encoding a labeling protein.

The present invention relates to a transforming plasmid for producing a transformed anaerobic bacterium, comprising an expression cassette comprising a secretory signal that functions in the anaerobic bacterium, and being a non-shuttle plasmid.

A transforming gene transfer carrier used for the treatment of a disease in which the disease site is in an anaerobic environment (hereinbelow referred to as an anaerobic disease) such as solid tumor or ischemic disease is required to be avirulent from the safety point of view.

Moreover, it is more preferred to be obligate anaerobic bacterium which colonizes and proliferates only in the disease tissue in an anaerobic condition, and neither colonizes nor proliferates in a normal tissue that is not in an anaerobic condition.

The inventors previously studied on the method for treating malignant tumor using an obligate anaerobe *Bifidobacterium*, and developed *Bifidobacterium longum* 105A transformed with a plasmid in which the gene of CD, an enzyme that converts a prodrug 5-FC to an antitumor substance 5-FU, has been incorporated (see Patent literatures 7 and 8).

It was confirmed that these transformed bifidobacteria specifically colonized and proliferated in an anaerobic disease tissue in a hypoxic condition upon being intravenously administered into a model animal of solid tumor, i.e., an anaerobic disease, whereas they quickly disappear in a normal tissue that is not in an anaerobic condition (see Non-patent literatures 1 and 2).

Nevertheless, since the transformed bifidobacteria have been transformed using *E. coli-Bifidobacterium* shuttle plasmids such as pBLES100-S-eCD or pAV001-HU-eCD-M968, they might be replicated in *E. coli* when being horizontally transferred to *E. coli*.

Therefore, the inventors improved the plasmid in order to solve this problem and developed a non-shuttle plasmid pBifiCD which does not comprise a replication origin that functions in *E. coli* (see Patent literature 9).

In methods for treating malignant tumor using these transformed bacteria, i.e., an enzyme-prodrug therapy (CD-5-FC therapy), it is desired that the antitumor substance 5-FU acts in tumor-tissue-specific manner in order to minimize its side effects. The inventors therefore transformed these transformed bifidobacteria using the plasmids none of which comprises a secretory signal, such that the expressed CD is not to be secreted from the bacteria cell but to convert intracellularly-incorporated 5-FC to 5-FU and export it from the bacteria cell, so that 5-FU exerts its antitumor activity only within tumor tissue.

The bifidobacteria transformed with these plasmids without a secretory signal was characterized in that they colonize and proliferate specifically in an anaerobic disease tissue in an anaerobic condition and that the enzyme CD remains inside of the bacterium that colonizes and proliferates specifically in the anaerobic disease tissue. From these characteristics, the bifidobacteria has an advantage that they could avoid the systemic side-effect of antitumor substance 5-FU. On the other hand, a problem was also found that the 5-FU production is not equal to the CD production produced by the transformed *Bifidobacterium* but correlates to the amount of 5-FC uptake by the bacteria cell, thus the enzymatic function of the produced CD was not fully exerted.

Moreover, in a case of a bacterium which produces not an enzyme that converts a prodrug such as CD to an antitumor substance but produces an antitumor protein or nucleic acid, it was necessary to destroy the cell after its expansion in the anaerobic disease tissue, in order to release the produced antitumor substance from the bacteria cell.

In order to solve these problems, the inventors started the development of a plasmid comprising a secretory signal that functions in an anaerobic bacterium, preferably an avirulent, obligate anaerobic bacterium, for allowing the secretion of the produced active substance, and the inventors developed a signal peptide useful for the production of said plasmid, which functions at least in the anaerobic bacterium and exhibits an excellent secretory effect of the expressed protein.

Furthermore, in a method for treating such as solid tumor using a transformant gene transfer carrier, as mentioned above, it is also very important that the transforming gene in the gene transfer carrier to be used is not to be horizontally transferred to a pathogenic bacterium or an aerobic or facultative anaerobic bacterium other than said gene transfer carrier, and that it is not to be replicated in that bacterium even if it was horizontally transferred.

Accordingly, said plasmid comprising a secretory signal is preferred to be a non-shuttle plasmid that does not have a replication origin that functions in an bacterium other than the transformed bacterium.

The plasmid of the present invention is a plasmid for producing a transformed anaerobic bacterium, comprising an expression cassette comprising a secretory signal that functions at least in the anaerobic bacterium. Moreover, it is a non-shuttle plasmid, which does not comprise a replication origin that functions in a bacterium other than the transformed bacterium and which is not mutually replicated in both the transformant and other bacteria.

More specifically, it is a plasmid for producing a transformed anaerobic bacterium, which functions at least in *Bifidobacterium*, and which comprises an expression cassette having a secretory signal exhibiting an excellent secretory effect, and which does not comprises a replication origin that functions in a bacterium other than the transformed bacterium and which is not mutually replicated in both the transformant and other bacteria.

The transforming plasmid of the present invention is characterized in that, by using this, it is able to produce a transformed anaerobic bacterium that is capable of expressing any protein or nucleic acid of interest and exerting an excellent and practical secretory function by the action of the secretory signal peptide contained in the expression cassette.

Moreover, the transforming plasmid of the present invention is characterized in that it is a non-shuttle plasmid vector which does not comprise a replication origin that functions in a bacterium other than the transformed bacterium and which is not mutually replicated in both the transformant and other bacteria.

To date, *Bifidobacterium adolescentis* amylase and *Bifidobacterium breve* Sec1, Sec2 and Sec3 for example have been reported as a signal peptide that functions in an anaerobic bacterium, especially in *Bifidobacterium*, and the plasmids with their secretory signals transferred therein have also been reported. However, in the bifidobacteria transformed with these plasmid, the expected secretion of the protein of interest was small.

Moreover, no GFP-secreting function was exhibited in *Bifidobacterium longum* transformed using a plasmid produced by cloning the secretory signal and promoter regions of the *Bifidobacterium adolescentis* amylase and incorporating these with a gene encoding an UV-optimized green fluorescent protein mutant (GFPuv: CLONTECH Laboratories, Inc.), when being confirm its secreting function of an expressed protein (GFP), assuming that this secretory signal peptide does not afford secreting any protein of interest.

Furthermore, previously reported plasmid vectors for producing transformed anaerobic bacteria which extracellularly secrete the expressed protein are shuttle plasmids made by fusing a plasmid derived from *E. coli* to a plasmid derived from the transformed bacterium, which function both in *E. coli* and the transformed bacteria. No report has been made on a transforming plasmid which functions only in the transformed bacterium other than *E. coli*.

As a secretory signal peptide that functions in an anaerobic bacterium comprised by the transforming plasmid of the present invention, any secretory signal peptide may be used as long as it functions at least in the anaerobic bacterium, although those which function in *Bifidobacterium* are preferred. In view of the toxicity to the transformed bacterium and functionality, a secretory signal peptide derived from *Bifidobacterium* is more preferred, and a secretory signal peptide derived from *Bifidobacterium longum* is further preferred. Examples of secretory signals derived from *Bifidobacterium longum* include, for example, a secretory signal peptide encoded by a DNA expressed by any one of the nucleotide sequences of SEQ ID No.: 6 to 28, or said sequence in which one or several nucleotide thereof are deleted, substituted or added. Among these, a secretory signal peptide encoded by a DNA expressed by the nucleotide sequence of SEQ ID No.: 6, 7, 8, 9, 12, 14, 15, 17, 21, 25 or 28, or said sequence in which one or several nucleotide thereof are deleted, substituted or added is preferred, and a secretory signal peptide encoded by a DNA expressed by the nucleotide sequence of SEQ ID No.: 8 or 25, or said sequence in which one or several nucleotide thereof are deleted, substituted or added is most preferred.

Furthermore, a promoter in the expression cassette comprised in the transforming plasmid of the present invention may be any promoter as long as it functions in an anaerobic bacterium and functions as a promoter of the secretory signal peptide. Examples include such as a promoter adjacent to the upstream of a secretory signal peptide derived from *Bifidobacterium* (promoter X), or a promoter of a gene encoding a histone-like DNA binding protein that functions in *Bifidobacterium* (HU promoter). Specifically, a promoter encoded by a DNA of a promoter region of the nucleotide sequence expressed by any one of SEQ ID No.: 29 to 44, and a DNA of the nucleotide sequence expressed by any one of SEQ ID No.: 45 or said nucleotide sequence in which one or several nucleotide thereof are deleted, substituted or added is included. Among these, a promoter or HU promoter encoded by a DNA of a promoter region of the nucleotide sequence expressed by SEQ ID No.: 35 or a single nucleotide polymorphism thereof is preferred, and a HU promoter is more preferred, and a promoter encoded by a DNA expressed by the nucleotide sequence of SEQ ID No.: 45 or said sequence in which one or several nucleotide thereof are deleted, substituted or added is most preferred.

Furthermore, a terminator comprised in the transforming plasmid of the present invention may be any terminator as long as it functions in *Bifidobacterium* and functions as a terminator of a secretory signal peptide, although a terminator of a gene encoding a histone-like DNA binding protein that functions in *Bifidobacterium* (HU terminator) is preferred, and in particular, a DNA expressed by the nucleotide sequence of SEQ ID No.: 46 or said sequence in which one or several nucleotide thereof are deleted, substituted or added is most preferred.

A "single nucleotide mutant" herein means a single nucleotide polymorphism in which at least one nucleotide has been mutated (hereinbelow referred to as SNPs), including a SNP at one site as well as SNPs at several sites. Accordingly, it is interchangeable with a "sequence in which one or several nucleotide thereof are deleted, substituted or added".

As a gene encoding a protein or nucleic acid of interest to be secreted (i.e., a target gene) comprised in the transforming plasmid of the present invention, any gene may be used such as a gene encoding a fluorescent protein, a gene encoding a protein having an antitumor activity, a gene encoding a protein having a therapeutic activity for an ischemic disease and a gene encoding a protein having an activity to convert a precursor of an antitumor substance to the antitumor substance.

A fluorescent protein includes such as green fluorescent protein (GFP) and red fluorescent protein (RFP) of various types.

A protein having an antitumor activity includes, for example, a cytokine, and the examples of specific cytokines include such as interferon (IFN)-α, β, γ, granulocyte-macrophage colony-stimulating factor (GM-CSF), interleukin (IL)-1α, 1β, 2, 3, 4, 6, 7, 10, 12, 13, 15, 18, tumor necrosis factor (TNF)-α, lymphotoxin (LT)-β, TNF-related apoptosis inducing ligand (TRAIL), granulocyte colony-stimulating factor (G-CSF), macrophage colony-stimulating factor (M-CSF), macrophage migration-inhibitory factor (MIF), leukemia-inhibitory factor (LIF), T cell activator co-stimulators B7 (CD80) and B7-2 (CD86), Kit ligand, oncostatin M.

It also includes anti-angiogenic agents such as endostatin, angiostatin, kringle-1, 2, 3, 4 and 5.

Proteins having an activity to convert a precursor of an antitumor substance to the antitumor substance may include such as cytosine deaminase (hereinbelow referred to as CD), i.e., an enzyme that converts 5-florocytosine (hereinbelow referred to as 5-FC) to an antitumor active substance 5-fluorourasil (hereinbelow referred to as 5-FU); nitroreductase, i.e., an enzyme that converts 5-aziridino-2,4-dinitrobenzamide (hereinbelow referred to as CB1945) to an antitumor active alkylating agent; herpes simplex virus type 1 thymidine kinase (hereinbelow referred to as HSV1-TK), i.e., an enzyme that convert gancyclovir to an antitumor active metabolite; and β-glucronidase, i.e., an enzyme that convert a glucronate-conjugated antitumor active substance to the antitumor active substance.

Moreover, proteins having a therapeutic activity for an ischemic disease may include a protein having a proangiogenic activity useful for treating an ischemic disease. Specifically it may include such as fibroblast growth factor 2 (FGF2), endothelial cell growth factor (ECGF), vascular endothelial growth factor (VEGF) and hepatocyte growth factor (HGF).

The sequences of these proteins are known in various organisms, and a DNA encoding the protein of interest may be obtained by utilizing known procedures such as PCR methods and artificial gene synthesis, based on the sequence information thereof.

A nucleic acid having a therapeutic activity for a disease in an anaerobic environment may include an siRNA associated with an anaerobic disease factor. More specifically, siRNAs directed to tumor cell growth factors such as fibroblast growth factor 2(FGF2), endothelial cell growth factor (ECGF), vascular endothelial growth factor (VEGF) and hepatocyte growth factor (HGF) may be included.

Similarly, the sequences of these nucleic acids are known and can be obtained by utilizing known procedures such as PCR methods based on the sequence information thereof.

The plasmid of the present invention may be produced, for example, as follows:

A shuttle plasmid may be produced, for example, according to the routine procedures, by inserting into a shuttle plasmid having a replication origin that functions in each of a transformant and other bacteria (e.g., *E. coli*) a secretory signal that functions at least in *Bifidobacterium* and its promoter gene, and, in their downstream, at least one gene or nucleic acid encoding a desired protein useful for diagnosis or treatment of an anaerobic disease (target gene), and, in further downstream, a terminator gene of the secretory signal peptide that functions in the anaerobic bacterium.

Furthermore, if desired, the replication origin of the bacterium other than the transformed bacterium may be removed from this shuttle plasmid to produce a non-shuttle plasmid.

The operation in each step may be performed in accordance with known method as described in literatures.

The gene transfer carrier for treating an anaerobic disease of the present invention may be produced by transforming any anaerobic bacterium to be transformed using said transforming plasmid of the present invention, according to known methods in the art of genetic engineering.

Because the anaerobic bacterium transformed with a transforming plasmid of the present invention is to be used for a therapeutic agent for an anaerobic disease such as solid tumor, it must be an obligate anaerobic and avirulent. Thus, it may be a virulent bacterium such as *Clostridium* or *Salmonella* that has been made avirulent, or it may be a facultative anaerobic bacterium such as *Lactobacillus* that has been mutated to an obligate anaerobic.

Preferably it includes an avirulent anaerobic bacterium, more preferably an avirulent enterobacterium, and among those *Bifidobacterium* is most preferred.

*Bifidobacterium* includes, for example, *Bifidobacterium adolescentis*, *Bifidobacterium angulatum*, *Bifidobacterium animalis*, *Bifidobacterium asteroides*, *Bifidobacterium bifidum*, *Bifidobacterium boum*, *Bifidobacterium breve*, *Bifidobacterium catenulatum*, *Bifidobacterium choerinum*, *Bifidobacterium coryneforme*, *Bifidobacterium cuniculi*, *Bifidobacterium denticolens*, *Bifidobacterium dentium*, *Bifidobacterium gallicum*, *Bifidobacterium gallinarum*, *Bifidobacterium globosum*, *Bifidobacterium indicum*, *Bifidobacterium infantis*, *Bifidobacterium inopinatum*, *Bifidobacterium lactis*, *Bifidobacterium lactentis*, *Bifidobacterium liberorum*, *Bifidobacterium longum*, *Bifidobacterium magnum*, *Bifidobacterium merycicum*, *Bifidobacterium minimum*, *Bifidobacterium mongoliense*, *Bifidobacterium parvulorum*, *Bifidobacterium pseudocatenulatum*, *Bifidobacterium pseudolongum*, *Bifidobacterium psychroaerophilum*, *Bifidobacterium pullorum*, *Bifidobacterium ruminale*, *Bifidobacterium ruminantium*, *Bifidobacterium saeculare*, *Bifidobacterium scardovii*, *Bifidobacterium subtile*, *Bifidobacterium suis*, *Bifidobacterium thermacidophilum*, *Bifidobacterium thermophilum*, and *Bifidobacterium longum* is most preferred.

These bacteria are all commercially available or readily available from a depository organization. For example, those such as *Bifidobacterium longum* ATCC-15707, *Bifidobacterium bifidum* ATCC-11863 and *Bifidobacterium infantis*

ATCC-15697 can readily be obtained from ATCC (The American Type Culture Collection).

Strains of each bacterium are not particularly limited. For example, strains of *Bifidobacterium longum* may include strains of *Bifidobacterium longum* 105-A, *Bifidobacterium longum* aE-194b, *Bifidobacterium longum* bs-601 and *Bifidobacterium longum* M101-2, among which *Bifidobacterium longum* 105-A strain is preferred.

Strains of *Bifidobacterium breve* may include for example *Bifidobacterium breve* standard strain (JCM1192), *Bifidobacterium breve* aS-1 and *Bifidobacterium breve* I-53-8W strains, among which *Bifidobacterium breve* standard strain and *Bifidobacterium breve* aS-1 strain are preferred.

Strains of *Bifidobacterium infantis* may include for example *Bifidobacterium infantis* standard strain (JCM1222) and *Bifidobacterium infantis* I-10-5 strain, among which *Bifidobacterium infantis* standard strain and *Bifidobacterium infantis* I-10-5 strain are preferred.

Strains of *Bifidobacterium lactentis* may include for example *Bifidobacterium lactentis* standard strain (JCM1210).

The gene transfer carrier of the present invention is a gene transfer carrier consisting of said anaerobic bacterium transformed with the transforming plasmid of the present invention, being capable of growing in a tissue in an anaerobic environment, and being capable of expressing a protein having an activity of interest, and having no possibility of being horizontally transferred to a pathogenic or aerobic or facultative anaerobic bacterium other than the transformed bacterium.

The production of the gene transfer carrier of the present invention may be carried out according to methods described in commercially available experiment protocols such as "IDENSHI MANUAL" (Kodan-sha), "IDENSHI-SOUSA JIKKEN HOU", Y. Takagi ed., (Kodan-sha), "Molecular Cloning", Cold Spring Harbor Laboratory, 1982, "Molecular Cloning", 2nd ed., Cold Spring Harbor Laboratory, 1989 and Methods in Enzymol., 194, 1991.

The pharmaceutical composition of the present invention is not particularly limited as long as it comprises a gene transfer carrier of the present invention. Also, the therapeutic agent of the present invention for an anaerobic disease is not particularly limited as long as it comprises a gene transfer carrier of the present invention.

Also, the pharmaceutical composition or therapeutic agent for an anaerobic disease of the present invention may comprise two or more of the gene transfer carriers of the present invention.

Moreover, the pharmaceutical composition or therapeutic agent for an anaerobic disease of the present invention may be used in combination with a pharmaceutical composition or therapeutic agent for the anaerobic disease comprising a compound exhibiting a therapeutic effect for the anaerobic disease other than the gene transfer carrier of the present invention.

Moreover, the pharmaceutical composition or therapeutic agent for an anaerobic disease of the present invention may comprise an optional ingredient other than the gene transfer carrier of the present invention as long as it does not interfere with the effect of the present invention. Such optional ingredient includes for example such as a pharmacologically acceptable carrier, excipient or diluent.

The dosage form of the pharmaceutical composition or therapeutic agent for an anaerobic disease of the present invention is not particularly limited, and may include, for example, a liquid or solid formulation comprising a gene transfer carrier of the present invention. A liquid may be produced by purifying the culture medium of an anaerobic bacterium of the gene transfer carrier of the present invention, adding thereto an appropriate physiological saline or fluid replacement or pharmaceutical additives as required, then filling it into an ample or vial. A solid formulation may be produced by adding into a liquid an appropriate protective agent and filling it into an ample or vial before lyophilizing or L-drying it, or by adding into a liquid an appropriate protective agent and lyophilizing or L-drying it before filling it into an ample or vial. Method for administrating the pharmaceutical composition or therapeutic agent for an anaerobic disease of the present invention may be either oral or parenteral administration, although parenteral administration is preferred, such as, for example, an intravenous injection, subcutaneous injection, topical infusion or intraventricular administration, and an intravenous injection is most preferred.

A dosage of gene transfer carrier of the pharmaceutical composition or therapeutic agent for an anaerobic disease of the present invention is not particularly limited as long as it is an amount sufficient to allow the growth in a disease site and the expression of the active protein of a therapeutically effective amount, although, in view of cost and avoiding the side effects as much as possible, it is preferred to be as small as possible within a range such that a desired therapeutic effect can be achieved.

A dosage of gene transfer carrier of the pharmaceutical composition or therapeutic agent for an anaerobic disease of the present invention may appropriately be selected according to the severity of the disease, the body weight, age and sex of the patient, and may appropriately be increased or decreased according to the level of improvement.

For instance, when a therapeutic agent of the present invention for an anaerobic disease is used as a therapeutic agent for solid tumor, the dosage is set with respect to such as the antitumor activity of the anaerobic bacterium itself to be used, the type of the protein having an antitumor activity produced by the anaerobic bacterium to be used, the therapeutically effective amount of the antitumor substance converted from the antitumor substance precursor, and the production of the active protein by the anaerobic bacterium to be used.

In specific, in the case of an intravenous administration, for example, it is particularly desired to decrease the risk of embolization by bacterial mass. Therefore, a preference is given to either a plurality of separate injection of an injectable formulation at a concentration as low as possible, or a continuous infusion of a dilution with an appropriate fluid replacement. For example, in an adult, the bacterial cells of the anaerobic bacterium of the invention are administered at $10^6$ to $10^{12}$ cfu per 1 kg of the body weight, once to several times per day, for one to several days, either continuously or with appropriate intervals. More specifically, 1 to 1000 mL per an adult of a formulation containing the bacterial cells of *Bifidobacterium* of the invention at $10^4$ to $10^{10}$ cfu/mL is administered, either directly or in dilution with an appropriate fluid replacement, once to several times per day, for one to several days.

In case of a topical administration for direct administration to a disease tissue, it is desired that the bacteria colonizes and proliferate throughout the disease tissue as broadly as possible. Therefore, it is desired to administer an injection at a high concentration to a plurality of sites in the disease tissue. For example, in an adult, the bacterial cells of *Bifidobacterium* of the invention are administered at $10^6$ to $10^{12}$ cfu per 1 kg of the body weight, once to several times per day, for one to several days as required, either continuously or with appropriate intervals. More specifically, 1 to 1000 mL per an adult of a formulation containing the bacterial cells of *Bifidobac-*

*terium* of the invention at $10^4$ to $10^{10}$ cfu/mL is administered, several times per day, for one to several continuous days as required.

If the loss of bacteria is confirmed during the treatment period, the treatment is temporally suspended, and bacteria are administered as above.

A "combination of X and Y" herein encompasses both cases in which X and Y are in different forms and in which X and Y are in the same form (for example, a form comprising X and Y). In the case in which X and Y are in different forms, either of X and Y may further comprise other ingredients.

The pharmaceutical composition or therapeutic agent for an anaerobic disease of the present invention may be applied to a disease in an anaerobic environment, preferable to various solid tumors. Solid tumor may include such as, for example, colorectal cancer, brain tumor, head and neck cancer, breast cancer, lung cancer, esophageal cancer, gastric cancer, liver cancer, gallbladder cancer, bile duct cancer, pancreatic cancer, pancreatic islet cell carcinoma, choriocarcinoma, colon cancer, renal cell carcinoma, adrenocortical cancer, bladder cancer, testicular cancer, prostate cancer, testicular tumor, ovarian cancer, uterine cancer, choriocarcinoma, thyroid cancer, malignant carcinoid tumor, skin cancer, malignant melanoma, osteosarcoma, soft tissue sarcoma, neuroblastoma, Wilms' tumor, retinoblastoma, melanoma and squamous cell carcinoma.

Other diseases in an anaerobic environment may include such as, for example, ischemic diseases such as myocardial infarction or arteriosclerosis obliterans, or lower limb ischemic diseases such as Buerger's disease.

The present invention also encompasses a novel secretory signal peptide useful in particular for a use in foregoing plasmid, gene transfer carrier or pharmaceutical composition. The inventors first performed a genomic analysis of *Bifidobacterium longum* 105A which is a parent strain of foregoing transformed *Bifidobacterium*, in order to discover a secretory signal peptide that functions in *Bifidobacterium* and exerts an excellent secretory effect of the expressed protein. The inventors then chose 25 proteins which had a secretory signal but not have a transmembrane region, therefore being assumed to be secretory proteins. Of the 25 proteins, 16 had a secretory signal adjacent to a promoter, whereas 9 had a secretory signal not adjacent to a promoter.

The nucleotide sequences of the coding region of the 25 proteins were investigated. The regions expected to be secretory signals and promoters were cloned, as described below, for 22 secretory proteins (Nos. 1-16, 19, 21-25) out of 25 excluding 3 (Nos. 17, 18 and 20) which were assumed to be defective protein coding sequences (CDSs).

For 16 proteins in which a secretory signal is adjacent to a promoter, the regions expected to be the promoter (promoter X) and secretory signal (hereinbelow referred to as SPxA) were cloned and combined to a gene encoding UV-optimized green fluorescent protein mutant (GFPuv; CLONTECH Laboratories, Inc.) and a terminator of histone-like peptide (HU) of *Bifidobacterium* used in plasmid production described in Patent literatures 7 to 9 above to generate a plasmid, and the secretory function of the expressed protein (GFP) was confirmed for *Bifidobacterium* transformed with the plasmid (pSPxA).

Also, for all 22 proteins including the 9 rest proteins in which a secretory signal is not adjacent to a promoter, the secretory signal regions not including promoters (hereinbelow referred to as SPxB) were cloned and combined to a promoter of histone-like peptide (HU) of *Bifidobacterium* above, a gene encoding green fluorescent protein and the terminator of histone-like peptide (HU) of *Bifidobacterium* above (HU terminator) to generate a plasmid, and the secretory function of the expressed protein (GFP) was confirmed for *Bifidobacterium* transformed with the plasmid (pSPxB) as described above.

The results confirmed that 12 plasmids (pSP7A-GFP, pSP12A-GFP, pSP1B-GFP, pSP2B-GFP, pSP3B-GFP, pSP4B-GFP, pSP7B-GFP, pSP9B-GFP, pSP10B-GFP, pSP12B-GFP, pSP16B-GFP, and pSP23B-GFP) showed secreting tendency, and 4 plasmids (pSP7A-GFP, pSP3B-GFP, pSP7B-GFP, and pSP23B-GFP) demonstrated an excellent secreting function of the expressed protein.

Furthermore, in the genomic analysis of the *Bifidobacterium longum* 105A, a search was made for a protein showing a nucleotide sequence with a high homology at amino acid level to Sec2 gene whose secretion in *Bifidobacterium breve* has been reported (Laura E. MacConaill et al., Applied and Environmental Microbiology, 2003 Vol. 69: pp 6994-7001), and its secretory signal peptide was also investigated. Namely, a gene encoding said secretory signal peptide was cloned in combination with a promoter of histone-like peptide (HU) of *Bifidobacterium* above (HU promoter), and combined with a gene encoding green fluorescent protein (GFP) and the terminator of histone-like peptide (HU) of *Bifidobacterium* above (HU terminator) to generate a plasmid, and the secretory function of the expressed protein (GFP) was confirmed for *Bifidobacterium* transformed with the plasmid (pSec2-GFP) as described above, confirming an excellent secreting function of the expressed protein.

Next, for 13 plasmids whose secreting tendency was confirmed above, plasmids in which the gene encoding GFP was replaced with an insert of a gene encoding human TNF-α, another protein of interest, which were then used to transform *Bifidobacterium* and their function to secrete the expressed protein was confirmed.

The results confirmed that 9 plasmids (pSP7A-TNFα, pSP1B-TNFα, pSP3B-TNFα, pSP4B-TNFα, pSP7B-TNFα, pSP12B-TNFα, pSP16B-TNFα, pSP23B-TNFα, and pSec2B-TNFα) showed secreting function, and 2 plasmids (pSP3B-TNFα, pSP23B-TNFα) demonstrated particularly good secreting function of the expressed protein.

Furthermore, from these plasmids, plasmids in which replication origins that function in bacteria other than *Bifidobacterium*, e.g., pUC Ori, were removed were generated. These plasmid was used for transforming *Bifidobacterium* and their secreting function of the expressed protein was confirmed. It was confirmed that the plasmids in which pUC Ori, a replication origin that functions in bacteria other than *Bifidobacterium*, has been removed could also exert a similarly excellent secreting function of the expressed protein.

Accordingly, the inventors discovered a novel secretory signal peptide which functions at least in *Bifidobacterium* and which exhibits an excellent secreting function of the expressed protein.

As mentioned above, the secretory signal peptide of the invention has an excellent secretory activity, and functions in *Bifidobacterium*, an avirulent, obligate anaerobic bacterium, and is therefore particularly suitable for a use in the plasmid, gene transfer carrier or pharmaceutical composition described above. Accordingly, the plasmid, gene transfer carrier or pharmaceutical composition described above in any embodiment comprising the novel secretory signal peptide of the present invention are also encompassed in the present invention.

EXAMPLES

Hereinbelow, the present invention is illustrated more specifically by production examples and working examples, although the technical scope of the present invention is not to be limited by these examples.

Reference Example 1

In Silico Screening of Secretory Signals

For 1941 amino acid sequences in entire translational region predicted from the whole genome sequence of *Bifidobacterium longum* 105A, signal peptides prediction using PrediSi was performed and 188 signal peptides were predicted. The prediction employed a parameter set for Gram Positive Bacteria.

Among the 188 signal peptides predicted, 25 which did not have a transmembrane region were chosen as secretory protein candidates. Their putative secretory protein coding regions are shown in Table 1.

TABLE 1

Positions and directions of secretory protein candidates in the genome

| Candidate No. | Operon | Position, direction |
|---|---|---|
| 1 | head | 20020 -> 20982 |
| 2 | head | 762462 -> 763787 |
| 3 | head | 781649 -> 782512 |
| 4 | head | 842877 -> 844577 |
| 5 | head | 1433216 -> 1433650 |
| 6 | head | 1662965 -> 1664209 |
| 7 | head | 1917150 -> 1917836 |
| 8 | head | 164213 <- 165142 |
| 9 | head | 636847 <- 637464 |
| 10 | head | 752108 <- 752839 |
| 11 | head | 839663 <- 841006 |
| 12 | head | 1201317 <- 1202642 |
| 13 | head | 1744372 <- 1744605 |
| 14 | head | 1958176 <- 1958493 |
| 15 | head | 2225694 <- 2227349 |
| 16 | head | 2258216 <- 2258665 |
| 17 | not head | 58769 -> 59881 |
| 18 | not head | 471365 -> 472411 |
| 19 | not head | 768637 -> 768834 |
| 20 | not head | 695274 <- 696701 |
| 21 | not head | 708157 <- 708966 |
| 22 | not head | 930317 <- 931657 |
| 23 | not head | 1115148 <- 1116155 |
| 24 | not head | 1326094 <- 1327137 |
| 25 | not head | 1867821 <- 1868807 |

Production Example 1

Construction of a Secretory GFP-Expressing Plasmid (pSPxA-GFP)

We constructed a plasmid that expresses secretory GFP by a promoter of a signal peptide candidate. A summary is shown in FIG. 1. Details are provided below.

Insert Preparation

Among the 25 secretory protein candidates, for 16 whose gene are located on the head of the operon (Table 1, Nos. 1 to 16), putative signal peptide portions comprising a promoter and 60 to 90 nucleotides downstream thereof were amplified by PCR method as described below.

Forward primers were designed 300 bps upstream of the translation start site and reverse primers were designed 60 to 90 bps downstream of the DNAs encoding the signal peptides. 30 ng of the genomic DNA of *Bifidobacterium longum* 105A was used as template for PCR using 2× Phusion Flash PCR Master mix (FINNZYMES).

The PCR program was as follows: 98° C. for 10 seconds, then 30 cycles of 98° C. for 1 second plus 55° C. for 5 seconds plus 72° C. for 9 seconds, and 72° C. for 1 minute. PCR primers for each signal peptide are shown in Table 2.1. 15 nucleotides on 5' side of each primer have a homologous sequence to those of the vectors shown below.

TABLE 2.1

Primers for amplification of signal peptides (SPxA)

| No. | Primer Name | Sequence (5' -> 3') | PCR product name |
|---|---|---|---|
| 1 | SP1_F1_primer | cttttctacggatccTCTCGTGTACGCGAATACG (SEQ ID NO: 52) | SP1A |
|  | SP1_R1_primer | ctcctcgcccttggaTTCCACGCGCTCCTTGG (SEQ ID NO: 53) |  |
| 2 | SP1_F2_primer | cttttctacggatccCGCGCTGCAATGGCGTCGG (SEQ ID NO: 54) | SP2A |
|  | SP1_R2_primer | ctcctcgcccttggaCAAAAACAGCACGCGGGTG (SEQ ID NO: 55) |  |
| 3 | SP1_F3_primer | cttttctacggatccGGCGTCTGGCAGCGCACAG (SEQ ID NO: 56) | SP3A |
|  | SP1_R3_primer | ctcctcgcccttggaGGCGATGGTCAGCTTGC (SEQ ID NO: 57) |  |
| 4 | SP1_F4_primer | cttttctacggatccATCAGAGGAGCCGGTGC (SEQ ID NO: 58) | SP4A |
|  | SP1_R4_primer | ctcctcgcccttggaGCCGAACAGACGCGGGGG (SEQ ID NO: 59) |  |

TABLE 2.1-continued

Primers for amplification of signal peptides (SPxA)

| No. | Primer Name | Sequence (5' -> 3') | PCR product name |
|---|---|---|---|
| 5 | SP1_F5_primer | cttttctacggatccCTCGCGGGCTTGGCGGTC (SEQ ID NO: 60) | SP5A |
|   | SP1_R5_primer | ctcctcgcccttggaTTGGTCGATGATGGCCTTG (SEQ ID NO: 61) | |
| 6 | SP1_F6_primer | cttttctacggatccGTTCGGGTCCGGGTGCGG (SEQ ID NO: 62) | SP6A |
|   | SP1_R6_primer | ctcctcgcccttggaATCGACAATAGGACTTTTCC (SEQ ID NO: 63) | |
| 7 | SP1_F7_primer | cttttctacggatccAGGCGGTCCATGGTGGATG (SEQ ID NO: 64) | SP7A |
|   | SP1_R7_primer | ctcctcgcccttggaGGTGGAGGTGGATTCGG (SEQ ID NO: 65) | |
| 8 | SP1_F8_primer | cttttctacggatccAACCATTCGGACGCGCAG (SEQ ID NO: 66) | SP8A |
|   | SP1_R8_primer | ctcctcgcccttggaCATCGTTGCCTCGCCCG (SEQ ID NO: 67) | |
| 9 | SP1_F9_primer | cttttctacggatccCCAGGGCCCGAAGGAAGAG (SEQ ID NO: 68) | SP9A |
|   | SP1_R9_primer | ctcctcgcccttggaGACGATCTGATGCGCCAGC (SEQ ID NO: 69) | |
| 10 | SP1_F10_primer | cttttctacggatccCAGCCCATCGCTATGGAG (SEQ ID NO: 70) | SP10A |
|   | SP1_R10_primer | ctcctcgcccttggaTCGCTGCTTGAGTTTGCCG (SEQ ID NO: 71) | |
| 11 | SP1_F11_primer | cttttctacggatccTCTGTAGCGGGAGGTTGCG (SEQ ID NO: 72) | SP11A |
|   | SP1_R11_primer | ctcctcgcccttggaCAGCGTGGGCTCCCAAGCC (SEQ ID NO: 73) | |
| 12 | SP1_F12_primer | cttttctacggatccGCGTTACTTCCATGTTCGC (SEQ ID NO: 74) | SP12A |
|   | SP1_R12_primer | ctcctcgcccttggaGGAACGGGTCCACAGGGTG (SEQ ID NO: 75) | |
| 13 | SP1_F13_primer | cttttctacggatccCCTTCTCAACGCCAGCGGC (SEQ ID NO: 76) | SP13A |
|   | SP1_R13_primer | ctcctcgcccttggaAGACTCGCTAGCACAGCAC (SEQ ID NO: 77) | |
| 14 | SP1_F14_primer | cttttctacggatccGACATAGCGCGGTTTCATACC (SEQ ID NO: 78) | SP14A |
|   | SP1_R14_primer | ctcctcgcccttggaTTGGGCCACTATTGTCTTC (SEQ ID NO: 79) | |
| 15 | SP1_F15_primer | cttttctacggatccACCGGCACCTGCGCCGGCG (SEQ ID NO: 80) | SP15A |
|   | SP1_R15_primer | ctcctcgcccttggaCTTGCCTGAGGCATCTTG (SEQ ID NO: 81) | |
| 16 | SP1_F16_primer | cttttctacggatccATCGCAACACCTCCATATTGTTCC (SEQ ID NO: 82) | SP16A |
|   | SP1_R16_primer | ctcctcgcccttggaGGCCAACGGAGTCGTCTCG (SEQ ID NO: 83) | |

Analyses of a part of PCR product using 2% agarose gel (1×TBE buffer, with ethidium bromide) confirmed a single band of putative size.

When a single band was not confirmed, annealing temperature was changed from 55° C. to 60° C. and performed PCR once more.

PCR products were purified using PCR product purification kit (QIAquick PCR purification kit, QIAGEN) and purified PCR products were quantified by absorption photometer.

A signal peptide fragment comprising its own promoter region is named as a signal peptide xA (SPxA) (x=1 to 16).

Vector Preparation

Vectors for cloning SPxA were prepared as follows. A summary of the preparation is shown in FIG. 1. Plasmid pAmyB-GFPuv vector (FIG. 1, top panel, right figure; SEQ ID No.: 1) was completely digested with BamHI and Eco147I (both from Fermentas). Reacting condition was in accordance with the instruction for use of the enzymes. Digested plasmid was fractioned by electrophoresis on 0.8% agarose gel for purification (1×TBE buffer, with ethidium bromide), a large fragment of approximately 4.2 kbps was cut out, and DNA was extracted from agarose and purified using DNA extraction kit from a gel (QIAquick Gel Extraction Kit, QIAGEN). Purified DNA fragment (vector) was electrophoresed on 0.8% agarose gel (1×TBE buffer, with ethidium bromide) with a DNA concentration marker to estimate its concentration.

For GFPuv coding sequence in pAmyB-GFPuv vector, codons have been optimized (GenScript) for *Bifidobacterium*.

Recombination Reaction

The vector and insert prepared above were mixed in 1:3 to 10 molar ratio, and linked by recombination reaction (CloneEZ Kit, GenScript). Reacting conditions were in accordance with the product instruction.

Transformation of *E. coli*

*E. coli* TOP10 chemically Competent Cell (Life Technologies Japan) was transformed using 2 μL of the recombination reaction solution above, smeared onto a LB (containing 75 μg/mL spectinomycin) plate and cultured overnight at 37° C. Transforming conditions were in accordance with the product instruction.

The transformed *E. coli* colonies were cultured overnight in a LB (containing 75 μg/mL spectinomycin) liquid medium at 37° C., and plasmid was extracted from the culture (QIAprep Spin Miniprep Kit, QIAGEN). The insert sequence in this plasmid was determined, and the plasmid was named as pSPxA-GFP (x=1 to 16).

Transformation of *Bifidobacterium*

3 to 5 μL of the plasmid DNA extracted from transformed *E. coli* above was used for transforming *Bifidobacterium longum* 105A by electroporation system (Gene Pulser II, Bio-Rad Laboratories). Immediately after an electric shock, a mixture of 800 μL of IMR liquid medium and 50 μL of vitamin C additive solution was added to the cuvette, which was then collected in a sterilized 2 mL microtube. Similar manipulation was performed for each tube, before loosening the lid of these 2 mL tubes and placing in a dessicator. The dessicator was deaerated by a vacuum pump and filled with carbon dioxide. This manipulation was repeated three times to replace the air in the dessicator with carbon dioxide, before placing the dessicator in an incubator set to 37° C. and incubating for 3 hours.

After the incubation, each bacterial suspension was mixed thoroughly, and 100 μL thereof was measured and smeared to two IMR agar media (containing 75 μg/mL SPCM). These plates were placed in a sealed vessel with deoxygenating/ carbon dioxide-generating agent (Anaero Pac®-Anaero, MITSUBISHI GAS CHEMICAL, INC.) and cultured for two days in an incubator set to 37° C.

Production Example 2

Construction of a Secretory GFP-Expressing Plasmid (pSPxB-GFP)

Figure 2:
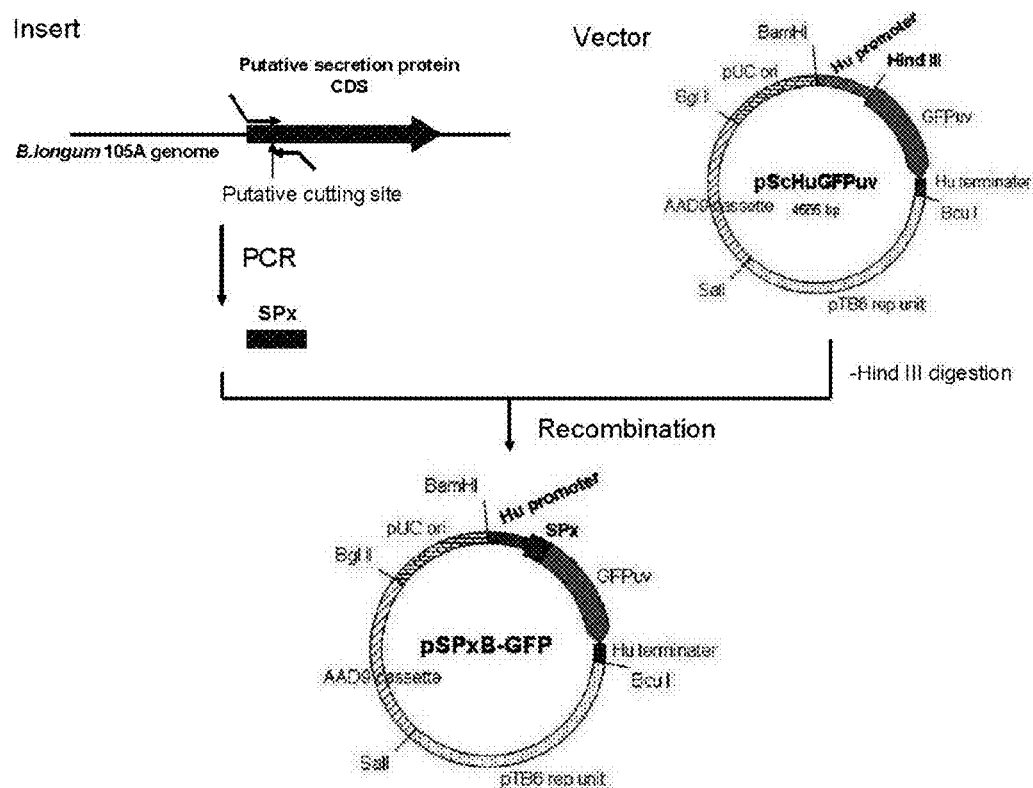
FIG. 2 is a map showing a summary of the construction of a secretory GFP-expressing plasmid (pSPxB-GFP).

A plasmid that expresses secretory GFP by histone-like promoter (HU promoter) of *Bifidobacterium*. A summary is shown in FIG. 2. Details are given below.

Insert Preparation

Among the 25 secretory protein candidates above, for 22 candidates (Nos. 1-16, 19, 21-25) excluding 3 (Nos. 17, 18, 20) that were assumed to be deficient protein coding sequences, DNA fragments containing the putative signal peptide coding parts and 60 to 90 nucleotides downstream thereof were amplified by PCR.

Forward primers were designed at the translation start site and reverse primers were designed at 60 to 90 nucleotides downstream of the DNA encoding the signal peptides. PCR primers for each signal peptide are shown in Table 2.2. 15 nucleotides at 5' side of each primer have a homologous sequence to the vector shown below.

TABLE 2.2

Primers for amplification of signal peptides (SPx)

| | Primer Name | Sequence (5' -> 3') | PCR product |
|---|---|---|---|
| 1 | SP1_F2_primer | caagaaggatgctttATGGCGGAAACTACCGTTAAGC (SEQ ID NO: 84) | SP1 |
| | SP1_R1_primer | ctcctcgcccttggaTTCCACGCGCTCCTTGG (SEQ ID NO: 53) | |
| 2 | SP2_F2_primer | caagaaggatgctttGTGGGTATGACTGAGAACG (SEQ ID NO: 85) | SP2 |
| | SP1_R2_primer | ctcctcgcccttggaCAAAAACAGCACGCGGGTG (SEQ ID NO: 55) | |
| 3 | SP3_F2_primer | caagaaggatgctttATGTTCAATAAGCGACAC (SEQ ID NO: 86) | SP3 |
| | SP1_R3_primer | ctcctcgcccttggaGGCGATGGTCAGCTTGC (SEQ ID NO: 57) | |
| 4 | SP4_F2_primer | caagaaggatgctttATGACCACTCACAACAGC (SEQ ID NO: 87) | SP4 |
| | SP1_R4_primer | ctcctcgcccttggaGCCGAACAGACGCGGGGG (SEQ ID NO: 59) | |
| 5 | SP5_F2_primer | caagaaggatgctttATGACCGCGATTGACGAG (SEQ ID NO: 88) | SP5 |
| | SP1_R5_primer | ctcctcgcccttggaTTGGTCGATGATGGCCTTG (SEQ ID NO: 61) | |
| 6 | SP6_F2_primer | caagaaggatgctttATGAAGATTGCGGTTGCAGG (SEQ ID NO: 89) | SP6 |
| | SP1_R6_primer | ctcctcgcccttggaATCGACAATAGGACTTTTCC (SEQ ID NO: 63) | |

TABLE 2.2-continued

Primers for amplification of signal peptides (SPx)

| | Primer Name | Sequence (5' -> 3') | PCR product |
|---|---|---|---|
| 7 | SP7_F2_primer | caagaaggatgctttATGTTTGCGTGCGTAGCC (SEQ ID NO: 90) | SP7 |
| | SP1_R7_primer | ctcctcgcccttggaGGTGGAGGTGGATTCGG (SEQ ID NO: 65) | |
| 8 | SP8_F2_primer | caagaaggatgctttATGGTTGGTGACGACACC (SEQ ID NO: 91) | SP8 |
| | SP1_R8_primer | ctcctcgcccttggaCATCGTTGCCTCGCCCG (SEQ ID NO: 67) | |
| 9 | SP9_F2_primer | caagaaggatgctttATGGGCACCATGATGCG (SEQ ID NO: 92) | SP9 |
| | SP1_R9_primer | ctcctcgcccttggaGACGATCTGATGCGCCAGC (SEQ ID NO: 69) | |
| 10 | SP10_F2_primer | caagaaggatgctttATGATGACTGGTGCACAGG (SEQ ID NO: 93) | SP10 |
| | SP1_R10_primer | ctcctcgcccttggaTCGCTGCTTGAGTTTGCCG (SEQ ID NO: 71) | |
| 11 | SP11_F2_primer | caagaaggatgctttATGAAGTTCACCGTTGC (SEQ ID NO: 94) | SP11 |
| | SP1_R11_primer | ctcctcgcccttggaCAGCGTGGGCTCCCAAGCC (SEQ ID NO: 73) | |
| 12 | SP12_F2_primer | caagaaggatgctttATGGTGTCTTTCAATAAACTGACC (SEQ ID NO: 95) | SP12 |
| | SP1_R12_primer | ctcctcgcccttggaGGAACGGGTCCACAGGGTG (SEQ ID NO: 75) | |
| 13 | SP13_F2_primer | caagaaggatgctttATGGTCGCCGTCCTCAGG (SEQ ID NO: 96) | SP13 |
| | SP1_R13_primer | ctcctcgcccttggaAGACTCGCTAGCACAGCAC (SEQ ID NO: 77) | |
| 14 | SP14_F2_primer | caagaaggatgctttTTGCCGGGACCTATATGTCC (SEQ ID NO: 97) | SP14 |
| | SP1_R14_primer | ctcctcgcccttggaTTGGGCCACTATTGTCTTC (SEQ ID NO: 79) | |
| 15 | SP15_F2_primer | caagaaggatgctttATGAAACGTAGCGATTATATGTTGG (SEQ ID NO: 98) | SP15 |
| | SP1_R15_primer | ctcctcgcccttggaCTTGCCTGAGGCATCTTG (SEQ ID NO: 81) | |
| 16 | SP16_F2_primer | caagaaggatgctttATGAGCAATAGTGCATCATCG (SEQ ID NO: 99) | SP16 |
| | SP1_R16_primer | ctcctcgcccttggaGGCCAACGGAGTCGTCTCG (SEQ ID NO: 83) | |
| 19 | SP19_F2_primer | caagaaggatgctttTTGGCAAGATGGGTCACTC (SEQ ID NO: 100) | SP19 |
| | SP19_R2_primer | ctcctcgcccttggaGCCCATGACCGGCATGAAC (SEQ ID NO: 101) | |
| 21 | SP21_F2_primer | caagaaggatgctttATGGCATTGACTGATGAACAGG (SEQ ID NO: 102) | SP21 |
| | SP21_R2_primer | ctcctcgcccttggaACGTGCAGTGGTATGGATG (SEQ ID NO: 103) | |
| 22 | SP22_F2_primer | caagaaggatgctttTTGGTGTCTATGAGAAGC (SEQ ID NO: 104) | SP22 |
| | SP22_R2_primer | ctcctcgcccttggaGATGCGCTCACGCTTGG (SEQ ID NO: 105) | |
| 23 | SP23_F2A_primer | gaaggatgcttATGAACAAGCGATGGAAC (SEQ ID NO: 106) | SP23 |
| | SP23_R2_primer | ctcctcgcccttggaGATCGTCTTGAGAATCTTCAGAC (SEQ ID NO: 107) | |
| 24 | SP24_F2_primer | caagaaggatgctttATGGTCGGCATGCGCGAC (SEQ ID NO: 108) | SP24 |
| | SP24_R2_primer | ctcctcgcccttggaGTTGGTGCGGTTCCGGTAG (SEQ ID NO: 109) | |

TABLE 2.2-continued

Primers for amplification of signal peptides (SPx)

| | Primer Name | Sequence (5' -> 3') | PCR product |
|---|---|---|---|
| 25 | SP25_F2_primer | caagaaggatgctttGTGATGTTATCCACACC (SEQ ID NO: 110) | SP25 |
| | SP25_R2_primer | ctcctcgcccttggaCTGCTCATGATCGGCCCAG (SEQ ID NO: 111) | |

PCR was performed in a similar way to Production Example 1 above, and the prepared PCR products were named as SPx (x=1-16, 19, 21-25).

Vector Preparation

Vectors for cloning SPx were prepared as follows. A summary of the preparation is shown in FIG. 2. Plasmid pScHuGFPuv vector (FIG. 2, top panel, right figure; SEQ ID No.: 2) was fully digested with HindIII (Fermentas). Reacting conditions were in accordance to the instruction of the enzyme. Digested plasmid was fractioned by electrophoresis on 0.8% agarose gel for purification (1×TBE buffer, with ethidium bromide), and a straight chain DNA fragment of approximately 4.6 kbps was cut out, and DNA was extracted from agarose and purified using DNA extraction kit from a gel (QIAquick Gel Extraction Kit, QIAGEN). Purified DNA fragment (vector) was electrophoresed on 0.8% agarose gel (1×TBE buffer, with ethidium bromide) with a DNA concentration marker to estimate its concentration.

For GFPuv coding sequence in pScHuGFPuv vector, codons have been optimized (GenScript) for *Bifidobacterium*.

Recombination Reaction

The vector and insert prepared above were mixed in 1:3 to 10 molar ratio, and linked by recombination reaction (CloneEZ Kit, GenScript). Reaction conditions were in accordance with the product instruction.

Transformation of *E. coli*

*E. coli* TOP10 chemically Competent Cell (Life Technologies Japan) was transformed using 2 µL of the recombination reaction solution above, smeared onto a LB (containing 75 µg/mL spectinomycin) plate and cultured overnight at 37° C. Transforming conditions were in accordance with the product instruction.

The transformed *E. coli* colonies were cultured overnight in a LB (containing 75 µg/mL spectinomycin) liquid medium at 37° C., and plasmid was extracted from the culture (QIAprep Spin Miniprep Kit, QIAGEN). The insert sequence in this plasmid was determined, and the plasmid was named as pSPxB-GFP (x=1-16, 19, 21-25).

Transformation of *Bifidobacterium*

*Bifidobacterium* was transformed in a similar way as Production Example 1 above.

Production Example 3

Construction of a Secretory GFP-Expressing Plasmid (pSec2-GFP)

Figure 3:
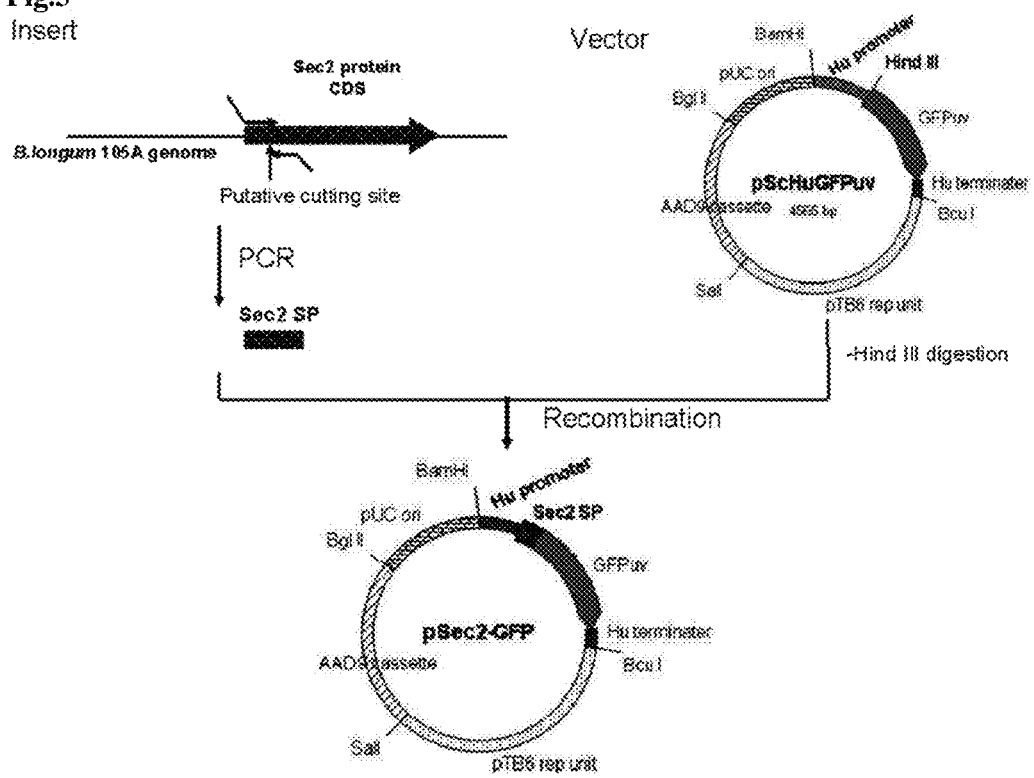
FIG. 3 is a map showing a summary of the construction of a secretory GFP-expressing plasmid (pSec2-GFP).

A secretory peptide Sec2 has been reported in *Bifidobacterium breve* UCC2003 (Laura E. MacConaill et al., Applied and Environmental Microbiology, 2003 Vol. 69: pp 6994-7001). From the genomic sequence of *B. longum* 105A, a sequence with high homology to Sec2 was searched and its secretory signal was linked to a coding sequence of GFP. A plasmid which expresses this by a HU promoter was constructed using the plasmid pScHuGFPuv vector of Production Example 2. A summary is shown in FIG. 3. Details are given below.

Insert Preparation

Sec2-F1 primer and Sec2-R2 primer were designed at the translation start site of Sec2 gene and at 123 bps downstream of the signal peptide coding sequence of *B. longum* 105A, respectively. Primer sequences are shown in Table 2.3. 15 nucleotides at 5' side of each primer have a homologous sequence to the vector shown below.

TABLE 2.3

Primers for amplification of signal peptides (Sec2)

| | Primer Name | Sequence (5' -> 3') | PCR product |
|---|---|---|---|
| Sec2 | Sec2-F1 primer | caagaaggatgctttTTGGAAC ATATGAAGATGTTCC (SEQ ID NO: 112) | Sec2 |
| | Sec2-R2 primer | ctcctcgcccttggaGTCGAGT TTCATTGTATCG (SEQ ID NO: 113) | |

PCR was performed in a similar way to Production Example 1 above, and the prepared PCR product was named as Sec2.

Vector Preparation

Preparation was in a similar way as Production Example 2 above, using a plasmid pScHuGFPuv vector (FIG. 3, top panel, right figure; SEQ ID No.: 2)

Recombination Reaction

The vector and insert prepared above were mixed in 1:10 molar ratio, linked by a recombination reaction (CloneEZ Kit, GenScript). Reacting conditions were in accordance with the product instruction.

Transformation of *E. coli*

*E. coli* TOP10 chemically Competent Cell (Life Technologies Japan) was transformed using 2 µL of the recombination reaction solution above. Transforming conditions were in accordance with the product instruction.

The transformed *E. coli* colonies were cultured overnight in a LB (containing 75 µg/mL spectinomycin) liquid medium at 37° C., and plasmid was extracted from the culture (QIAprep Spin Miniprep Kit, QIAGEN). The insert sequence in this plasmid was determined, and the plasmid was named as pSec2-GFP (SEQ ID No.: 3).

Transformation of *Bifidobacterium*

*Bifidobacterium* was transformed in a similar way as Production Example 1 above.

Working Example 1

GFP Protein Expression of Recombinant Bifidobacteria

The recombinant bifidobacteria obtained from Production Examples 1 to 3 (*Bifidobacterium longum* 105A/pSPxA-GFP (x=1-16), *Bifidobacterium longum* 105A/pSPxB-GFP (x=1-16, 19, 21-25) and *Bifidobacterium longum* 105A/pSec2-

GFP) in glycerin stock solution were inoculated at 1% in APS-2S-2.5SE (75 µg/mL spectinomycin) liquid medium and cultured in anaerobic condition at 37° C. for 24 hours (activating culture solution).

Subsequently, the activating culture solution was inoculated at 0.5% in a medium (for each 20 mL of APS-2S-2.5SE (75 µg/mL spectinomycin) liquid medium, 4 mL of 1M sodium phosphate buffer (pH6.8) was added). This was cultured in anaerobic condition at 37° C. for 18 hours.

This culture solution was used to prepare culture supernatant and intracellular proteins as follows.

The culture solution was centrifuged and then culture supernatant was collected. Proteins in this culture supernatant were precipitated by trichloroacetic acid (TCA), washed with acetone, dissolved in an electrophoresis buffer, and the proteins in the culture supernatant were concentrated. Besides, intracellular proteins were extracted as follows. 1 mL of the culture solution was mixed with 4 mL of PBS, centrifuged at 12,000 rpm for 5 minutes at 4° C., and the supernatant was removed. The precipitation was suspended in 5 mL PBS and centrifuged to remove the supernatant, which was repeated twice. After washing, the cells were made to the total volume of 1 mL with PBS, homogenized with a sonicator. After centrifugation, the supernatant was collected to provide an intracellular extract.

A similar operation was performed for wild type *Bifidobacterium longum* 105A for a negative control. For a positive control for GFP protein, recombinant GFPuv (Clontech) was used.

The culture supernatant concentrate (corresponding to 1 mL culture solution) and intracellular protein extract (corresponding to 7.5 µL culture solution) above were electrophoresed on 12.5% tris-glycine gel (ATTO Corporation, e-PA-GEL®). This was transferred to a PVDF membrane (Invitrogen, iBlot® Transfer Stacks) using iBlot® Transfer Device (Invitrogen). After blotting, the membrane was blocked, then reacted with a rabbit GFP antibody (Clontech, A.v. peptide Antibody Living Colors) as primary antibody and anti-Rabbit IgG HRP Conjugate (Santa Cruz Biotechnology) as secondary antibody, and developed with ECL Advance Western blotting Detection Kit (GE Healthcare). This was analyzed by an imaging analyzer (Fluor S Max, Bio-Rad).

Figure 4:
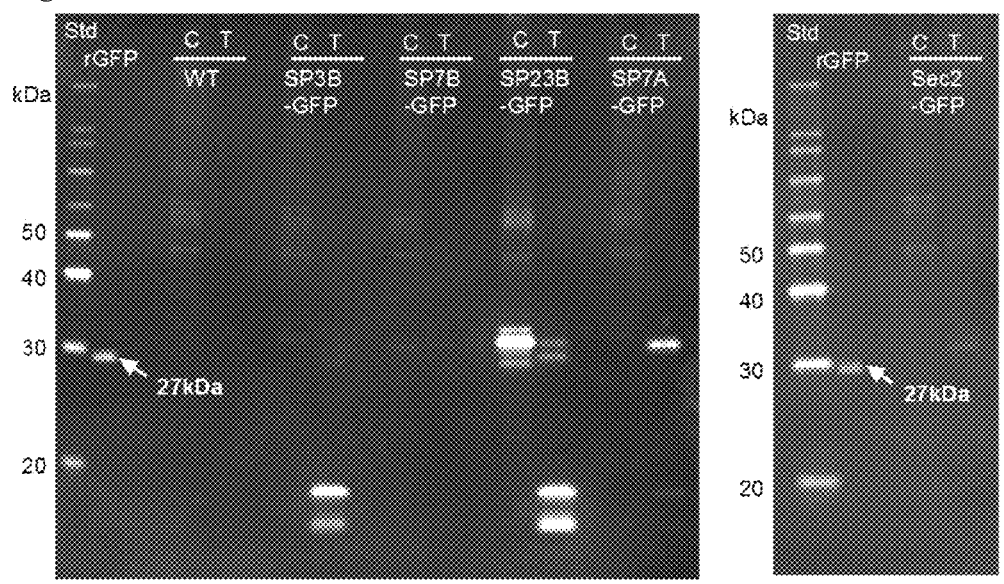
FIG. 4 is a picture showing the results of western blotting of *B. longum* 105A/pSP3B-GFP, *B. longum* 105A/pSP7B-GFP, *B. longum* 105A/pSP23B-GFP, *B. longum* 105A/pSP7A-GFP and *B. longum* 105A/pSec2-GFP. In this figure, C indicates the lane for intracellular protein extract, T indicates the lane for the culture supernatant concentrate, and the numbers on the vertical axis indicates the molecular weight (kDa).

As a result, 13 bacteria (*B. longum* 105A/pSP1B-GFP, *B. longum* 105A/pSP2B-GFP, *B. longum* 105A/pSP3B-GFP, *B. longum* 105A/pSP4B-GFP, *B. longum* 105A/pSP7B-GFP, *B. longum* 105A/pSP9B-GFP, *B. longum* 105A/pSP10B-GFP, *B. longum* 105A/pSP12B-GFP, *B. longum* 105A/pSP16B-GFP, *B. longum* 105A/pSP23B-GFP, *B. longum* 105A/pSP7A-GFP, *B. longum* 105A/pSP12A-GFP and *B. longum* 105A/pSec2-GFP) showed secreting tendency. Similar test was performed twice, and prominent secretory effect was confirmed particular in 5 (*B. longum* 105A/pSP3B-GFP, *B. longum* 105A/pSP7B-GFP, *B. longum* 105A/pSP23B-GFP, *B. longum* 105A/pSP7A-GFP and *B. longum* 105A/pSec2-GFP) (FIG. 4).

Working Example 4

Production of a Secretory TNF Alpha-Expressing *Bifidobacterium* (pSPxA-TNF Alpha and pSPxB-TNF Alpha)

Construction of Plasmid Vector pTNF1

The codons of coding sequence of human TNFα (Accession No. X01394) were optimized for *Bifidobacterium* and inserted into pUC57vector (outsource synthesis to GenScript). This plasmid was used as template for PCR (PrimeSTAR® HS Premix, TAKARA BIO, Inc.) targeting to TNFα coding region using TNF-F1 primer and TNF-R1 primer (Table 3). PCR product was purified (QIAquick PCR purification Kit, QIAGEN) and electrophoresed on 0.8% agarose gel, and a DNA fragment of approximately 0.7 kbps was cut out. DNA was extracted from this gel (QIAquick Gel Extraction Kit, QIAGEN) to provide the insert.

TABLE 3

Primers for constructing plasmid vector pTNF1

| Primers | Sequence (5' -> 3') |
|---|---|
| TNF-F1 primer | gaaggatgctttATGTCCACCGAATCCATGATCCG (SEQ ID NO: 114) |
| TNF R1 primer | acgagcagaaggTCACAGGGCGATGATGCCGAAG (SEQ ID NO: 115) |

Besides, the vector was prepared as follows. 10 µL each of the restriction enzymes FastDigest Bsp 119 I, FastDigest Pst I, FastDigest Nde I and FastDigest Acl I (Fermentas) were added to 10 µg of plasmid pCDshuttle (Patent literature 9; WO2009/128272A1) and incubated at 37° C. for 4.5 hours to fully digest the plasmid. This was electrophoresed on 0.8% agarose gel, and a DNA fragment of approximately 3.9 kbps was cut out. DNA was extracted from this gel (QIAquick Gel Extraction Kit, QIAGEN) to provide the vector.

20 ng of the vector and 36 ng of the insert above were linked by recombination of terminal sequences using CloneEZ Kit (GenScript). Details were in accordance with the product instruction of CloneEZ Kit. 2 µL of this DNA was used for transforming *E. coli* TOP10 chemically Competent Cell (Life Technologies Japan). Transforming conditions were in accordance with the product instruction.

Transformed *E. coli* colonies were cultured overnight in LB (containing 75 µg/mL spectinomycin) liquid medium at 37° C., and plasmid was extracted from this culture (QIAprep Spin Miniprep Kit, QIAGEN). This plasmid was named as pTNF1 (FIG. 5, top panel, right figure; SEQ ID No.: 4).

Figure 5:
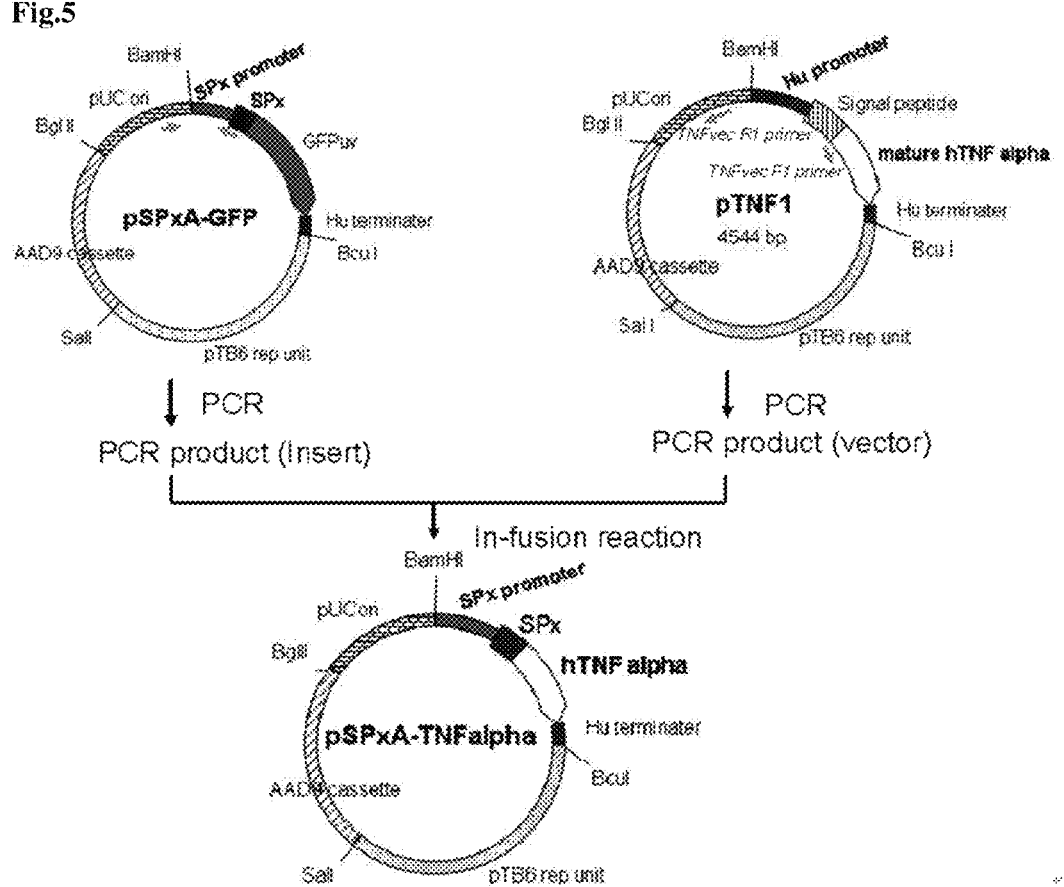
FIG. 5 is a map showing a summary of the construction of a secretory TNF alpha-expressing plasmid (pSPxA-TNF alpha).
Figure 6:
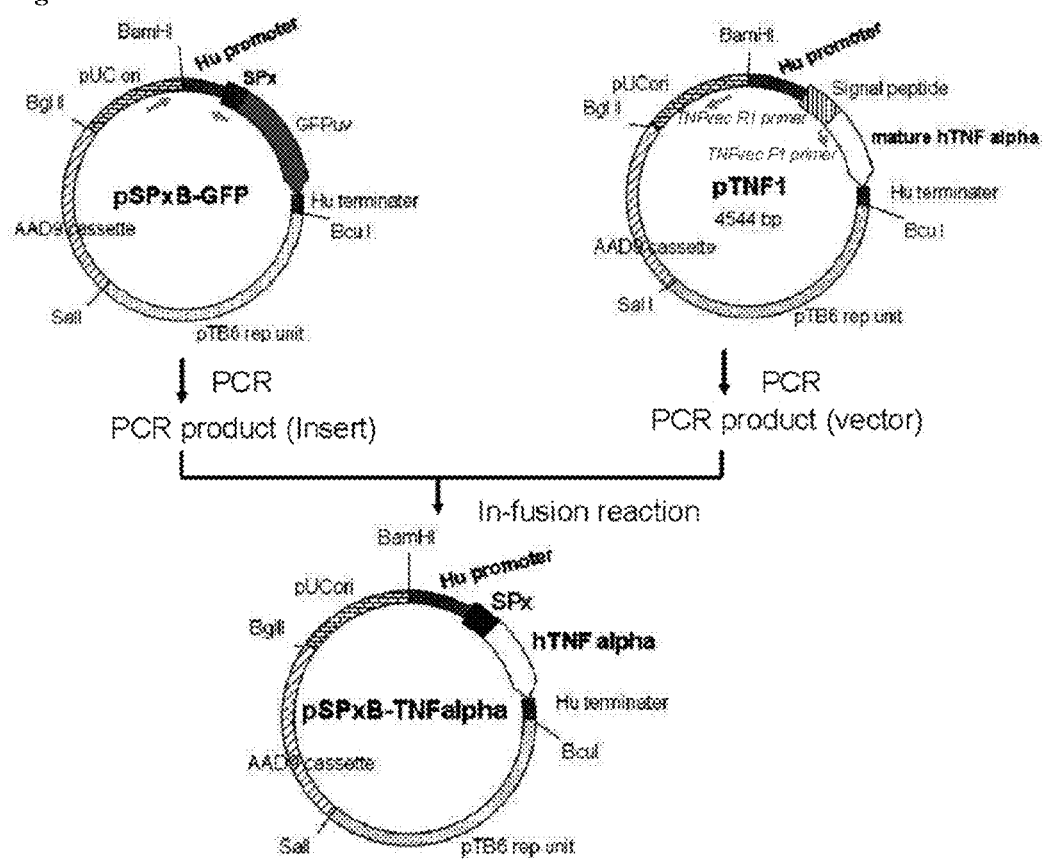
FIG. 6 is a map showing a summary of the construction of a secretory TNF alpha-expressing plasmid (pSPxB-TNF alpha).

The construction summaries of plasmids pSPxA-TNF alpha and pSPxB-TNF alpha in which the GFP portion of plasmids pSPxA-GFP and pSPxB-GFP has been replaced by TNF alpha were shown in FIGS. 5 and 6, respectively.

Plasmid pTNF1 was used as template for PCR (PrimeSTAR® HS Premix, TAKARA BIO, Inc.) using TNFvec F1 primer and TNFvec R1 primer (Table 4), and PCR product of approximately 3.8 kbps was obtained to provide the vector.

TABLE 4

Vector primers for constructing pSPxA-TNF alpha and pSPxB-TNF alpha

| Primers | Sequence (5' -> 3') |
|---|---|
| TNFvec_F1_primer | GTGCGCTCCTCCTCCCGTAC (SEQ ID NO: 116) |
| TNFvec_R1_primer | GCCGTAGTTAGGCCACCACTTCAAG (SEQ ID NO: 117) |

Besides, the plasmid pSPxA-GFP (x=7 or 12) or pSPxB-GFP (x=1-4, 7, 9, 10, 12, 16 or 23) which showed secreting tendency in Working Example 1 was used as template for PCR amplification (PrimeSTAR® HS Premix, TAKARA BIO, Inc.) of the insert using primers of Table 5, to provide the insert.

TABLE 5

Insert primers for constructing pSPxA-TNF alpha, pSPxB-TNF alpha and pSec2-TNF alpha

| PCR product for | Primers | Sequence (5' -> 3') | Template Plasmid |
|---|---|---|---|
| pSP7A-TNF | pUC_ori_F2 primer | tggcctaactacggctacac (SEQ ID NO: 118) | pSP7A-GFP |
| | SP7-TNF_R1 primer | ggaggaggagcgcacGGTGGAGGTGGATTCGG CGAAC (SEQ ID NO: 119) | |
| pSP12A-TNF | pUC_ori_F2 primer | tggcctaactacggctacac (SEQ ID NO: 118) | pSP12A-GFP |
| | SP12-TNF_R1 primer | ggaggaggagcgcacGGAACGGGTCCACAGG GTGAT (SEQ ID NO: 120) | |
| pSP1B-TNF | pUC_ori_F2 primer | tggcctaactacggctacac (SEQ ID NO: 118) | pSP1B-GFP |
| | SP1B-TNF_R1 R1 primer | ggaggaggagcgcacTTCCACGCGCTCCTTGG CGATG (SEQ ID NO: 121) | |
| pSP2B-TNF | pUC_ori_F2 primer | tggcctaactacggctacac (SEQ ID NO: 118) | pSP2B-GFP |
| | SP2B-TNF_R1 primer | ggaggaggagcgcacCAAAAACAGCACGCGG GTG (SEQ ID NO: 122) | |
| pSP3B-TNF | pUC_ori_F2 primer | tggcctaactacggctacac (SEQ ID NO: 118) | pSP3B-GFP |
| | SP3B-TNF_R1 primer | ggaggaggagcgcacGGCGATGGTCAGCTTGC (SEQ ID NO: 123) | |
| pSP4B-TNF | pUC_ori_F2 primer | tggcctaactacggctacac (SEQ ID NO: 118) | pSP4B-GFP |
| | SP4B-TNF_R1 primer | ggaggaggagcgcacGCCGAACAGACGCGGG GGAA (SEQ ID NO: 124) | |
| pSP7B-TNF | pUC_ori_F2 primer | tggcctaactacggctacac (SEQ ID NO: 118) | pSP7B-GFP |
| | SP7-TNF_R1 primer | ggaggaggagcgcacGGTGGAGGTGGATTCG GCGAAG (SEQ ID NO: | |
| pSP9B-TNF | pUC_ori_F2 primer | tggcctaactacggctacac (SEQ ID NO: 118) | pSP9B-GFP |
| | SP9B-TNF_R1 primer | ggaggaggagcgcacGACGATCTGATGCGCCA GCGCATC (SEQ ID NO: 125) | |
| pSP10B-TNF | pUC_ori_F2 primer | tggcctaactacggctacac (SEQ ID NO: 118) | pSP10B-GFP |
| | SP10B-TNF_R1 primer | ggaggaggagcgcacTCGCTGCTTGAGTTTGC CGGAAATC (SEQ ID NO: 126) | |
| pSP12B-TNF | pUC_ori_F2 primer | tggcctaactacggctacac (SEQ ID NO: 118) | pSP12B-GFP |
| | SP12-TNF_R1 primer | ggaggaggagcgcacGGAACGGGTCCACAGG GTGAT (SEQ ID NO: 120) | |
| pSP16B-TNF | pUC_ori_F2 primer | tggcctaactacggctacac (SEQ ID NO: 118) | pSP16B-GFP |
| | SP16B-TNF_R1 primer | ggaggaggagcgcacGGCCAACGGAGTCGTCTC (SEQ ID NO: 127) | |
| pSP23B-TNF | pUC_ori_F2 primer | tggcctaactacggctacac (SEQ ID NO: 118) | pSP23B-GFP |
| | SP23B-TNF_R1 primer | ggaggaggagcgcacGATCGTCTTGAGAATCTT CAGACG (SEQ ID NO: 128) | |
| pSec2-TNF | Sec2_out1_primer | tacGGATCCgtcttcctgctg (SEQ ID NO: 129) | pSec2-GFP |
| | Sec2a_R1_primer | GTACGGGAGGAGGAGCGCACGTCGAGT TTCATTGTATCG (SEQ ID NO: 130) | |
| pSec2-TNF | Sec2a_F1_primer | CGATACAATGAAACTCGACGTGCGCTCC TCCTCCCGTAC (SEQ ID NO: 131) | pTNF1 |
| | TNF_out1_primer | aggACTAGTccggaataatacgg (SEQ ID NO: 132) | |

100 ng of the vector and 40 ng of the insert above were linked by In-Fusion™ Advantage PCR Cloning Kit (TAKARA BIO, Inc.). 2 μL of this DNA was used for transforming *E. coli* TOP10 chemically Competent Cell (Life Technologies Japan). Transforming conditions were in accordance with the product instruction.

Transformed *E. coli* colonies were cultured overnight in LB (containing 75 μg/mL spectinomycin) liquid medium at 37° C., and plasmids were extracted from this culture (QIAprep Spin Miniprep Kit, QIAGEN). These plasmids were fully sequenced and their plasmid names were assigned as pSP7A-TNF alpha, pSP12A-TNF alpha, pSP1B-TNF alpha, pSP2B-TNF alpha, pSP3B-TNF alpha, pSP4B-TNF alpha, pSP7B-TNF alpha, pSP9B-TNF alpha, pSP10B-TNF alpha, pSP12B-TNF alpha, pSP16B-TNF alpha, pSP23B-TNF alpha.

Transformation of Bifidobacteria with pSPxA-TNF Alpha and pSPxB-TNF Alpha

Plasmids pSPxA-TNF alpha and pSPxB-TNF alpha were used for transforming *B. longum* 105A in a similar way as Production Example 1.

Reference Example 2

Construction of Plasmid pTNF3

We constructed a shuttle vector (*Bifidobacterium-E. coli*) in which the mature human TNFα coding sequence is located downstream of Hu promoter derived from *Bifidobacterium*. A summary is shown in FIG. 12. Details are as follows.

Insert Preparation

We constructed a plasmid human TNFalpha_in_pUC57 containing an artificial DNA having human TNFα (Accession No:X01394; from 153th to 854th nucleotides of an immature TNFα coding sequence) of which codons are optimized for *Bifidobacterium*, and Hu promoter derived from *Bifidobacterium* located upstream thereof and Hu terminator derived from *Bifidobacterium* located downstream thereof (custom-synthesized by GenScript).

1 ng of the plasmid human TNFalpha_in_pUC57 was used as template for PCR amplification of the mature TNFα portion of the TNFα coding sequence by PrimeSTAR® HS Premix (TAKARA BIO, Inc.). TNF F3 and TNF R1 primers were used, wherein the 15 nucleotides of the 5' side of each primer had a homologous sequence to the vector terminal (Table 6). The PCR program consisted of 30 cycles of 10 seconds at 98° C., 5 seconds at 60° C. and 30 seconds at 72° C., followed by 30 seconds at 72° C.

A part of PCR product was electrophoresed with DNA concentration marker on 2% agarose gel (1×TBE buffer, containing ethidium bromide), confirming a single band of approximately 0.5 kbp and estimating its concentration.

Vector Preparation 1 ng of the plasmid pCDshuttle was used as template for PCR amplification of the vector skeletal by PrimeSTAR® HS Premix (TAKARA BIO, Inc.). Primers pCDshuttle F1 and pCDshuttle R1 were used, wherein the 15 nucleotides on the 5' side of each primer had a homologous sequence to the insert terminal (Table 6). The PCR program consisted of 30 cycles of 10 seconds at 98° C., 5 seconds at 55° C. and 4 minutes at 72° C., followed by 30 seconds at 72° C.

A part of PCR product was electrophoresed with DNA concentration marker on 0.8% agarose gel (1×TBE buffer, containing ethidium bromide), confirming a single band of approximately 3.9 kbps.

TABLE 6

Primers for pTNF3 construction

| Primers | Sequence (5' -> 3') | PCR product |
|---|---|---|
| TNF_F3_primer | GAAGGATGCTTTATGGTGCGCTCCTCCCG (SEQ ID NO: 141) | insert |
| TNF_R1_primer | ACGAGCAGAAGGTCACAGGGCGATGATGCCCAAG (SEQ ID NO: 142) | insert |
| pCDshuttle_F1_primer | TGACCTTCTGCTCGTAGCG (SEQ ID NO: 143) | vector |
| pCDshuttle_R1_primer | CATAAAGCATCCTTCTTGGGTCAG (SEQ ID NO: 144) | vector |

Cloning 100 ng of the vector and 50 ng of the insert above were ligated by recombination of terminal sequences using In-Fusion Advantage PCR Cloning Kit (TAKARA BIO, Inc.). At this time, Cloning Enhancer (TAKARA BIO, Inc.) was also added into the reacting solution, concurrently degrading the template plasmid contained in the vector and the insert. Details were in accordance with the product instruction of In-Fusion Advantage PCR Cloning Kit.

2 µL of the In-Fusion reaction solution above was used for transforming *E. coli* TOP10 chemically Competent Cell (Invitrogen). Transforming conditions were in accordance with the product instruction. Transformed *E. coli* colonies were cultured overnight at 37° C. in LB (containing 75 µg/mL spectinomycin) liquid medium, and the plasmid was extracted from this culture (QIAprep Spin Miniprep Kit, QIAGEN). This plasmid was full-sequenced and named pTNF3 (SEQ ID No: 51).

Transformation of *Bifidobacterium*

The plasmid pTNF3 was used for transforming *B. longum* 105A using a similar method as Production Example 1.

Production Example 5

Production of a Secretory TNF Alpha-Expressing *Bifidobacterium* (pSec2-TNF Alpha)

Figure 7:
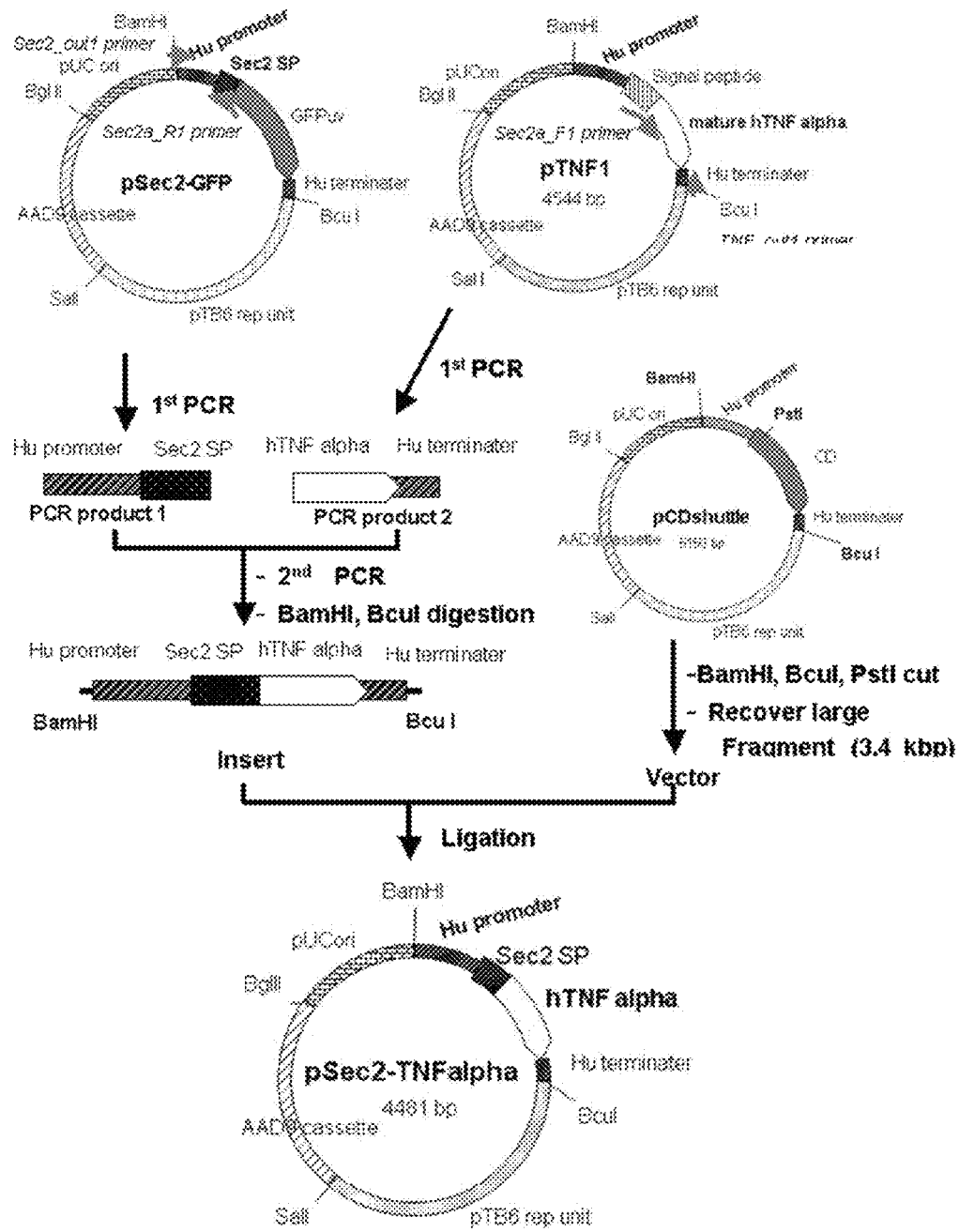
FIG. 7 is a map showing a summary of the construction of a secretory TNF alpha-expressing plasmid (pSec2-TNF alpha).

Summary of the construction of pSec2-TNF alpha, a plasmid in which the GFP portion of the plasmid pSec2-GFP was replace by TNF alpha, is shown in FIG. 7.

Vector Preparation

Plasmid pCDshuttle was fully digested with BamHI, BcuI and PstI (all from Fermentas). Reacting conditions were in accordance with the instruction of the enzymes. Digested plasmid was fractioned by electrophoresis on 1% agarose gel for purification (1×TBE buffer, with ethidium bromide), and a large fragment of approximately 3.4 kbps was cut out, and DNA was extracted from the agarose gel by DNA extraction kit (QIAquick Gel Extraction Kit, QIAGEN). Purified DNA fragment (vector) was electrophoresed on 0.8% agarose gel (1×TBE buffer, with ethidium bromide) with DNA concentration marker to estimate its concentration.

Insert Preparation

Plasmid pSec2-GFP was used as template for PCR amplification of Sec2 signal peptide coding sequence including HU promoter with Sec2_out1 primer and Sec2a_R1 primer (Table 5) (PCR product 1). Besides, plasmid pTNF1 was used for PCR amplification of TNF alpha coding sequence including HU terminator with Sec2a_F1 primer and TNF_out1 primer (Table 5) (PCR product 2). PCR products 1 and 2 were purified with PCR product purification kit (QIAquick PCR purification kit, QIAGEN), and the amount of PCR products was estimated by absorption measurement. PCR product 1 and PCR product 2 were mixed in equimolar amount. This PCR product mixture solutioning plus 2×PCR Solution PrimeSTAR HS (TAKARA BIO, Inc.) was made to 49 µL with 0.1×TE buffer. This solution was set in a thermal cycler, and two PCR fragments were linked by the reaction of 5 cycles, each cycle consisting of 98° C. for 10 seconds and 72° C. for 36 seconds. Then, the linked PCR product was amplified by adding Sec2_out1 primer and TNF_out1 primer, reacting 25 cycles, each cycle consisting of 98° C. for 10 seconds, 55° C. for 5 seconds and 72° C. for 70 seconds, before elongation at 72° C. for 30 seconds.

This was fractioned by electrophoresis on 1% agarose gel for purification (1×TBE buffer, with ethidium bromide), and a fragment of approximately 1.2 kbp was cut out, and DNA was extracted and purified from the agarose gel using DNA extraction kit (QIAquick Gel Extraction Kit, QIAGEN). This purified DNA fragment was fully digested with BamHI and BcuI. Reacting conditions were in accordance with the instruction of the enzymes. Digested plasmid was fractioned by electrophoresis on 1% agarose gel for purification (1×TBE buffer, with ethidium bromide), and a DNA fragment of approximately 1.2 kbp was cut out, and DNA was extracted and purified from agarose gel using DNA extraction kit (QIAquick Gel Extraction Kit, QIAGEN). Purified DNA fragment (insert) was electrophoresed on 0.8% agarose gel (1×TBE buffer, with ethidium bromide) with DNA concentration marker to estimate its concentration.

Ligation

The vector and the insert above were mixed in 1:3 molar ratio for ligation (Rapid DNA Ligation Kit, Fermentas). Details were in accordance with the product instruction.

Transformation of *E. coli*

2 µL of the ligation reaction solution above was used for transforming *E. coli* TOP10 chemically Competent Cell (Life Technologies Japan). Transforming conditions were in accordance with the product instruction.

Transformed *E. coli* colonies were cultured overnight in LB (containing 75 µg/mL spectinomycin) liquid medium at 37° C., and plasmids were extracted from this culture (QIAprep Spin Miniprep Kit, QIAGEN). The insert part of this plasmid was fully sequenced to confirm that there was no PCR error, and the plasmid was named as pSec2-TNF alpha.

Transformation of *Bifidobacterium* with pSec2-TNF Alpha

Plasmid pSec2-TNF alpha was used for transforming *B. longum* 105A in a similar way as Production Example 1.

Working Example 2

TNF Alpha Protein Expression by Recombinant *Bifidobacterium*

The recombinant bifidobacteria obtained from Production Example 4 and Production Example 5 (*Bifidobacterium longum* 105A/pSPxA-TNF alpha (x=7, 12), *Bifidobacterium longum* 105A/pSPxB-TNF alpha (x=1-4, 7, 9, 10, 12, 16 or 23) and *Bifidobacterium longum* 105A/pSec2-TNF alpha) in glycerin stock solution were inoculated at 1% in APS-2S-2.5SE (75 µg/mL spectinomycin) liquid medium and cultured in anaerobic condition at 37° C. for 24 hours (activation culture solution).

Subsequently, the activating culture solution was inoculated at 0.5% in a medium (for each 20 mL of APS-2S-2.5SE (75 µg/mL spectinomycin) liquid medium, 4 mL of 1M sodium phosphate buffer (pH6.8) was added). This was cultured in anaerobic condition at 37° C. for 18 hours.

After centrifuging the culture solution, culture supernatant was collected. Proteins in this culture supernatant was precipitated by trichloroacetic acid (TCA), washed with acetone, dissolved in a buffer for electrophoresis, and proteins in the culture supernatant were concentrated.

Besides, intracellular proteins were extracted as follows. 1 mL of the culture solution was mixed with 4 mL of PBS, centrifuged at 12,000 rpm for 5 minutes at 4° C., and the supernatant was removed. The precipitation was suspended in 5 mL PBS and centrifuged to remove the supernatant, which was repeated twice. After washing, the cells were made to the total volume of 1 mL with PBS, homogenized with a sonicator. After centrifugation, the supernatant was collected to provide an intracellular extract, which was then subjected to westernblot analysis.

A similar operation was performed for wild type *Bifidobacterium longum* 105A for a negative control. For a positive control for TNF alpha, human recombinant TNF alpha (PEPRO TECH, INC.) was used.

The culture supernatant (corresponding to 7.5 µL culture solution), culture supernatant concentrate (corresponding to 1 mL culture solution) and intracellular protein extract (corresponding to 7.5 µL culture solution) above were electrophoresed on 16% Tris-Glycine gel (Invitrogen). Note that, for following samples, the amount applied was adjusted as follows. The supernatant of SP3B-TNF alpha corresponding to 0.15 µL culture solution, the intracellular protein extract of SP16B-TNF alpha corresponding to 0.15 µL, the intracellular protein extract of SP23B-TNF alpha corresponding to 0.75 µL, the culture supernatant concentrate of the same corresponding to 20 µL and 100 µL were subjected for electrophoresis. These were transferred to PVDF membranes (Invitrogen, iBlot® Transfer Stacks) using iBlot® Transfer Device (Invitrogen). After blotting, the membranes were blocked, then reacted with anti-human TNF-alpha (goat) (R&D Systems) as primary antibody and anti-Goat IgG HRP Conjugate (Santa Cruz Biotechnology) as secondary antibody, and developed with ECL Advance Western blotting Detection Kit (GE Healthcare). These were analyzed by an imaging analyzer (Fluor S Max, Bio-Rad). The results of the analyses are shown in FIG. 8.

As a result, secretion was confirmed in 9 bacteria (*B. longum* 105A/pSP1B-TNF alpha, *B. longum* 105A/pSP3B-TNF alpha, *B. longum* 105A/pSP4B-TNF alpha, *B. longum* 105A/pSP7B-TNF alpha, *B. longum* 105A/pSP12B-TNF alpha, *B. longum* 105A/pSP16B-TNF alpha, *B. longum* 105A/pSP23B-TNF alpha, *B. longum* 105A/pSP7A-TNF alpha and *B. longum* 105A/pSec2-TNF alpha), with particularly prominent expression in the culture supernatant of 2 bacteria (*B. longum* 105A/SP3B-TNF alpha and *B. longum* 105A/SP23B-TNF alpha).

Reference Example 3

Confirmation of Secretion by a Non-TNFα-Secretory Bacterium *B. longum* 105A/pTNF 3

The glycerin stocks of *B. longum* 105A/pTNF3 obtained in Reference Example 2 and Wild-type *B. longum* 105A were inoculated at 1% to APS-2S-2.5SE (75 µg/mL spectinomycin) liquid medium, cultured in anaerobic condition at 37° C. for 24 hours (activating culture solution). The activating culture solution was inoculated at 0.5% to a medium (75 µg/mL spectinomycin) (for each 20 mL of APS-2S-2.5SE liquid medium added 4 mL of 1M sodium phosphate buffer (pH6.8)), which was cultured in anaerobic condition at 37° C. for 18 hours. Note that wild-type was cultured in a medium which was not supplemented with spectinomycin. This culture solution was centrifuged to collect a culture supernatant. Meanwhile, an intracellular extract was prepared as follows. 1 mL of the culture solution was washed with PBS buffer, then the cells were suspended in PBS buffer to make 1 mL and homogenized with a sonicator. This was centrifuged, and the supernatant was collected to give an intracellular extract.

Figure 9:
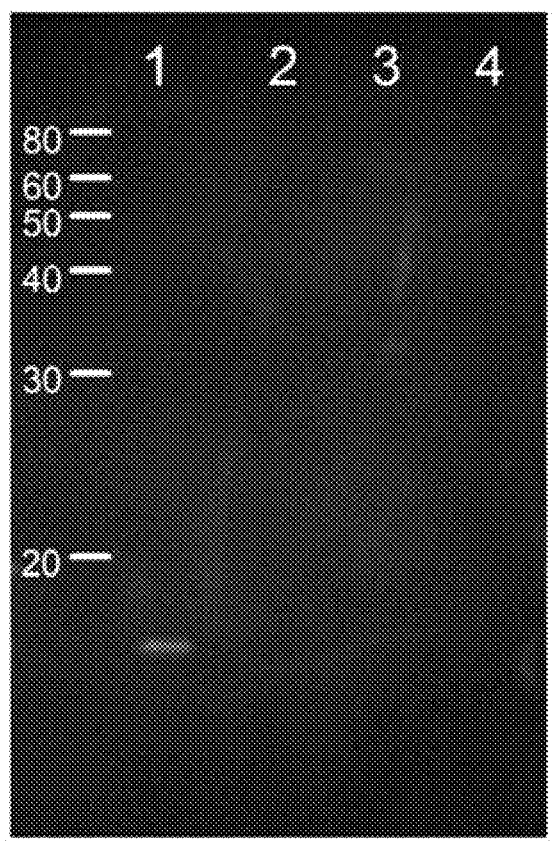
FIG. 9 is a picture showing the results of western blotting of *B. longum* 105A and *B. longum* 105A/pTNF3. The numbers on the vertical axis indicates the molecular weight (kDa).

A sample obtained from wild-type was used as a negative control. As a positive control, human-derived recombinant TNF alpha (PEPRO TECH, INC.) was used. The culture supernatant (corresponding to 7.5 µL of the culture solution) and intracellular extract (corresponding to 0.075 µL of the culture solution) above were electrophoresed on 15% polyacrylamide gel (ATTO Corporation). This was transferred to a PVDF membrane (Invitrogen, iBlotTransfer Stacks) using iBlot Transfer Device (Invitrogen). After blotting, the membrane was blocked and reacted using anti-human TNF-alpha (goat) (R&D Systems) as a primary antibody and anti-Goat IgG HRP Conjugate (Santa Cruz Biotechnology) as a secondary antibody, and developed by ECL Advance Western blotting Detection Kit (GE Healthcare). It was analyzed with an imaging analyzer (Fluor S Max, Bio-Rad). The results of the analyses are shown in FIG. 9.

As a result, when the intracellular extracts of *B. longum* 105A/pTNF3 and wild-type *B. longum* 105A were compared, a band indicating TNFα expression was confirmed in *B. longum* 105A/pTNF3 but not in wild-type *B. longum* 105A. Thus, it was shown that the cells transformed with the plasmid pTNF3 normally express TNFα. However, comparing both culture supernatants confirmed no TNFα in either culture supernatant, indicating that TNFα is not extracellulary secreted from *B. longum* 105A/pTNF3.

Production Example 6

Construction of pBifi-SP3B-TNF

Plasmid pBifi-SP3B-TNF was constructed from plasmid pSP3B-TNF alpha (*E. coli-Bifidobacterium* shuttle vector) by removing the origin of replication in *E. coli*. Details of the construction are shown in FIG. 10.
Preparation of pUCori-Removed Fragment 2.4 µg of plasmid extracted from the recombinant *E. coli*. TOP10/pSP3B-TNF alpha (shuttle vector) was digested by BamHI and BglII at 37° C. This was fractioned by electrophoresis using 0.8% agarose gel for purification, and a DNA fragment of approximately 3.8 kbps was cut out. DNA was extracted and purified from the cut-out gel (QIAquick Gel Extraction Kit, QIAGEN), and DNA concentration was measured by measuring the absorbance.
Self-Ligation of pUCori-Removed Fragment The pUCori-removed fragment above was self-ligated in 6 tubes. For each tube, 50 ng of pUCori-removed fragment was used for self-ligation in 50 µL reaction system at 25° C. for 5 minutes (RAPID DNA LIGATION KIT, Fermentas), then Ligase was deactivated by heating at 65° C. for 5 minutes. 6 ligation reaction solutions were assembled to one tube, and subjected to protein degradation by Proteinase K and subsequent protein removal by phenol/chloroform extraction and ethanol precipitation thereafter. DNA was dissolved in 10 µL 0.1×TE.
Transformation of *Bifidobacterium*

*Bifidobacterium longum* 105A competent cell was transformed (electroporation, Gene Pulser II, Bio-Rad Laboratories, Inc.) using 150 ng (5 µL) of the purified product after the ligation above. Immediately after an electric shock, a mixture of 800 µL of IMR liquid medium and 50 µL of vitamin C additive solution was added to the cuvette, which was then collected in a sterilized 2 mL microtube. The lid of tube was loosen, and the tube was placed in a dessicator, which was then deaerated by a vacuum pump and filled with carbon dioxide This manipulation was repeated three times to replace the air in the dessicator with carbon dioxide, before placing the dessicator in an incubator set to 37° C. and incubating for 3 hours.

After the incubation, the bacterial suspension was mixed thoroughly and smeared to two IMR agar media (containing 75 µg/mL SPCM). These plates were placed in a sealed vessel with deoxygenating/carbon dioxide-generating agent (Anaero Pac®-Anaero, MITSUBISHI GAS CHEMICAL, INC.) and cultured for two days in an incubator set to 37° C.
Confirmation of the Transformant and Production of a Glycerin Stock of Recombinant *Bifidobacterium*

The colonies of candidate recombinant formed on the IMR agar media (containing 75 µg/mL SPCM) above were streaked on BL-bS agar media (BL agar media containing spectinomycin, excluding horse defibrinated blood), placed in a sealed vessel with deoxygenating/carbon dioxide-generating agent (Anaero Pac®-Anaero, MITSUBISHI GAS CHEMICAL, INC.) and cultured for one day at 37° C. The streak-cultured bifidobacteria was cultured in anaerobic condition in APS-2S-2.5SE (75 µg/mL spectinomycin) liquid medium at 37° C. for one day, and plasmid DNA was extracted from this (QIAprep Spin Miniprep Kit, QIAGEN). The extracted DNA was used as template for PCR amplification with Check primer F1 (on AAD9 cassette) and Check primer R2 (on HU promoter), and PCR product size was confirmed by agarose-gel electrophoresis. Primer sequences are shown in Table 6. Locations of PCR primers are shown in FIG. 9. PCR product size was approximately 0.5 kbps, confirming the exclusion of pUC ori fragment. This result confirmed that this recombinant *Bifidobacterium* possesses pBifi-SP3B-TNF alpha, a plasmid in which pUC ori has been removed from pSP3B-TNF alpha.

TABLE 7

Primers for confirmation of shuttle and non-shuttle vectors

| Primers | Sequence (5' -> 3') |
| --- | --- |
| Check primer F1 | TGACTTAGAGGAATTACTACCTG (SEQ ID NO: 133) |
| Check primer R2 | AAAGTGGCGGAAAGCGCCAC (SEQ ID NO: 134) |

The streak culture on BL-bS agar medium was inoculated in APS-2S-2.5SE (75 µg/mL spectinomycin) liquid medium and cultured at 37° C. for 24 hours. To this culture solution glycerin solution was added to make a final concentration of 20%, to give a glycerin stock.
Nucleotide Sequencing of Plasmid pBifi-SP3B-TNF The glycerin stock of *Bifidobacterium longum* 105A/pBifi-SP3B-TNF was cultured in anaerobic condition in APS-2S-2.5SE (75 µg/mL spectinomycin) liquid medium. Bacterial cells were collected from the culture solution by centrifugation, suspended in 30 mM GTA buffer, then treated with N-acetyl muramidase. It was further treated with Proteinase K (QIAGEN) before purification by plasmid DNA purification kit (QIAprep Spin Miniprep Kit, QIAGEN). This plasmid DNA was used for determination of full nucleotide sequence, confirming the exclusion of pUCori (SEQ ID No.: 5).

Working Example 3

Confirmation of TNF Alpha Protein Secretion from Recombinant *Bifidobacterium*

The glycerin stock of *Bifidobacterium longum* 105A/pBifi-SP3B-TNF alpha obtained in Production Example 6 was inoculated at 1% in APS-2S-2.5SE (75 μg/mL spectinomycin) liquid medium and cultured in anaerobic condition at 37° C. for 24 hours (activating culture solution). The activating culture solution was inoculated at 0.5% in a medium (for each 20 mL of APS-2S-2.5SE (75 μg/mL spectinomycin) liquid medium, 4 mL of 1M sodium phosphate buffer (pH6.8) was added), which was cultured in anaerobic condition at 37° C. for 18 hours. This culture solution was centrifuged and the culture supernatant was collected. Besides, the intracellular extract was prepared as follows. 1 mL of the culture solution was washed with PBS, suspended in PBS to make 1 mL, then homogenized by a sonicator. This was centrifuged and the supernatant was collected to give the intracellular extract. Similar manipulation was performed for a shuttle vector *Bifidobacterium longum* 105A/pSP3B-TNF alpha and wild type *Bifidobacterium longum* 105A (wild type). Note that the wild type was cultured in a medium excluding spectinomycin. A sample obtained from the wild type was used as a negative control. For a positive control, human-derived recombinant TNF alpha (PEPRO TECH, INC.) was used.

The culture supernatant (corresponding to 0.75 μL culture solution) and intracellular protein extract (corresponding to 1.5 μL culture solution) above were electrophoresed on 15% polyacrylamide gel (ATTO Corporation). This was transferred to a PVDF membrane (Invitrogen, iBlot® Transfer Stacks) using iBlot® Transfer Device (Invitrogen). After blotting, the membrane was blocked, then reacted with anti-human TNF-alpha (goat) (R&D Systems) as primary antibody and anti-Goat IgG HRP Conjugate (Santa Cruz Biotechnology) as secondary antibody, and developed with ECL Advance Western blotting Detection Kit (GE Healthcare). This was analyzed by an imaging analyzer (Fluor S Max, Bio-Rad). The result of the analysis is shown in FIG. 11.

Working Example 4

Transformation of *E. coli* with pBifi-SP3B-TNF Alpha and pSP3B-TNF

Plasmids obtained from Production Example 6 (pBifi-SP3B-TNF alpha and pSP3B-TNF alpha) were used for transforming *E. coli*. TOP10 strain.

Transformation was performed in accordance with the product instruction of *E. coli*. TOP10 competent cell (Life Technologies Japan), and 100 μL each was smeared onto a LB (containing 75 μg/mL spectinomycin) agar medium in duplicate, cultured overnight at 37° C. Colonies were formed only when the shuttle vector pSP3B-TNF alpha was introduced (266 cfu and 226 cfu), while *E. coli* in which pBifi-SP3B-TNF alpha was transferred formed no colony on the selection medium.

Reference Example 4

Construction of Plasmid pBEshuttle

Figure 13:
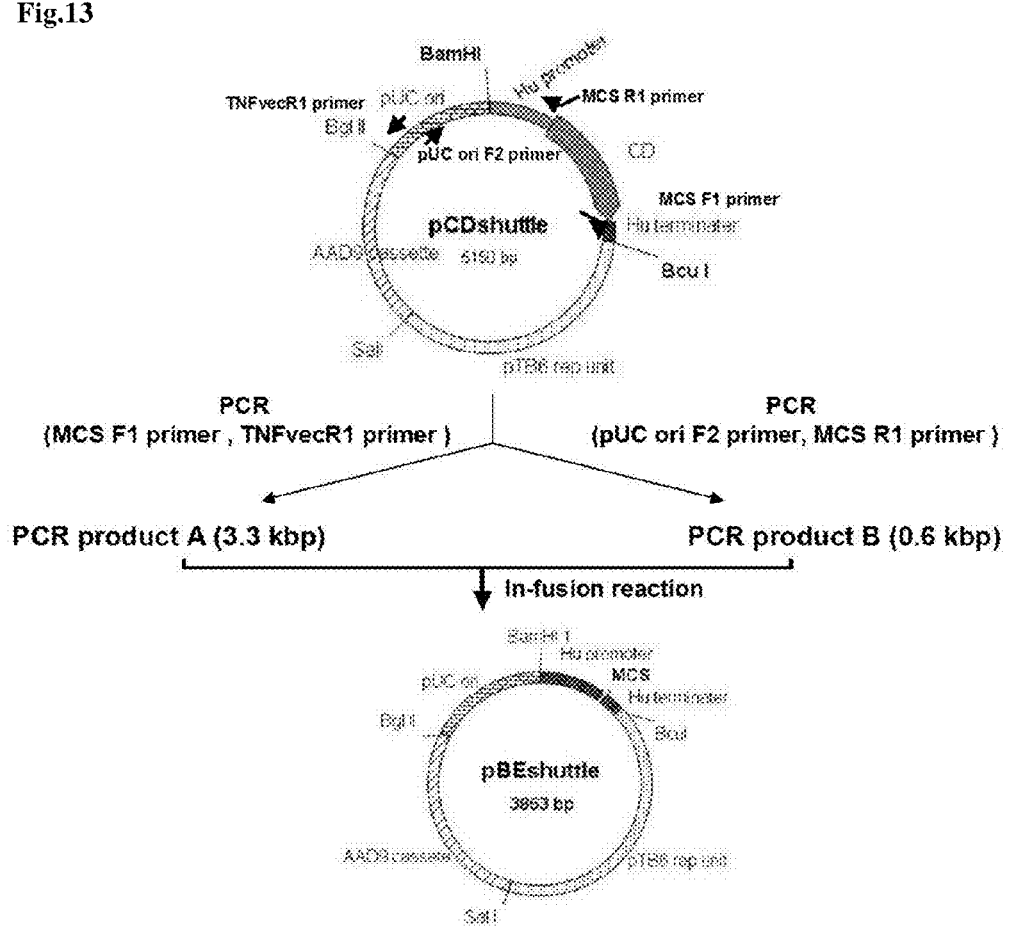
FIG. 13 is a map showing a summary of the construction of a mock plasmid (pBEshuttle) having a protein-expression cassette that does not comprise any insert.

We constructed pBEshuttle as a mock vector having a protein expression unit containing no insert, as follows. A summary is shown in FIG. 13.

PCR fragment Preparation 5 ng of the plasmid pCDshuttle was used as template for amplifying two PCR fragments A and B using PrimeSTAR® HS Premix (TAKARA BIO, Inc.). MCS F1 primer and TNFvec R1 primer were used for the amplification of PCR fragment A, and pUC ori F2 primer and MCS R1 primer was used for the amplification of PCR fragment B (Table 8).

The 15 nucleotides on 5' side of the primer for the amplification of PCR fragment A was designed to have a homologous sequence to the terminal of PCR fragment B, while the 15 nucleotides on 5' side of the primer for the amplification of PCR fragment B was designed to have a homologous sequence to the terminal of PCR fragment A.

The PCR program consisted of 30 cycles of 10 seconds at 98° C., 5 seconds at 55° C. and X seconds (PCR fragment A: X=3 minutes 20 seconds, PCR fragment B: X=35 seconds) at 72° C., followed by 30 seconds at 72° C.

A part of PCR product was electrophoresed on an agarose gel (1×TBE buffer, containing ethidium bromide; 0.8% agarose gel for PCR product A, 2% agarose gel for PCR product B) with DNA concentration marker, confirming a single band (PCR product A: approximately 3.3 kbps, PCR product B: approximately 0.6 kbps) and estimating its concentration.

TABLE 8

Primers for pBEshuttle Construction

| Primers | Sequence (5' -> 3') | PCR product |
|---|---|---|
| MCS_F1 primer | AAGCTTATCCTGCAGTGACC TTCTGCTCGTAGCGA (SEQ ID NO: 135) | A |
| TNFvec_R1_primer | GCCGTAGTTAGGCCACCACT TCAAG (SEQ ID NO: 117) | A |
| pUC_ori_F2_primer | TGGCCTAACTACGGCTACAC (SEQ ID NO: 118) | B |
| MCS_R1 printer | CTGCAGGATAAGCTTCATAA AGCATCCTTCTTG (SEQ ID NO: 136) | B |

Cloning 100 ng of the PCR product A and 35 ng of the PCR product B above were ligated by recombination of terminal sequences using In-Fusion Advantage PCR Cloning Kit (TAKARA BIO, Inc.). At this time, Cloning Enhancer (TAKARA BIO, Inc.) was also added into the reacting solution, concurrently degrading the template plasmid contained in the vector and the insert. Details were in accordance with the product instruction of In-Fusion Advantage PCR Cloning Kit.

2 μL of the In-Fusion reaction solution above was used for transforming *E. coli* TOP10 chemically Competent Cell (Invitrogen). Transforming conditions were in accordance with the product instruction. Transformed *E. coli* colonies were cultured overnight at 37° C. in LB (containing 75 μg/mL spectinomycin) liquid medium, and the plasmid was extracted from this culture (QIAprep Spin Miniprep Kit, QIAGEN). This plasmid was full-sequenced and named pBEshuttle (SEQ ID No: 50).

Transformation of *Bifidobacterium*

The plasmid pBEshuttle was used for transforming *B. longum* 105A using a method as used in Production Example 1.

Production Example 7

Production of Recombinant *Bifidobacterium B. breve*/pSP3B-TNF Alpha

*Bifidobacterium breve* JCM1192 was transformed with the plasmid pSP3B-TNF alpha in a method as used in the transformation of *Bifidobacterium* in Production Example 1.

Working Example 5

Confirmation of TNFα Protein Expression by Recombinant *Bifidobacterium*

The glycerin stocks of *B. longum* 105A/pBEshuttle obtained in Reference Example 4, *B. longum* 105A/pSP3B-

TNF alpha obtained in Production Example 4, *B. longum* 105A/pBifiSP3B-TNF alpha obtained in Production Example 6 and *B. breve*/pSP3B-TNF alpha obtained in Production Example 7 were inoculated at 1% to APS-2S-2.5SE (75 μg/mL spectinomycin) liquid media, cultured at 37° C. for 24 hours in anaerobic condition (activating culture). The activating culture solution was inoculated at 0.5% to a medium (75 μg/mL spectinomycin) (for each 20 mL of APS-2S-2.5SE liquid medium added 4 mL of 1M sodium phosphate buffer (pH6.8)), which was cultured at 37° C. for 18 hours in anaerobic condition. This culture solution was centrifuged to collect a culture supernatant. TNFα content in the culture supernatant was measured by ELISA of the culture supernatant (Quantikine Human TNF alpha/TNFSF1A Immunoassay, R&D Systems, Inc.). The measurement results are shown in Table 9.

TABLE 9

| sample name | culture time (hrs) | OD(600 nm) | TNFalpha conc. (μg/mL) |
|---|---|---|---|
| *B. longum* 105A/pBEshuttle | 18 | 2.539 | 0 |
| *B. longum* 105A/pSP3B-TNF alpha | 18 | 1.806 | 0.69 |
| *B. longum* 105A/pBifiSP3B-TNF alpha | 18 | 1.509 | 0.42 |
| *B. breve*/pSP3B-TNF alpha | 12 | 6.864 | 1.94 |

TNFα secretion was observed in the culture supernatant in either of *B. longum* 105A/pSP3B-TNF alpha, *B. longum* 105A/pBifiSP3B-TNF alpha and *B. breve*/pSP3B-TNF alpha, but not in *B. longum* 105A/pBEshuttle.

Working Example 6

The Physiological Activity of TNFα Protein Secreted by Recombinant *Bifidobacteirum* and the Neutralization of the Physiological Activity with Anti-hTNFα Antibody Culture of Test Bacterium and Preparation of Culture Supernatant The glycerin stocks of *B. longum* 105A/pBEshuttle obtained in Reference Example 4, *B. longum* 105A/pSP3B-TNF alpha obtained in Production Example 4 and *B. longum* 105A/pBifiSP3B-TNF alpha obtained in Production Example 6 were inoculated at 1% to APS-2S-2.5SE (75 μg/mL spectinomycin) liquid media, cultured at 37° C. for 24 hours in anaerobic condition (activating culture). The activating culture solution was inoculated at 0.5% to a medium (75 μg/mL spectinomycin) (for each 20 mL of APS-2S-2.5SE liquid medium added 4 mL of 1M sodium phosphate buffer (pH6.8)), which was cultured at 37° C. for 18 hours in anaerobic condition. This culture solution was centrifuged to collect a culture supernatant.

TNFα Cytotoxicity Assay

The physiological activity and neutralization of rhTNFα was assessed by examining the cytotoxicity via TNFα receptor, which is a physiological activity of TNFα. As a test cell, a human breast cancer cell line KPL-1 cell was used. KPL-1 cell was cultured in a DMEM medium (a DMEM medium supplemented with 10% (v/v) FBS and 0.1% (v/v) penicillin (50000 U/mL)/streptomycin (50 mg/mL) solution) at 37° C., in 5% $CO_2$ condition. This cell was seeded onto 96 well plate at $1 \times 10^4$ cells per well, cultured at 37° C. in 5% $CO_2$ for 24 hours to give confluent cells. The old medium was removed from these cells by aspiration, and freshly added thereto were 80 μL each per well of 10% (v/v) FBS supplemented with actinomycin D to make an actinomycin D final concentration of 5 μg/mL and DMEM medium supplemented with 0.1% penicillin (50000 U/mL)/streptomycin (50 mg/mL) solution.

Subsequently added were, as samples for measurement, a medium for *Bifidobacterium* (APS-2S-2.5SE), rhTNF alpha prepared at 100 ng/mL as rhTNFα standard, five times dilution of *B. longum* 105A/pBEshuttle culture supernatant, five times dilution of *B. longum* 105A/pSP3B-TNF alpha culture supernatant and five times dilution of *B. longum* 105A/pBifiSP3B-TNF alpha culture supernatant, 10 μL each per well. Added thereto in order to measure the neutralizing ability against rhTNFα physiological activity were anti-hTNFα antibody (anti-human TNF alpha, R&D Systems, 0.0125-0.1 mg/mL), normal goat IgG (normal Goat IgG, R&D Sytems, 0.0125-0.1 mg/mL), and 10% (v/v) FBS and DMEM medium supplemented with 0.1% (v/v) penicillin (50000 U/mL)/streptomycin (50 mg/mL) solution, 10 μL each per well. This plate was cultured at 37° C. in 5% $CO_2$ for 48 hours.

Figure 14:
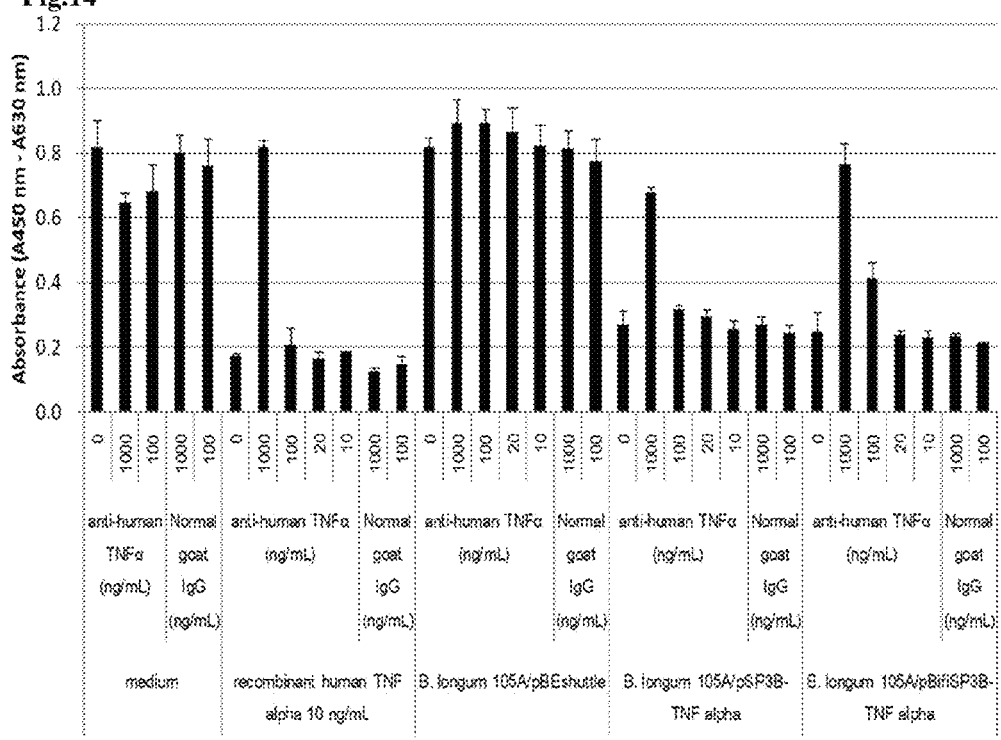
FIG. 14 is a graph showing the results of cytotoxicity assay for TNFα.

Measuring cytotoxicity employed Cell Counting Kit-8 (DOJINDO), wherein 10 μL per well of this solution was added to each well, before further culturing for 4 hours at 37° C. in 5% $CO_2$ and measuring of the absorbance at wavelength of 450 nm and 630 nm (630 nm was used as reference wavelength). The results of the analyses are shown in FIG. 14, in which the culture supernatant of the recombinant bacteria *B. longum* 105A/pSP3B-TNF alpha and *B. longum* 105A/pBifiSP3B-TNF alpha showed cytotoxicity against KPL-1 cells while being neutralized by anti-TNFα antibody, confirming that the recombinant hTNFα secreted in the culture supernatant had a physiological activity.

Working Example 7

Measurement of Antitumor Effect of *B. longum* 105A/pSP3B-TNF Alpha and *B. breve*/pSP3B-TNF Alpha The antitumor effect of *B. longum* 105A/pSP3B-TNF alpha prepared in Production Example 4 and *B. breve*/pSP3B-TNF alpha prepared in Production Example 7 were measured.

(1) Culturing of Transplant Tumor Cells

Human breast cancer cell line KPL-1 cells were cultured in a DMEM medium supplemented with 10% (v/v) FBS and 0.1% (v/v) penicillin (50000 U/mL)/streptomycin (50 mg/mL) solution at 37° C. in 5% $CO_2$ condition.

Upon reaching confluent, the cells were detached by washing with 1×PBS(−) and adding trypsin-EDTA, and the cells were collected by centrifugation (1000 spins/5 minutes) and appropriately diluted with DMEM medium and subcultured.

Cells after 5 passages were used for transplantation experiments. The number of viable cells which were not stained with trypan blue was counted on Thoma hemocytometer (Thoma deep 0.1 mm ERMA, Tokyo), suspended in Hank's solution and the cell number was adjusted to at $2.5 \times 10^6$ cells/mL.

(2) Production of a Cancer-Bearing Nude Mouse and Measurement of Tumor Volume 0.2 mL of the prepared KPL-1 cell suspension was subcutaneously transplanted to a nude mouse on the dosal side of the right anterior limb ($5 \times 10^5$ cells/mouse).

Tumor volume after transplantation was assessed by measuring tumor diameter (long axis, short axis and thickness) using calipers and calculated by following equation:

Tumor volume($mm^3$)=long axis(mm)×short axis (mm)×thickness(mm)/2

(3) Grouping and Group Constitution

From KPL-1 cancer-bearing nude mice, 24 mice whose tumor volumes were around approximately 80 to 135 $mm^3$ were selected and divided into 3 groups (8 animals for each group) such that the average tumor volume would be similar. This day was set to Day 0.

The constitution of the test groups is as shown in Table 10. That is, Group I: a group with no treatment, Group II: a group receiving *B. longum* 105A/pSP3B-TNF alpha, Group III: a group receiving *B. breve*/pSP3B-TNF alpha.

TABLE 10

Group constitution

| Group | Given substance | Dosage | Number of dosage (times/day) | Administration date (Day) | |
|---|---|---|---|---|---|
| Group I | — | — | — | — | 8 |
| | — | — | — | — | |
| Group II | *B. longum* 105A/ pSP3B-TNF alpha | 0.2 mL/body/time | 2 | 1, 4, 8, 11, | 8 |
| | Maltose | 200 mg/body/day | 2 | 1~21 | |
| Group III | *B. breve*/ pSP3B-TNF alpha | 0.2 mL/body/time | 2 | 1, 4, 8, 11 | 8 |
| | Maltose | 200 mg/body/day | 2 | 1~21 | |

(4) Culturing of Bacteria and Preparation of Bacterial Suspension for Administration Culturing of Bacteria The glycerin stocks of the bifidobacteria *B. longum* 105A/pSP3B-TNF alpha prepared in Production Example 4 and *B. breve*/pSP3B-TNF alpha prepared in Production Example 7 were inoculated at 1% to APS-2S-2.5SE (75 μg/mL specinomycin) liquid media, cultured at 37° C. for 23.5 hours in anaerobic condition (activating culture solution). Next, the activating culture solution was inoculated at 1% to 20 mL of APS-2S-2.5SE (75 μg/mL spectinomycin) liquid medium, cultured at 37° C. for 18 hours in anaerobic condition (main culture solution).

Preparation of Cultured Viable Cells for Administration (*B. longum* 105A/pSP3B-TNF Alpha)

10 mL of the main culture solution obtained as above was measured by a measuring pipette and added to a conical tube containing 40 mL of well-cooled PBS buffer, gently mixed by inversion, and then centrifuged in a centrifuge cooled at 4° C., at 8000 rpm for 10 minutes. After centrifugation, the supernatant was removed and 40 mL of fresh PBS buffer was added and gently mixed by a vortex. This manipulation was repeated four times to wash the cells. The washed cells were suspended in 5 mL PBS buffer to give a cultured viable cells for administration.

Preparation of Cultured Viable Cells for Administration (*B. breve*/pSP3B-TNF Alpha)

10 mL of the main culture solution obtained as above was measured by a measuring pipette and added to a conical tube containing 40 mL of well-cooled PBS buffer, gently mixed by inversion, and then centrifuged in a centrifuge cooled at 4° C., at 8000 rpm for 10 minutes. After centrifugation, the supernatant was removed and 40 mL of fresh PBS buffer was added and gently mixed by a vortex. This manipulation was repeated four times to wash the cells. The washed cells were suspended in 10 mL PBS buffer to give cultured viable cells for administration.

(5) Administration of the Bacterium and Maltose

Administering the Bacterium

For Group II and Group III, 0.2 mL per mouse of each cultured viable cells (Group II: *B. longum* 105A/pSP3B-TNF alpha, Group III: *B. breve*/pSP3B-TNF alpha) was administered intravenously twice a day (AM/PM), at a pace of twice a week (Day 1, 4, 8, 11), for two weeks. The cultured viable cells were administered in the administered total volume of 1.6 mL, i.e., the total cell number of $3.1 \times 10^9$ cfu/mouse for *B. longum* 105A/pSP3B-TNF alpha, and $4.8 \times 10^9$ cfu/mouse for *B. breve*/pSP3B-TNF alpha. The number of administered viable cells was measured as follows.

Measuring Viable Cell Number

The cultured viable cells were diluted $10^6$ times with an anaerobic dilutant, 100 μL of which was smeared to three BLFS plates each and cultured in anaerobic condition in a sealed vessel (Anaero Pac Rectangular jar, MITSUBISHI GAS CHEMICAL, INC.) with a deoxygenating/carbon dioxide-generating agent in an incubator at 37° C. for three days. For each plate in which colonies of 30 to 300 were detected, the number of the cells administered was calculated by the formula below.

Number of the cells administered (cfu)=number of colonies (*a*)×dilution ratio at the time of being smeared to the plate (*b*)×conversion coefficient for 1 mL of cultured viable cells (*c*)×dosage (mL)

(a): (P1+P2+P3)/3 [average number of colonies of 3 plates (P1, P2, P3)]
(b): ×$10^6$ [$10^6$ times dilution]
(c): ×10 [smeared 1000, per plate]

Administering Maltose

For Group II and III, 1 mL of 10% maltose solution was administered intraperitoneally as carbohydrate source twice a day (200 mg/body/day). Administration period was for 21 days from the day of administering the cultured viable cells (Day 1-21).

(6) Confirming Tumor-Growth Suppressing Effect

For all mice, tumor diameter was measured before the initiation of the treatment (at grouping) and for 22 days after the initiation of the treatment, at frequency of once in 3 to 4 days, to confirm the effect against tumor growth.

The average tumor volume ±SD for each group of mice was calculated, and antitumor effect was assessed using relative tumor volume ratio to the control group (Group I) [T/C (%)] as an index. Also, statistical analyses (comparison between two groups: t-test) between Group I and Group II and between Group I and Group III were performed.

The tumor volume for each group (average ±SD) is shown in Table 11 below.

Figure 15:
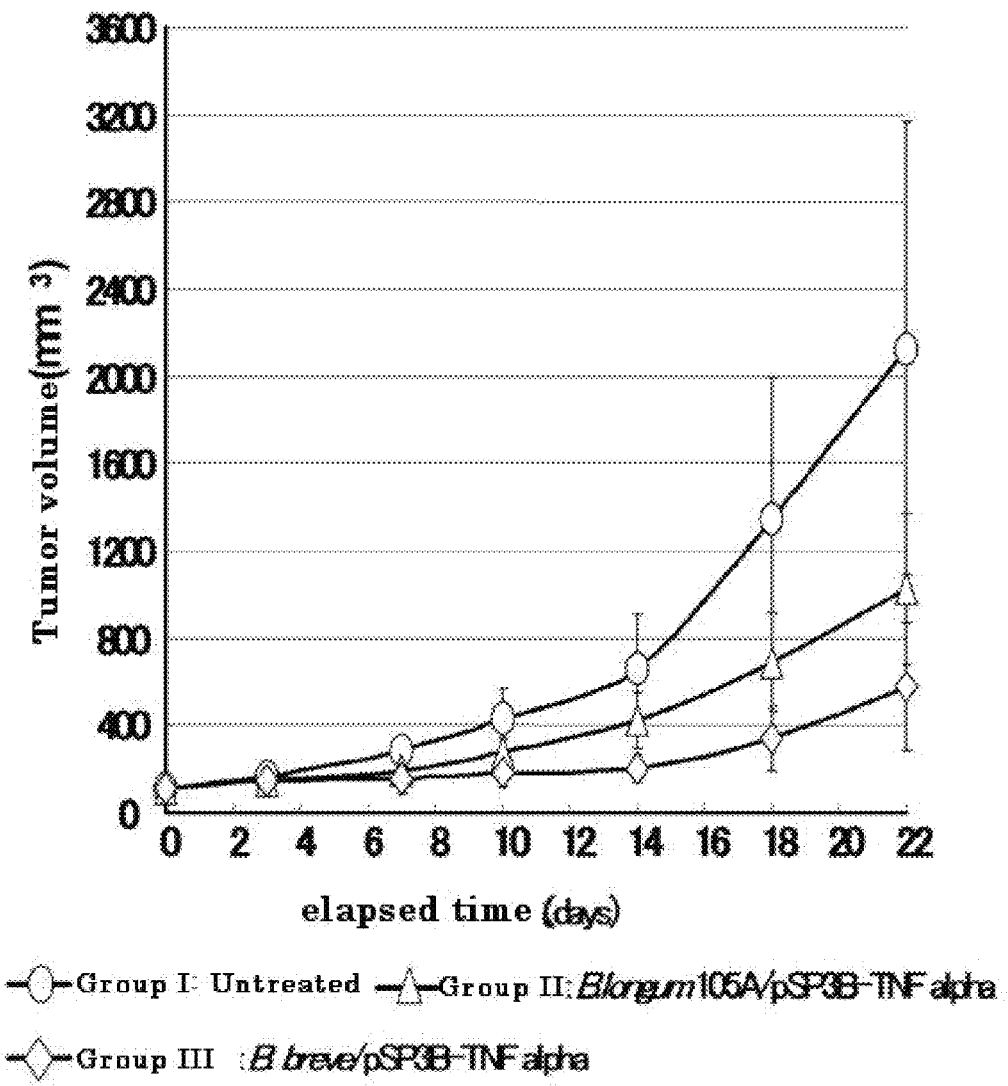
FIG. 15 is a graph showing the results of chronological changes in tumor volume in an in vivo antitumor effect measurement assay in mouse for secretory TNFα-expressing plasmids *B. longum* 105A/pSP3B-TNF alpha and *B. breve*/pSP3B-TNF alpha.

Chronological variation of tumor volume at the time was also shown in FIG. 15.

TABLE 11

Average Tumor volume of each group

| Group Given Cell | Number of animals | Measurement date (Day) | Tumor volume (mm3) after grouping (Day0) | | | | | | | T/C (%)[#1] at Day22 | Two tailed t-test (p-value) Group I$_{VS}$ |
|---|---|---|---|---|---|---|---|---|---|---|---|
| | | | 0 | 3 | 7 | 10 | 14 | 18 | 22 | | |
| —) No treatment | 8 | Average | 107.2 | 168.6 | 284.4 | 426.5 | 658.3 | 1347.7 | 2128.8 | — | — |
| | | S.D. | 19.6 | 33.0 | 52.1 | 139.0 | 248.3 | 647.2 | 1040.1 | | |

TABLE 11-continued

Average Tumor volume of each group

| Group Given Cell | Number of animals | Measurement date (Day) | Tumor volume (mm3) after grouping (Day0) | | | | | | | T/C (%)[#1] at Day22 | Two tailed t-test (p-value) Group $I_{VS}$ |
|---|---|---|---|---|---|---|---|---|---|---|---|
| | | | 0 | 3 | 7 | 10 | 14 | 18 | 22 | | |
| ニ) B. lonum 105A/ pSP3B-TNF alpha | 8 | Average S.D. | 105.9 18.1 | 146.7 23.6 | 196.6 33.8 | 274.4 64.7 | 420.0 127.5 | 690.2 225.9 | 1028.8 348.6 | 48.3 | 0.021 |
| 三) B. breve/ pSP3B-TNF alpha | 8 | Average S.D. | 105.5 18.6 | 142.4 48.8 | 151.7 56.7 | 181.9 64.5 | 201.6 61.5 | 337.3 146.6 | 579.4 292.2 | 27.2 | 0.004 |

[#1]T/C (%) = Average tumor volume of Group II or Group III/Average tumor volume of Group I x 100

In either group receiving B. longum 105A/pSP3B-TNF alpha or B. breve/pSP3B-TNF alpha, a significant decrease in tumor volume was observed compared with untreated group.

Working Example 8

Measurement of Antitumor Effect of B. longum 105A/pSP3B-TNF Alpha

We measured the antitumor effect of B. longum 105A/pSP3B-TNF alpha prepared in Production Example 4 in concomitant use with adriamycin.

(1) Culturing of the Transplant Tumor Cells

Human breast cancer cell line KPL-1 cell was cultured in DMEM medium supplemented with 10% (v/v) FBS and 0.1% (v/v) penicillin (50000 U/mL)/streptomycin (50 mg/mL) under the condition at 37° C. in 5% $CO_2$.

Upon reaching confluent, the cells were detached by washing with 1×PBS(−) and adding trypsin-EDTA, and the cells were collected by centrifugation (1000 spins/5 minutes) and appropriately diluted with DMEM medium and subcultured.

Cells after 5 passages were used for transplantation experiments. The number of viable cells which, were not stained with trypan blue was counted on Thoma hemocytometer (Thoma deep 0.1 mm ERMA, Tokyo), suspended in Hank's solution and the cell number was adjusted to at $2.5 \times 10^6$ cells/mL.

(2) Production of a Cancer-Bearing Nude Mouse and Measurement of the Tumor Volume 0.2 mL of the prepared KPL-1 cell suspension was subcutaneously transplanted to a nude mouse on the dorsal side of the right anterior limb ($5 \times 10^5$ cells/mouse). Tumor volume after transplantation was assessed by measuring tumor diameter (long axis, short axis and thickness) using calipers and calculated by following equation:

Tumor volume (mm³)=long axis (mm)×short axis (mm)×thickness (mm)/2

(3) Grouping and Group Constitution

From KPL-1 cancer-bearing nude mice, 18 mice whose tumor volumes were around approximately 80 to 120 mm³ were selected and divided into 3 groups (6 animals for each group) such that the average tumor volume would be similar. This day was set to be as Day 0.

The constitution of the test groups are as shown in Table 12. That is, Group I: untreated group, Group II: the group receiving adriamycin alone, Group III: the group receiving the combination of bacterium (B. longum 105A/pSP3B-TNF alpha)+adriamycin.

TABLE 12

Group constitution

| Group | Given substance | Dosage | Number of dosage (times/day) | Administration date (Day) | Number of animals |
|---|---|---|---|---|---|
| Group I | Bacterium Maltose Adriamycin | — — — | — — — | — — — | 6 |
| Group II | Bacterium Maltose Adriamycin | — — 5 mg/kg | — — 1 | — — 0 * | 6 |
| Group III | Bacterium | 0.2 mL/ body/time | 2 | 1, 5, 8, 12 | 6 |
| | Maltose | 200 mg/ body/day | 2 | 1 to 20 | |
| | Adriamycin | 5 mg/kg | 1 | 0 * | |

(4) Culturing of the Bacterium (B. longum 105A/pSP3B-TNF alpha)

The glycerin stock of the Bifidobacterium B. longum 105A/pSP3B-TNF alpha prepared in Production Example 4 was inoculated at 1% to APS-2S-2.5SE (75 μg/mL spectinomycin) liquid medium, cultured at 37° C. for 23.5 hours in anaerobic condition (activating culture solution). Next, the activating culture solution was inoculated at 1% to 20 mL of APS-2S-2.5SE (75 μg/mL spectinomycin) liquid medium, cultured at 37° C. for 18 hours in anaerobic condition (main culture solution).

Preparation of Cultured Viable Cells for Administration 5 mL of the main culture solution above was measured by a measuring pipette and added to a conical tube containing 20 mL of well-cooled PBS buffer, gently mixed by inversion, and then centrifuged in a centrifuge cooled at 4° C., at 8000 rpm for 10 minutes. After centrifugation, the supernatant was removed and 20 mL of fresh PBS buffer was added and gently mixed by a vortex. This manipulation was repeated four times to wash the cells. The washed cells were suspended in 2.5 mL PBS buffer to give a cultured viable cells for administration.

(5) Administration of the Bacterium, Maltose and Adriamycin

Administering the Bacterium

For Group III, 0.2 mL per mouse of cultured viable cells (test drug) was administered intravenously twice a day (AM/PM), twice a week (Day 1, 5, 8, 12). The cultured viable cells were administered in the total administered volume of 1.6 mL, i.e., the total cell number of $3.0 \times 10^9$ cfu/mouse. The number of administered viable cells was measured as follows.

Measuring Viable Cell Number

The cultured viable cells were diluted $10^6$ times with an anaerobic dilutant, 100 μL of which was smeared to three BLFS plates each and cultured in anaerobic condition in a sealed vessel (Anaero Pac Rectangular jar, MITSUBISHI GAS CHEMICAL, INC.) with a deoxygenating/carbon dioxide-generating agent in an incubator at 37° C. for three days. For each plate in which colonies of 30 to 300 were detected, the number of the cells administered was calculated by the formula below.

Number of the cells administered (cfu)=number of colonies (a)×dilution ratio at the time of being smeared to the plate (b)×conversion coefficient for 1 mL of cultured viable cells (c)×dosage (mL)

(a): (P1+P2+P3)/3 [average number of colonies of 3 plates (P1, P2, P3)]
(b): ×$10^6$ [$10^6$ times dilution]
(c): ×10 [smeared 100 μL per plate]

Administering Maltose

For Group III, 1 mL of 10% maltose solution was administered intraperitoneally as carbohydrate source twice a day (200 mg/body/day). Administration period was for 20 days from the day of administering the cultured viable cells (Day 1-20).

Administering Adriamycin

For Group II and Group III, 0.1 mL adriamycin solution (1.0 mg/mL) was administered intravenously to mice only on a day before the first administration of bacterium (Day 0).

(6) Confirming Tumor-Growth Suppressing Effect

For all mice, tumor diameter was measured before the initiation of the treatment (at grouping) and for 21 days after the initiation of the treatment, at frequency of once in 3 to 4 days, to confirm the effect against tumor growth.

The average tumor volume ±SD for each group of mice was calculated, and antitumor effect was assessed using relative tumor volume ratio to the control group (Group I) [T/C (%)] as an index. Also, in order to assess the antitumor ability of the present bacterium secreting TNFα, a statistical analysis (comparison between two groups: t-test) between Group II and Group III was performed.

The tumor volume for each group (average ±SD) is shown in Table 13 below.

Figure 16:
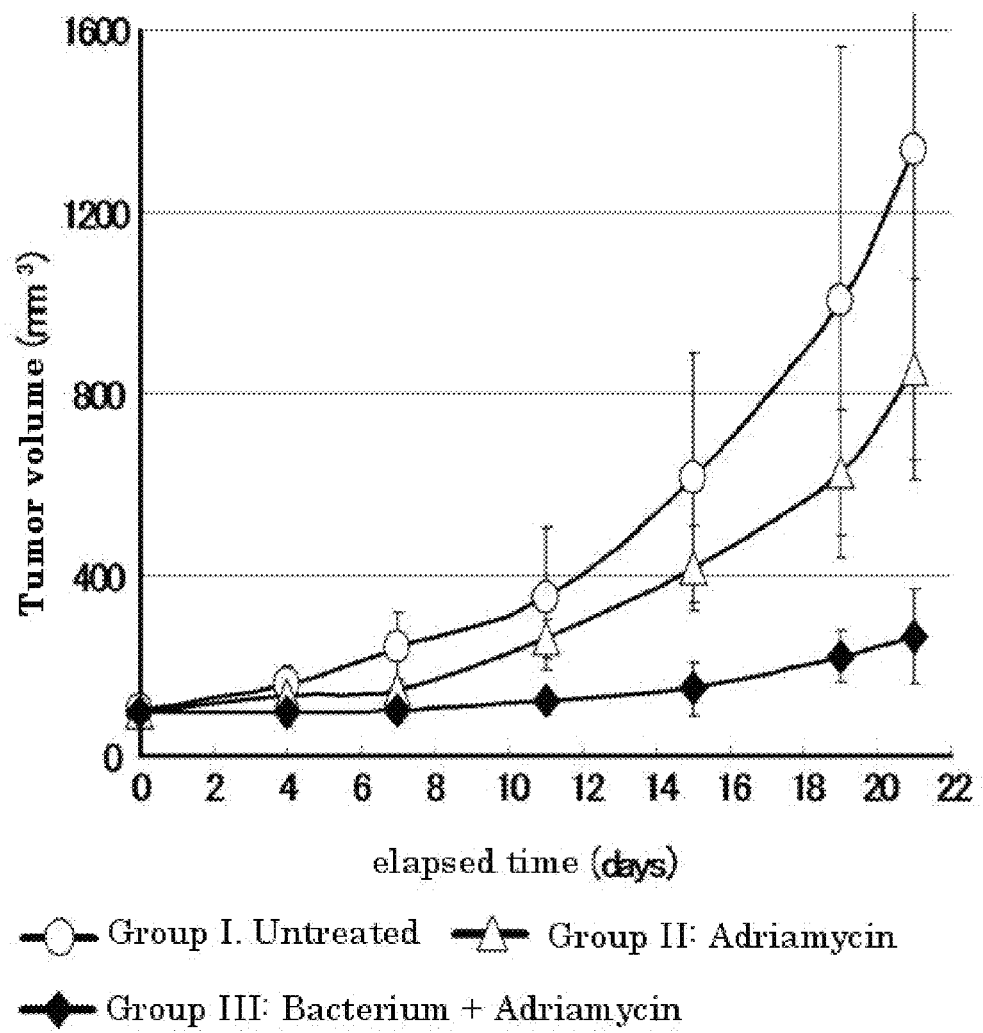
FIG. 16 is a graph showing the results of chronological changes in tumor volume in an in vivo antitumor effect measurement assay in mouse for secretory TNFα-expressing plasmids *B. longum* 105A/pSP3B-TNF alpha used in combination with adriamycin.

Chronological variation of tumor volume at the time was also shown in FIG. 16.

In the group received a concomitant use of *B. longum* 105A/pSP3B-TNF alpha and adriamycin, tumor volume was significantly reduced, not only when compared with untreated group but also when compared with the group receiving adriamycin alone. This means, namely, the concomitant use of adriamycin and *B. longum* 105A/pSP3B-TNF alpha may increase their effects.

Production Example 8

Production of a Non-Secretory Human IL-18-Expressing *Bifidobacterium*

Construction of Plasmid phIL18mut-His

Figure 17:
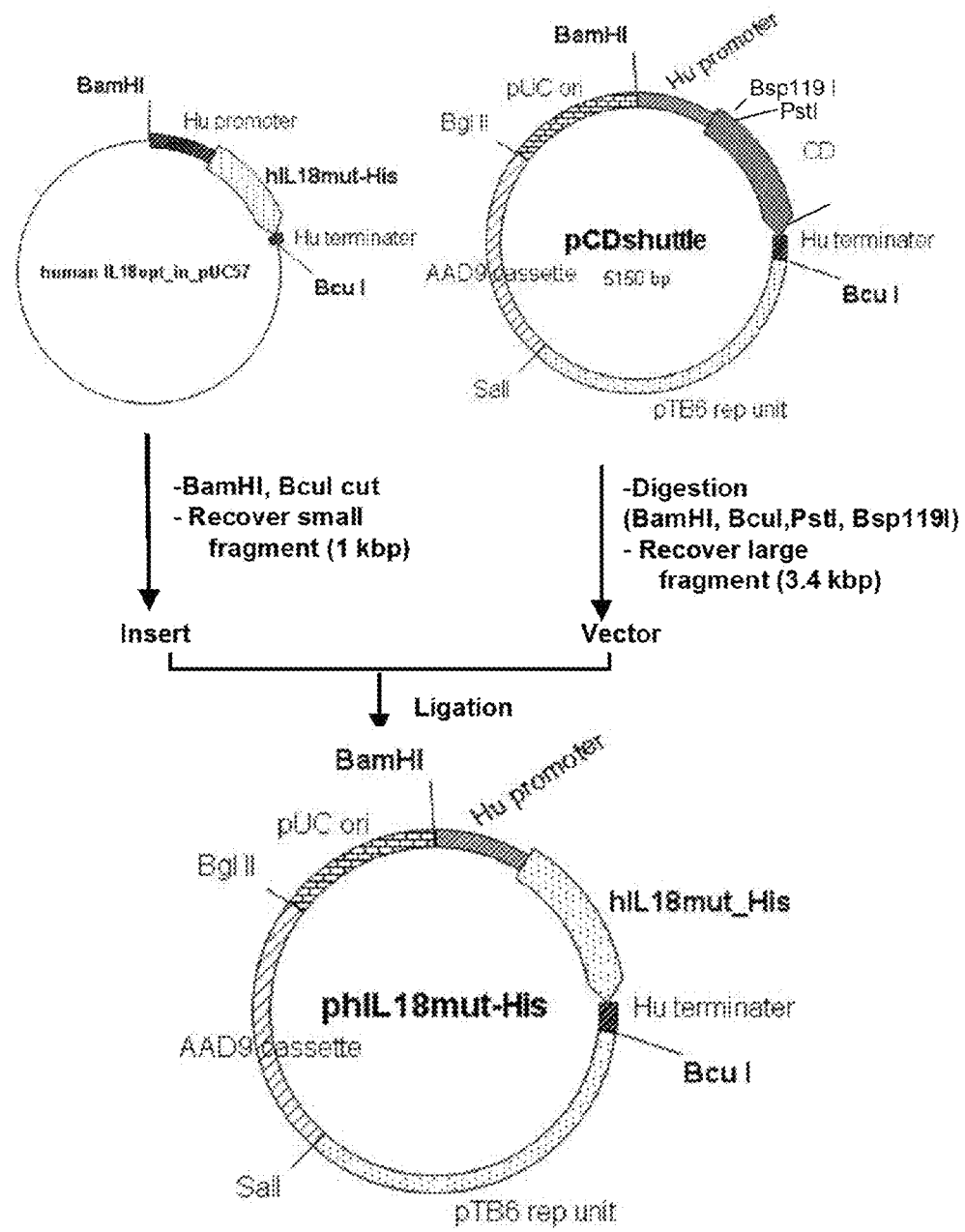
FIG. 17 is a map showing a summary of the construction of a non-secretory human IL-18-expressing plasmid phIL18mut-His.

We constructed a shuttle vector (*Bifidobacterium-E. coli*) having only the human IL-18 located downstream of Hu promoter derived from *Bifidobacterium* but having no secretory signal. A summary is shown in FIG. 17. Details are as follows.

Insert Preparation

We used a plasmid human IL18_opt_in_pUC57 having an artificial DNA of human IL-18 (Accession No: NM_001562, 329th to 799th nucleotide sequence in mature protein coding region) of which codons were optimized for *Bifidobacterium*, and Hu promoter located upstream thereof and Hu terminator located downstream thereof (custom-synthesized by GenScript). Upon synthesizing the artificial DNA, amino acid substitutions were introduced to the mature human IL-18 at 2 sites, i.e., at 7th amino acid (from E to A) and at 54th amino acid (from K to A), to decrease the neutralization with a IL-18-binding protein, and a histidine tag was added to the C-terminal (the amino acid sequence of the mature human IL-18: SEQ ID No: 47).

Added to 2 μg of the plasmid human IL18_opt_in_pUC57 25 unit of BamHI and 15 unit of BcuI (both enzymes from Fermentas), which was incubated at 37° C. for 3 hours to allow a complete digestion. After the digestion, the plasmid was electrophoresed on 1% agarose gel for purification (1×TBE buffer, containing ethidium bromide) to separate DNA fragments. A small fragment of approximately 1 kbp was cut out, and DNA was extracted and purified from the agarose gel by a DNA extraction kit (QIAquick Gel Extraction Kit, QIAGEN). Purified DNA fragment (insert) was elec-

TABLE 13

Average tumor volume of each group

| Group Given cell | Number of animals | Measurement date (Day) | Tumor volume (mm3) after grouping (Day0) | | | | | | | T/C (%)[#2] at Day21 | Two tailed t-test (p-value) —) vs ±) ±) vs ≠) |
|---|---|---|---|---|---|---|---|---|---|---|---|
| | | | 0 | 4 | 7 | 11 | 15 | 19 | 21 | | |
| —) No treatment | 8 | Average S.D. | 100.3 13.8 | 156.5 44.4 | 238.5 77.5 | 347.4 157.2 | 613.5 274.9 | 1002.2 561.6 | 1337.0 726.0 | — | — |
| ±) Receiving adriamycin[#1] | 8 | Average S.D. | 97.7 14.3 | 133.6 21.5 | 145.4 25.3 | 257.9 42.5 | 415.2 92.4 | 625.2 137.5 | 852.6 199.0 | 63.8 | 0.168 — |
| ≠) Receiving bacterium and adriamycin[#1] | 8 | Average S.D. | 97.8 12.6 | 96.9 30.0 | 100.7 29.1 | 120.4 26.8 | 148.5 57.8 | 220.4 57.7 | 265.0 104.6 | 19.8 | 0.015 0.0003 |

[#1]Adriamycin 5.0 mg/kg
[#2]T/C (%) = Average tumor volume of Group II or Group III/Average tumor volume of Group I × 100 trophoresed on 0.8% agarose gel (1×TBE buffer, containing ethidium bromide) with DNA concentration marker to estimate its concentration.

Vector Preparation

The plasmid pCDshuttle was completely digested with BamHI, BcuI, PstI and Bsp119I (all from Fermentas; PstI and Bsp119I has their recognition sites on CD). Reacting conditions were in accordance with the instruction for use of the enzymes. After the digestion, the plasmid was electrophoresed on 1% agarose gel for purification (1×TBE buffer, containing ethidium bromide) for separation, a large fragment of approximately 3.4 kbps was cut out, and DNA was extracted and purified from the agarose gel by a DNA extraction kit (QIAquick Gel Extraction Kit, QIAGEN). Purified DNA fragment (vector) was electrophoresed on 0.8% agarose gel (1×TBE buffer, containing ethidium bromide) with DNA concentration marker to estimate its concentration.

Cloning

The vector and the insert above were mixed in 1:3 (molar ratio) and ligated (Rapid DNA Ligation Kit, Fermentas). Details were in accordance with the product instruction.

2 µL of the ligation reaction solution above was used for transforming *E. coli* TOP10 chemically Competent Cell (Invitorogen). Transforming conditions were in accordance with the product instruction. Transformed *E. coli* colonies were cultured overnight in LB (containing 75 µg/mL spectinomycin) liquid medium at 37° C., from which the plasmid was extracted (QIAprep Spin Miniprep Kit, QIAGEN). The plasmid was named as phIL18mut-His (SEQ ID No: 48).

Construction of pSP3B-hIL18mut

Figure 18:
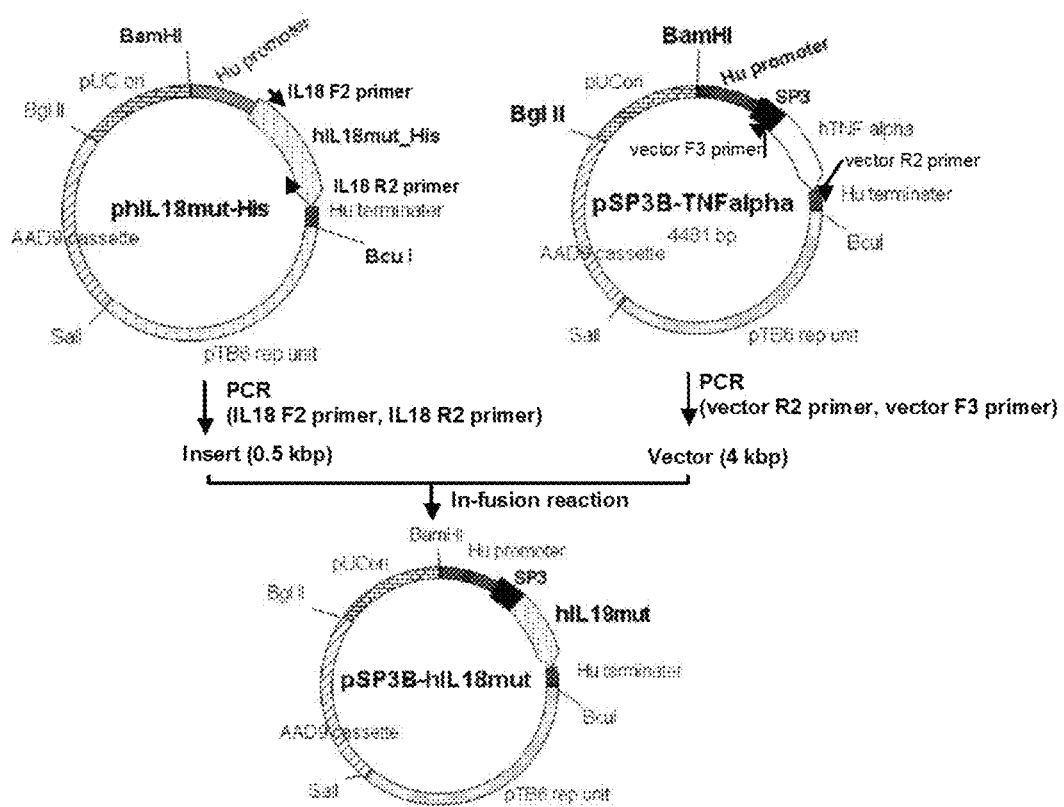
FIG. 18 is a map showing a summary of the construction of a secretory human IL-18-expressing plasmid pSP3B-hIL18mut.

We constructed a shuttle vector (*Bifidobacterium-E. coli*) having human IL18mut fused to a signal peptide downstream of Hu promoter derived from *Bifidobacterium*. A summary is shown in FIG. 18. Details are as follows.

Insert Preparation 5 ng of the plasmid phIL18mut-His was used as template for PCR amplification of hIL18mut coding region by PrimeSTAR® HS Premix (TAKARA BIO, Inc.). IL18 F2 and IL18 R2 primers were used, in which the 15 nucleotides on the 5' side of each primer had a homologous sequence to the vector terminal (Table 14). Primers were designed such that the PCR product would not contain the histidine tag from C-terminal of IL-18. PCR program consisted of 30 cycles of 10 seconds at 98° C., 5 seconds at 55° C., 30 seconds at 72° C., followed by 30 seconds at 72° C.

A part of the PCR product was electrophoresed on 2% agarose gel (1×TBE buffer, containing ethidium bromide) with DNA concentration marker, confirming a single band of approximately 0.5 kbp and estimating its concentration.

Vector Preparation 5 ng of the plasmid pSP3B-TNFalpha was used as template for PCR amplification of a signal peptide SP3 and vector skeletal by PrimeSTAR® HS Premix (TAKARA BIO, Inc.). The primers vector F3 and vector R2 was used (Table 14), in which the 15 nucleotides on the 5' side of each primer had a homologous sequence to the insert terminal. PCR program consisted of 30 cycles of 10 seconds at 98° C., 5 seconds at 55° C., 4 minutes at 72° C., followed by 30 seconds at 72° C.

A part of the PCR product was electrophoresed on 0.8% agarose gel (1×TBE buffer, containing ethidium bromide) with DNA concentration marker, confirming a single band of approximately 4 kbps and estimating its concentration.

TABLE 14

Primers for constructing pSP3B-hIL18mut

| Primers | Sequence (5' -> 3') | PCR product |
|---|---|---|
| IL18 F2 primer | TACTTCGGCAAGCTGGC (SEQ ID NO: 137) | insert |
| IL18 R2 primer | GAGCAGAAGGTCATCAATCCTC GTTCTGGACGGTG (SEQ ID NO: 138) | insert |
| vector_F3 primer | GATGACCTTCTGCTCGTAGCG (SEQ ID NO: 139) | vector |
| vector_R2 primer | CAGCTTGCCGAAGTAGGCGAT GGTCAGCTTGCC (SEQ ID NO: 140) | vector |

Cloning 100 ng of the vector and 40 ng of the insert above were ligated by the recombination of terminal sequences using In-Fusion Advantage PCR Cloning Kit (TAKARA BIO, Inc.). At this time, Cloning Enhancer (TAKARA BIO, Inc.) was also added into the reaction solution for concurrently degrading the template plasmid contained within the insert and the vector. Details were in accordance with the product instruction of In-Fusion Advantage PCR Cloning Kit.

2 µL of the In-Fusion reaction solution above was used for transforming *E. coli* TOP10 chemically Competent Cell (Invitorogen). Transforming conditions were in accordance with the product instruction. Transformed *E. coli* colonies were cultured overnight in LB (containing 75 µg/mL spectinomycin) liquid medium at 37° C., from which the plasmid was extracted (QIAprep Spin Miniprep Kit, QIAGEN). This plasmid was fully sequenced and named as pSP3B-hIL18mut (SEQ ID No: 49).

Transformation of *Bifidobacterium*

The plasmid pSP3B-hIL18mut was used for transforming *B. longum* 105A and *B. breve* JCM1192 in a similar method as Production Example 1.

Working Example 9

Human IL-18 Protein Expression by Recombinant *Bifidobacterium*

Sample Preparation

The glycerin stocks of the recombinant bifidobacteria *Bifidobacterium longum* 105A/pSP3B-hIL18mut obtained from Production Example 9 and *Bifidobacterium longum* 105A/pBEshuttle obtained from Reference Example 4 were inoculated at 1% to APS-2S-2.5SE (75 µg/mL spectinomycin) liquid media, cultured at 37° C. for 24 hours in anaerobic condition (activating culture solution). Subsequently, the activating culture solution was inoculated at 0.5% to a medium (for each 20 mL of APS-2S-2.5SE (75 µg/mL spectinomycin) liquid medium 4 mL of 1M sodium phosphate buffer (pH6.8) was added), which was cultured at 37° C. for 18 hours in anaerobic condition (main culture solution).

*Bifidobacterium breve* JCM1192/pSP3B-hIL18mut was cultured in a similar method as above, except that the main culture was cultured for 14 hours.

1.3 mL of the main culture solution was measured to a tube with a capacity of 1.5 mL, centrifuged (14,000 rpm for 5 minutes at 4° C.), and the supernatant was collected to give a sample for IL-18 measurement.

IL-18 Measurement

The protein content of the human IL-18 in each supernatant was measured using Human IL-18 ELISA kit (MBL). As a result, 986 pg/mL of IL-18 was detected in *Bifidobacterium longum* 105A/pSP3B-hIL18 and 1632 pg/mL in *Bifidobacterium breve* JCM1192/pSP3B-hIL18mut, although none was detected in the mock.

INDUSTRIAL APPLICABILITY

Introducing the secretory signal peptide of the present invention into an expression cassette enables an efficient secretion of an expressed protein from a transformed bacterium without impairing its physiological activity. Accordingly, the vector of the present invention and the anaerobic microorganism transformed with said vector are capable of more efficiently providing a therapeutic agent to a disease site in an anaerobic disease tissue compared with those of conventional use, thereby being capable of providing a high therapeutic effect.

The invention claimed is:

1. A transforming plasmid for producing a transformed anaerobic bacterium, the plasmid comprising an expression cassette containing a secretory signal that functions in the anaerobic bacterium, wherein the secretory signal comprises a nucleotide sequence encoding a secretory signal peptide encoded by SEQ ID NO: 6, 7, 8, 9, 12, 14, 15, 17, 21 or 25.

2. The transforming plasmid according to claim 1, wherein the anaerobic bacterium is *Bifidobacterium*.

3. The transforming plasmid according to claim 1, wherein the secretory signal comprises a nucleotide sequence encoding a secretory signal peptide encoded by SEQ ID No.: 8 or 25.

4. The transforming plasmid according to claim 1, wherein a promoter contained in the expression cassette is the nucleotide sequence of SEQ ID NO: 45.

5. The transforming plasmid according to claim 1, wherein a terminator contained in the expression cassette is a DNA according to the nucleotide sequence of SEQ ID NO: 46.

6. The transforming plasmid according to claim 1, wherein a target gene contained in the expression cassette is a gene encoding a protein having an antitumor activity.

7. The transforming plasmid according to claim 6, wherein the protein having an antitumor activity is one selected from the group consisting of interleukin (IL)-18 and tumor necrosis factor (TNF)-α.

8. The transforming plasmid according to claim 7, wherein the protein having an antitumor activity is tumor necrosis factor (TNF)-α.

9. The transforming plasmid according to claim 1, comprising a DNA sequence according to the nucleotide sequence of SEQ ID No.: 5 (pBifi-SP3B-TNF alpha).

10. A gene transfer carrier consisting of an anaerobic bacterium transformed with the transforming plasmid according to claim 1.

11. The gene transfer carrier according to claim 10, wherein the anaerobic bacterium is an avirulent enterobacterium.

12. The gene transfer carrier according to claim 10, wherein the anaerobic bacterium is *Bifidobacterium*.

13. The gene transfer carrier according to claim 12, wherein the *Bifidobacterium* is a species selected from the group consisting of *Bifidobacterium adolescentis, Bifidobacterium angulatum, Bifidobacterium animalis, Bifidobacterium asteroides, Bifidobacterium bifidum, Bifidobacterium bourn, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacteria globosum, Bifidobacteria indicum, Bifidobacterium infantis, Bifidobacteria inopinatum, Bifidobacterium lactis, Bifidobacterium lactentis, Bifidobacterium liberorum, Bifidobacterium longum, Bifidobacterium magnum, Bifidobacterium merycicum, Bifidobacterium minimum, Bifidobacterium mongoliense, Bifidobacterium parvulorum, Bifidobacterium pseudocatenulatum, Bifidobacterium pseudolongum, Bifidobacterium psychroaerophilum, Bifidobacterium pullorum, Bifidobacterium ruminate, Bifidobacterium ruminantium, Bifidobacterium saeculare, Bifidobacterium scardovii, Bifidobacterium subtile, Bifidobacterium suis, Bifidobacterium thermacidophilum and Bifidobacterium thermophilum.*

14. The gene transfer carrier according to claim 13, wherein the *Bifidobacterium* is *Bifidobacterium longum*.

15. The gene transfer carrier according to claim 10, being capable of growing in a tumor tissue in an anaerobic environment and being capable of expressing and secreting at least one protein that is useful for treatment of an anaerobic disease.

16. The gene transfer carrier according to claim 15, wherein the protein has an antitumor activity and is selected from the group consisting of interleukin (IL)-18 and tumor necrosis factor (TNF)-α.

17. A pharmaceutical composition comprising the gene transfer carrier according to claim 10.

18. The gene transfer carrier according to claim 16, wherein the protein is tumor necrosis factor (TNF)-α.

19. A pharmaceutical composition comprising the gene transfer carrier according to claim 12.

20. A pharmaceutical composition comprising the gene transfer carrier according to claim 13.

21. A pharmaceutical composition comprising the gene transfer carrier according to claim 14.

22. The transforming plasmid according to claim 7, wherein the protein having an antitumor activity is interleukin (IL)-18.

23. The gene transfer carrier according to claim 16, wherein the protein is interleukin (IL)-18.

* * * * *

UNITED STATES PATENT AND TRADEMARK OFFICE
CERTIFICATE OF CORRECTION

| | |
|---|---|
| PATENT NO. | : 8,535,939 B2 |
| APPLICATION NO. | : 13/015806 |
| DATED | : September 17, 2013 |
| INVENTOR(S) | : Shimatani-Shibata et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 60 days.

Signed and Sealed this
Fifth Day of May, 2015

Michelle K. Lee
*Director of the United States Patent and Trademark Office*

UNITED STATES PATENT AND TRADEMARK OFFICE
CERTIFICATE OF CORRECTION

PATENT NO. : 8,535,939 B2
APPLICATION NO. : 13/015806
DATED : September 17, 2013
INVENTOR(S) : Yuko Shimatani-Shibata et al.

It is certified that error appears in the above-identified patent and that said Letters Patent is hereby corrected as shown below:

In the Claims:

Claim 13, column 137, line 15, should read:

13. The gene transfer carrier according to Claim 12, wherein the *Bifidobacterium* is a species selected from the group consisting of *Bifidobacterium adolescentis, Bifidobacterium angulatum, Bifidobacterium animalis, Bifidobacterium asteroides, Bifidobacterium bifidum, Bifidobacterium boum, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacteria globosum, Bifidobacteria indicum, Bifidobacterium infantis, Bifidobacteria inopinatum, Bifidobacterium lactis, Bifidobacterium lactentis, Bifidobacterium liberorum, Bifidobacterium longum, Bifidobacterium magnum, Bifidobacterium merycicum, Bifidobacterium minimum, Bifidobacterium mongoliense, Bifidobacterium parvulorum, Bifidobacterium pseudocatenulatum, Bifidobacterium pseudolongum, Bifidobacterium psychroaerophilum, Bifidobacterium pullorum, Bifidobacterium ruminale, Bifidobacterium ruminantium, Bifidobacterium saeculare, Bifidobacterium scardovii, Bifidobacterium subtile, Bifidobacterium suis, Bifidobacterium thermacidophilum* and *Bifidobacterium thermophilum.*

Signed and Sealed this
Seventh Day of June, 2016

Michelle K. Lee
*Director of the United States Patent and Trademark Office*